US007915424B2

(12) United States Patent (10) Patent No.: US 7,915,424 B2
Agejas-Chicharro et al. (45) Date of Patent: Mar. 29, 2011

(54) PYRIDYL DERIVATIVES AND THEIR USE AS MGLU5 ANTAGONISTS

(75) Inventors: Francisco Javier Agejas-Chicharro, Madrid (ES); Bruce Anthony Dressman, Indianapolis, IN (US); Jose Antonio Martinez Perez, Madrid (ES); James Allen Monn, Indianapolis, IN (US); Mohammad Sadegh Zia-Ebrahimi, Indianapolis, IN (US); Sonia Gutierrez Sanfeliciano, Madrid (ES); Steven Marc Massey, Indianapolis, IN (US); Steven Scott Henry, New Palestine, IN (US)

(73) Assignee: Eli Lilly and Company, Indianapolis, IN (US)

(*) Notice: Subject to any disclaimer, the term of this patent is extended or adjusted under 35 U.S.C. 154(b) by 649 days.

(21) Appl. No.: 10/598,512

(22) PCT Filed: Mar. 9, 2005

(86) PCT No.: PCT/US2005/007507
§ 371 (c)(1),
(2), (4) Date: Sep. 1, 2006

(87) PCT Pub. No.: WO2005/094822
PCT Pub. Date: Oct. 13, 2005

(65) Prior Publication Data
US 2008/0194647 A1 Aug. 14, 2008

Related U.S. Application Data

(60) Provisional application No. 60/555,137, filed on Mar. 22, 2004.

(51) Int. Cl.
*C07D 211/78* (2006.01)
(52) U.S. Cl. ........ 546/286; 546/348; 546/287; 546/315; 546/345
(58) Field of Classification Search .................. 546/322, 546/286; 514/356, 344
See application file for complete search history.

(56) References Cited

U.S. PATENT DOCUMENTS
2003/0225070 A1  12/2003  Mutel et al.

FOREIGN PATENT DOCUMENTS

| EP | 0436 398 B1 | 1/1996 |
| WO | WO 96/01825 A | 1/1996 |
| WO | WO 97/24355 A | 7/1997 |
| WO | WO 01/16121 A1 | 3/2001 |
| WO | WO 01/72291 A | 10/2001 |
| WO | WO 01/72709 A1 | 10/2001 |
| WO | WO 01/90101 A | 11/2001 |
| WO | WO 03/035620 | 5/2003 |
| WO | WO 2004/067002 A | 8/2004 |

OTHER PUBLICATIONS

Hoekstra et. al., "Potent, Orally Active GPIIb/IIa Antagonists Containing a Nipecotic Acid Subunit. Structure-Activity Studies Leading to the Discovery of RWJ-53308", Journal of Medicinal Chemistry, American Chemical Society. Washington, DC, vol. 42, No. 2, 1999, pp. 5254-5265.*
Hcaplus 130:124995, "Preparation of pyridine derivatives for treating disorders mediated full or in part by mGluR5", Allgeier, Hans et. al., 1999.*
Patani et. al., "Bioisosterism: A Rational Approach in Drug Design", Chem. Rev., 96, pp. 3147-3176.*
Hoekstra, et al., Potent, Orally Active GPIIb/IIIa Antagonists Containing a Nipecotic Acid Submit. Structure-Activity Studies Leading to the Discovery of RWJ-53308; *Journal of Medicinal Chemistry, American Chemical Society*, Washington, US vol. 42, No. 25, 1999, pp. 5254-5265, XP002142349 ISSN: 0022-2623.
Sorensen, et al., "Cooper-free palladium-catalyzed sonogashira-type coupling of aryl halides and 1-aryl-2-(trimethylsilyl) acetylenes" Tetrahendron, *Elsevier Science Publishers*, Amsterdam, N.; vol. 61 (10) 2697-27-0, 2005.
Novak, et al., "Tandem Sonogashira coupling: An efficient tool for the synthesis of Diarylalkynes" Organic Letters vol. 6(36), 4917-4920 Coden: ORLEF7:ISSN: 1523-7060, 2004.
Wolf, et al., "Palladium-phosphinous acid-catalyzed Sonogashira cross-coupling reaction in water" *Organic & Biomolecular Chemistry*, vol. 2(15) 2161-2164 Coden: OBCRAK; ISSN:1477-0520. XP002331795 see Table 2,compounds 18, 20 (2004).
He H et al., "Cooper-catalyzed cross-coupling of aryliodides and aryl acetylenes using microwave heating" *Tetrahedron Letters, Elsevier Science Publishers*, Amsterdam, NL, vol. 45(16), 3237-3239, XP004498987, (2004).

(Continued)

*Primary Examiner* — Janet L Andres
*Assistant Examiner* — Heidi Reese
(74) *Attorney, Agent, or Firm* — Mark A. Winter; Arvie J. Anderson

(57) ABSTRACT

The present invention is directed toward pyridyl derivatives of formula (I) as antagonists of the mGlu5 receptor. As such the compounds may be useful for treatment or prevention of disorders remedied by antagonism of the mGlu5 receptor, wherein Ar is phenyl or napthyl each of which may be substituted by one or more $C_1$-$C_4$ alkyl, $C_1$-$C_4$ alkoxy, $C_1$-$C_5$ acyl, halo, amino, nitro, cyano, hydroxy, $C_1$-$C_5$ acylamino, $C_1$-$C_4$ alkylsulfonylamino, mono-, di- or trifluorinated $C_1$-$C_3$ alkyl, substituents which may be the same or different and may bear a $CONH_2$, $CONHCH_3$, $CON(CH_3)_2$, $CO_2H$, $CO_2CH_3$, $OCF_3$, $CH_2NHCOCH_3$, $CH_2NH_2$, $CH_2N(CH_3)_2$, $CH_2CN$, $CH_2OH$, $CH_2NHSO_2CH_3$, $CH_2N(CH_3)(CH_2)_2 CN$, $CH_2N(CH_3)CH(CH_3)_2$, $CH_2NHCH(CH_3)_2$, $CH_2NH(CH_2)_2 CH_3$, $CH_2NHCO_2R^4$, $CH_2NHCH_2CH_3$, $CH_2NHCH_3$ $NHCOC(CH_3)_2$, or $N(S(O)_2CH_3)_2$ substituent; $R^1$ is hydrogen, halo, $R^4$, CN, C(NOH)$R^3$, C(NO—$R^4$)$R^3$, $(CH_2)_2CO_2R^4$, $(CH_2)_n$ OR$^3$, COR$^3$, CF$_3$, SR$^4$, S(O)R$^4$, S(O)$_2$R$^4$, COCH$_2$CO$_2$R$^3$, NHSO$_2$R$^4$, NHCOR$^3$, C(NOR$^3$)NH$_2$, $CH_2OCOR^3$, $(CH_2)_n NH_2$, $CON(CH_3)_2$ $(CH_2)_n NHCO_2R^4$, $CO_2R^3$, $CONH_2$, $CSNH_2$, $C(NH)NHOR^3$, $(CH_2)_n N(CH_3)_2$, or $CONHNHCOR^3$; $R^2$ is 1,2-ethenediyl or 1,2-ethynediyl; $R^3$ is hydrogen or $C_1$-$C_4$ alkyl; $R^4$ is $C_1$-$C_4$ alkyl; and n is 0, 1, 2, 3 or 4; or a pharmaceutically acceptable salt thereof, or an N-oxide thereof.

(I)

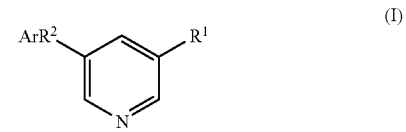

7 Claims, No Drawings

OTHER PUBLICATIONS

Penney, et al., "Alkynylation of benzonitriles via nickel catalyzed C-C bond activation" *Tetrhedron Letters, Elevier Science Publishers*, Amsterdam, NL, vol. 45(25) Xp004510991. 2004.

Sun, Shih-Sheng, et al., "Directed Assembly of Transition-Metal Coordinated Molecular Loops and Squares from Salen-Type Components. Examples of Metalation-Controlled Structural Conversion", *Journal of the American Chemical Society*, vol. 126(20), 6315, XP002331796 (2004).

Rajadurai, et al., "Study on the Heteroatom Influence in Pyridine-Based Nitronyl Nitroxide Biradicals with Phenylethynyl Spacers on the Molecular Ground State" Journal of Organic Chemistry, vol. 68(26) 9907-9915, (2003).

Katritzky, et al., "The preparation of diarylacetylenes via diphenyl (benzotriazol-l-yl)aryl)methylphosphonates" *ARKIVOC* (Gainesville, FL, United States), 17-27 Coden, (2002).

Wang, et al., "An improved coupling reaction for the preparation of pyridylethynyl benzonitrile compounds", *Chinese Science Bulletin*, vol. 46(19) 1606-1608, (2001).

Lin, et al., "Three-Dimensional Manganese (II) Coordination Polymers Based on m-Pyridinecarboxylates: Synthesis, X-ray Structures, and Magnetic Properties" *Inorganic Chemistry*, vol. 39(18) 4169-4173 (2000).

Mallik, et al., "Crystal Growth And Design", vol. 5(2), 9-14 (2004).

Lane, "Neurochemical Changes Associated with the Action of Acute Administration of Diazepam in Reversing the Behavioral Paradigm Conditioned Emotional Response", *Neurochemical Research, Bol.* vol. 17(5), 497-507 (1992).

Spooren, et al., Pharmacological and endocrinological characterization of stress-induced hyperthermia in singly housed mice using classical and candidate anxiolytics (LY314582, MPEP and NKP608), *European Journal of Pharmacology*, vol. 435, 161-170 (2002).

Zethof, et al., "Stress-induced hyperthermia as a putative anxiety model", *European Journal of Pharmacology*, vol. 294, 125-135 (1995).

Sanger, "Effects of Buspirone and Related Compounds on Suppressed Operant Responding in Rats" *The Journal of Pharmacology and Experimental Therapeutics*, vol. 254(2) 420-502 (1990).

Jones, et al., "Abnormalities In Expression Of Human Retinal mRNA In Retinitis Pigmentosa" *Neurochem. Int.* vol. 17(3) 495-503 (1990).

Millenson, et al., "The Conditioned Emotional Response (CER) As A Baseline For The Study Of Anti-Anxiety Drugs", *Neuropharmacology*, vol. 13, 1-9 (1974).

Olivier, et al., "Stress Induced hyperthermia and anxiety: Pharmacological validation" *European Journal Of Pharmacology*, vol. 463, 117-132 (2003).

* cited by examiner

PYRIDYL DERIVATIVES AND THEIR USE AS MGLU5 ANTAGONISTS

This application is a United States national phase entry, pursuant to 35 U.S.C. 371, of PCT/US2005/007507, filed Mar. 9, 2005, which claims the benefit of United States provisional patent application Ser. No. 60/555,137, filed Mar. 22, 2004.

The present invention is directed toward pyridyl derivatives as antagonists of the mGlu5 receptor. As such the compounds may be useful for treatment or prevention of disorders remedied by antagonism of the mGlu5 receptor.

BACKGROUND OF THE INVENTION

In the mammalian central nervous system (CNS), the transmission of nerve impulses is controlled by the interaction between a neurotransmitter that is released by an afferent neuron and a surface receptor on a receiving neuron which causes excitation of the receiving neuron. L-Glutamate, which is the most abundant neurotransmitter in the CNS, mediates the major excitatory pathway in mammals and is referred to as an excitatory amino acid (EAA). The receptors that respond to glutamate are called excitatory amino acid receptors. The excitatory amino acids are of great physiological importance playing roles in a variety of physiological processes such as synaptic plasticity, motor control, respiration, cardiovascular regulation and sensory perception. Excitatory amino acid receptors are classified into two general types. Receptors that are directly coupled to the opening of cation channels in the cell membrane of the neurons are termed ionotropic. This type of receptor has been subdivided into at least three subtypes which are defined by the depolarizing actions of the selective agonists N-methyl-D-aspartic acid (NMDA), α-amino-3-hydroxy-5-methylisoxazole-4-propionic acid (AMPA) and kainic acid (KA). The second general type of receptor is the G-protein or second messenger-linked metabotropic excitatory amino acid receptor.

The metabotropic glutamate (mGlu) receptors belong to the super-family of G-protein coupled receptors and have been divided into three groups based on protein sequence homologies. Molecular cloning and functional expression studies in heterologous cell lines have shown that group I mGlu receptors: mGlu1 and mGlu5 and their spliced isoforms stimulate activation of phospholipase C (PLC) and mobilization of intracellular calcium whereas the group II (mGlu2 and 3) and III (mGlu4, 6,7 and 8) mGlu receptors negatively modulate adenyl cyclase. Stimulation of mGlu 5 (and mGlu1) receptors promotes an increase in neuronal excitation and fast synaptic transmission via potentiation of NMDA and AMPA receptor mediated responses, induction of $Ca^{2+}$-depolarization by inhibition of several $K^+$ channels, activation of dependent and $Ca^{2+}$-independent non-selective cationic inward currents, enhancement of presynaptic glutamate release and enhancement of $Na^+/Ca^{2+}$ exchange. In addition to the activation of PLC, the signaling of group I mGlu receptors has also been shown to involve activation of other intracellular enzymes including phospholipase D, adenylate cyclase, tyrosine kinase and MAP kinases. In situ studies have shown that mGlu5 receptor splice variants (mGlu5a, b, c and d receptors) are localized peri- or extrasynaptically on the post synaptic membrane and are expressed in key neuroanatomical sites of the brain and spinal cord associated with psychiatric and neurological dysfunctions.

EP 0 436 398 B1 discloses acetylenes disubstituted with a heteroaromatic group and a substituted phenyl group having retinoid like activity.

WO 01/16121 discloses heterocyclic compounds and methods of use thereof.

U.S. Patent Publication No. 2003/0225070 A1 discloses phenylethynyl and styryl derivatives of imidazole and fused ring heterocycles.

WO 01/72709 A1 discloses naphthalene derivatives and their pharmaceutical use.

5-Phenylethynyl-nicotinonitrile is commercially available from Maybridge Chemical Co., Ltd.

Compounds of the present invention are useful as mGlu5 receptor antagonists and may have certain advantages over other mGlu5 receptor antagonists such as increased potency; enhanced mGlu5 selectivity vs. other CNS receptor and transporter targets; avoidance of undesirable activities, including reactive metabolite formation and inhibition of cytochrome p450 isozyme CYP1A2; superior mGlu5 receptor occupancy; or superior efficacy in rodent models of anxiety and depression. (Animal models for anxiety include, for example, the conditional emotional response model, Neuropharmacology, 13(1):1-9 (1974), J. Pharmacol. Exp. Ther., 254(2):420-426 (1990), Neurochem. Res., 17(5):497-507 (1992) or the Stress-Induced Hyperthermia model, Eur. J. Pharmacol., 294(1):125-135, Eur. J. Pharmacol., 435(2-3):161-170, Eur. J. Pharmacol., 463(1-3):117-132).

The compounds of the present invention have now been found to act as antagonists of mGlu5 receptors.

DETAILED DESCRIPTION OF THE INVENTION

The present invention provides a method for treating a disorder remedied by antagonism of mGlu5 receptors in a patient which comprises administering to a patient in need thereof an effective amount of a compound of formula 1:

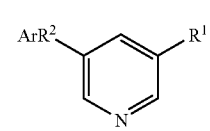

(1)

wherein

Ar is phenyl or napthyl each of which may be substituted by one or more $C_1$-$C_4$ alkyl, $C_1$-$C_4$ alkoxy, $C_1$-$C_5$ acyl, halo, amino, nitro, cyano, hydroxy, $C_1$-$C_8$ acylamino, $C_1$-$C_4$ alkylsulfonylamino, mono-, di- or trifluorinated $C_1$-$C_3$ alkyl, substituents which may be the same or different and may bear a $CONH_2$, $CONHCH_3$, $CON(CH_3)_2$, $CO_2H$, $CO_2CH_3$, $OCF_3$, $CH_2NHCOCH_3$, $CH_2NH_2$, $CH_2N(CH_3)_2$, $CH_2CN$, $CH_2OH$, $CH_2NHSO_2CH_3$, $CH_2N(CH_3)(CH_2)_2$ CN, $CH_2N(CH_3)CH(CH_3)_2$, $CH_2NHCH(CH_3)_2$, $CH_2NH(CH_2)_2CH_3$, $CH_2NHCO_2R^4$, $CH_2NHCH_2CH_3$, $CH_2NHCH_3$, $NHCOC(CH_3)_2$, or $N(S(O)_2CH_3)_2$ substituent;

$R^1$ is hydrogen, halo, $R^4$, CN, C(NOH)$R^3$, C(NO—$R^4$)$R^3$, $(CH)_2CO_2R^4$, $(CH_2)_n$ $OR^3$, $COR^3$, $CF_3$, $SR^4$, $S(O)R^4$, $S(O)_2R^4$, $COCH_2CO_2R^3$, $NHSO_2R^4$, $NHCOR^3$, $C(NOR^3)NH_2$, $CH_2OCOR^3$, $(CH_2)_nNH_2$, $CON(CH_3)_2$, $(CH_2)_nNHCO_2R^4$, $CO_2R^3$, $CONH_2$, $CSNH_2$, $C(NH)NHOR^3$, $(CH_2)_nN(CH_3)_2$, or $CONHNHCOR^3$;

$R^2$ is 1,2-ethenediyl or 1,2-ethynediyl;

$R^3$ is hydrogen or $C_1$-$C_4$ alkyl;

$R^4$ is $C_1$-$C_4$ alkyl; and n is 0, 1, 2, 3 or 4;

or a pharmaceutically acceptable salt thereof; or an N-oxide thereof.

The present invention also provides a method for treating a disorder remedied by antagonism of mGlu5 in a patient which comprises administering to the patient in need of treatment thereof an effective amount of a compound of formula 1 wherein Ar is $C_1$-$C_4$ alkyl, $C_1$-$C_4$ alkoxy, $C_1$-$C_5$ acyl, halo, amino, nitro, cyano, hydroxy, $C_1$-$C_5$ acylamino, $C_1$-$C_4$ alkylsulfonylamino or mono-, di- or trifluorinated $C_1$-$C_3$ alkyl; and $R^1$ is hydrogen, halo, $R^4$, CN, C(NOH)$R^3$, C(NO$R^4$)$R^3$, (CH)$_2$CO$_2$—$R^4$, O$R^3$, CO$R^3$ or CF$_3$.

Further, the present invention provides a method for treating a disorder remedied by antagonism of mGlu5 receptors in a patient which comprises administering to the patient in need of treatment thereof an effective amount of a compound of formula 1 wherein the disorder is pain or anxiety. Also, the present invention provides a method for treating a disorder remedied by antagonism of mGlu5 in a patient which comprises administering to the patient in need of treatment thereof an effective amount of a compound of formula 1 wherein the patient is a human.

The present invention also provides a compound of formula 1:

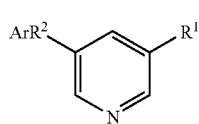

(1)

wherein

Ar is phenyl or napthyl each of which may be substituted by one or more $C_1$-$C_4$ alkyl, $C_1$-$C_4$ alkoxy, $C_1$-$C_5$ acyl, halo, amino, nitro, cyano, hydroxy, $C_1$-$C_5$ acylamino, $C_1$-$C_4$ alkylsulfonylamino, mono-, di- or trifluorinated $C_1$-$C_3$ alkyl, substituents which may be the same or different and may bear a CONH$_2$, CONHCH$_3$, CON(CH$_3$)$_2$, CO$_2$H, CO$_2$CH$_3$, OCF$_3$, CH$_2$NHCOCH$_3$, CH$_2$NH$_2$, CH$_2$N(CH$_3$)$_2$, CH$_2$CN, CH$_2$OH, CH$_2$NHSO$_2$CH$_3$, CH$_2$N(CH$_3$)(CH$_2$)$_2$ CN, CH$_2$N(CH$_3$)CH(CH$_3$)$_2$, CH$_2$NHCH(CH$_3$)$_2$, CH$_2$NH(CH$_2$)$_2$CH$_3$, CH$_2$NHCO$_2$R$^4$, CH$_2$NHCH$_2$CH$_3$, CH$_2$NHCH$_3$, NHCOC(CH$_3$)$_2$, or N(S(O)$_2$CH$_3$)$_2$ substituent;

$R^1$ is hydrogen, halo, $R^4$, CN, C(NOH)$R^3$, C(NO—$R^4$)$R^3$, (CH)$_2$CO$_2$R$^4$, (CH$_2$)$_n$ OR$^3$, COR$^3$, CF$_3$, SR$^4$, S(O)R$^3$, S(O)$_2$R$^3$, COCH$_2$CO$_2$R$^4$, NHSO$_2$R$^4$, NHCOR$^3$, C(NOR$^3$)NH$_2$, CH$_2$OCOR$^3$, (CH$_2$)$_n$NH$_2$, CON(CH$_3$)$_2$, (CH$_2$)$_n$NHCO$_2$R$^4$, CO$_2$R$^3$, CONH$_2$, CSNH$_2$, C(NH)NHOR$^3$, (CH$_2$)$_n$N(CH$_3$)$_2$, or CONHNHCOR$^3$, R$^2$ is 1,2-ethenediyl or 1,2-ethynediyl;

$R^3$ is hydrogen or $C_1$-$C_4$ alkyl;

$R^4$ is $C_1$-$C_4$ alkyl; and n is 0, 1, 2, 3 or 4;

or a pharmaceutically acceptable salt thereof; or an N-oxide thereof; provided that the compound is other than 5-phenylethynyl-nictinonitrile.

In a particular embodiment of a compound of formula 1, n is 0 or 1.

A particular compound of formula 1 is one wherein Ar is phenyl substituted by one or more halo, $C_1$-$C_4$ alkyl, CN, $C_1$-$C_4$ alkoxy, CF$_3$, NO$_2$, NH$_2$, OH, COCH$_3$, substituents which may be the same or different and may bear a CONH$_2$, CONHCH$_3$, CON(CH$_3$)$_2$, CO$_2$H, CO$_2$CH$_3$, OCF$_3$, CH$_2$NHCOCH$_3$, CH$_2$NH$_2$, CH$_2$N(CH$_3$)$_2$, CH$_2$CN, CH$_2$OH, CH$_2$NHSO$_2$CH$_3$, CH$_2$N(CH$_3$)(CH$_2$)$_2$ CN, CH$_2$N(CH$_3$)CH(CH$_3$)$_2$, CH$_2$NHCH(CH$_3$)$_2$, CH$_2$NH(CH$_2$)$_2$CH$_3$, CH$_2$NHCO$_2$C(CH$_3$)$_3$, CH$_2$NHCH$_2$CH$_3$, CH$_2$NHCH$_3$ or NHCOC(CH$_3$)$_2$ substituent.

In another particular embodiment of a compound of formula 1, halo is fluoro, iodo, choro or bromo; alkyl is methyl, ethyl, propyl, isopropyl or isobutyl; and alkoxy is methoxy.

In yet another particular embodiment of a compound of formula 1, Ar is 2-chlorophenyl, 3-chlorophenyl, 2-fluorophenyl, 3-fluorophenyl, 4-fluorophenyl, 3,4-dimethylphenyl, 3,5-dimethylphenyl, 2,4-dimethylphenyl, 2,5-dimethylphenyl, 2-cyanophenyl, 3-cyanophenyl, 4-cyanophenyl, 2-methoxyphenyl, 3-methoxyphenyl, 4-methoxyphenyl, 4-chlorophenyl, 2-methylphenyl, 3-methylphenyl, 4-methylphenyl, 3,4-difluorophenyl, 3,5-difluorophenyl, 3,4,5-trifluorophenyl, 3-bromophenyl, 3-nitrophenyl, 3-trifluoromethylphenyl, 3-aminophenyl, 3-chloro-4-fluorophenyl, 3-hydroxyphenyl, 3-acetylphenyl, 5-chloro-2-methoxyphenyl, 3-chloro-4-methoxyphenyl, 3-hydroxy-4-fluorophenyl, 3-methoxy-4-fluorophenyl, 3-ethoxy-4-fluorophenyl, 3-isopropoxy-4-fluorophenyl, 3-isopropylphenyl, 3-ethylphenyl, 3-methyl-4-fluorophenyl, 3-trifluoromethyl-4-fluorophenyl, 3-cyano-4-fluorophenyl, 3-amino-4-fluorophenyl, 3-trifluoromethyl-4-fluorophenyl, 3-chloro-4-fluorophenyl, 3-nitro-4-fluorophenyl, 3-aminocarbonyl-4-fluorophenyl, 3-N-methylaminocarbonyl-4-fluorophenyl, 3-N,N-dimethylaminocarbonyl-4-fluorophenyl, 3-carboxyl-4-fluorophenyl, 3-methoxycarbonyl-4-fluorophenyl, 3-acetylaminomethyl-4-fluorophenyl, 3-methylsulfonylaminomethyl-4-fluorophenyl, 3-pivaloylaminomethyl-4-fluorophenyl, 3-trifluoromethoxyphenyl, 3-aminomethyl-4-fluorophenyl, 3-dimethylaminomethyl-4-fluorophenyl, 3-cyanomethyl-4-fluorophenyl, 4-fluoro-3-hydroxymethylphenyl, 3-{[(2-cyanoethyl)-methylamino]-methyl}-4-fluorophenyl, 4-fluoro-3-[(isopropylmethylamino)-methyl]phenyl, 4-fluoro-3-isopropylaminomethylphenyl, 4-fluoro-3-propylaminomethylphenyl, 3-ethylaminomethyl-4-fluorophenyl, 4-fluoro-3-methyl aminomethylphenyl, 3-isobutyrylamino-4-fluorophenyl or 3-aminophenyl.

In another particular embodiment of a compound of formula 1, $R^1$ is hydrogen, bromo, iodo, fluoro, chloro, C(NOH)$R^3$, C(NO—R$^4$)R$^3$, methyl, CN, CH$_2$CO$_2$R$^4$, (CH$_2$)$_n$OR$^3$, COR$^3$, CF$_3$, SR$^4$, S(O)R$^4$, S(O)$_2$R$^4$, COCH$_2$CO$_2$R$^3$, NHS(O)$_2$ R$^3$NHCOR$^3$, CH$_2$OC(O)R$^3$, (CH$^2$)$_n$NH$_2$, CON(CH$_3$)$_2$, (CH$_2$)$_n$, NHCO$_2$R$^4$, CO$_2$R$^3$, CONH$_2$, CSNH$_2$, C(NH) NHOR$^3$, (CH$_2$)$_n$N(CH$_3$)$_2$ or CONHNHCOR$^3$.

In a particular embodiment R$^2$ is 1,2-ethynediyl.

In yet another particular embodiment for method of treatment, ArR$^2$ is phenyl-ethynyl and R$^1$ is CN. In a more particular embodiment, ArR$^2$ is phenyl-ethynyl and R$^1$ is CN wherein phenyl is substituted.

In a particular embodiment R$^1$ is CN iodo, chloro, methyl or COR$^3$ In an even more particular embodiment, R$^1$ is CN.

When R$^1$ or R$^3$ is alkyl, a particular alkyl group is methyl.

When R$^1$ is COR$^3$, a particular value for R$^3$ is hydrogen or methyl.

In another particular embodiment of a compound of formula 1, Ar is phenyl.

In another particular embodiment of a compound of formula 1, Ar is substituted phenyl.

Another particular embodiment of a compound of formula 1 is one wherein Ar is phenyl of napthyl each of which may be substituted by $C_1$-$C_4$ alkyl, $C_1$-$C_4$ alkoxy, $C_1$-$C_5$ acyl, halo, amino, nitro, cyano, hydroxy, $C_1$-$C_5$ acylamino, $C_1$-$C_4$ alkylsulfonylamino or mono-, di- or trifluorinated $C_1$-$C_3$ alkyl; and $R^1$ is hydrogen, halo, R$^4$, CN, C(NOH)R$^3$, C(NOR$^4$)R$^3$ (CH)$_2$CO$_2$R$^4$, OR$^3$, COR$^3$ or CF$_3$.

In yet another particular embodiment of a compound of formula 1, $R^3$ is hydrogen, methyl, ethyl or t-butyl.

In another embodiment, the present invention provides a compound of Formula 1, or a pharmaceutically acceptable salt thereof, or an N-oxide thereof, for use in therapy. In particular, the present invention provides a compound of Formula 1, or a pharmaceutically acceptable salt thereof, or an N-oxide thereof, for use as an antagonist of mGlu5 receptors.

In another embodiment, the present invention provides a method for antagonizing mGlu5 receptors, comprising administering to a mammal in need of such inhibition an effective amount of a compound of Formula 1 or a pharmaceutically acceptable salt thereof, or an N-oxide thereof. In particular, the present invention provides a method for treating a disorder which is caused by or linked to antagonism of the mGlu5 receptor comprising administering to a mammal in need of such treatment an effective amount of a compound of Formula 1 or a pharmaceutically acceptable salt thereof, or an N-oxide thereof. Such disorders include, for example, psychosis, stroke, pain or Alzheimer's disease. Such disorders also include impairment of cognition, drug dependency, anxiety or depression. Particular disorders are anxiety and pain, including neuropathic pain. The compounds of Examples 14, 21 and 58 may be particularly useful for the treatment of anxiety and/or pain.

In another alternative embodiment, the present invention provides for the use of a compound of Formula 1, or a pharmaceutically acceptable salt thereof, or an N-oxide thereof, for the manufacture of a medicament for antagonizing mGlu5 receptors. In particular, the present invention provides for the use of a compound of Formula 1 or a pharmaceutically acceptable salt thereof, or an N-oxide thereof, for the manufacture of a medicament for the treatment of a disorder which is caused by or linked to antagonism of mGlu5 receptors. Such disorders include, for example, anxiety and/or pain including neuropathic pain.

As used herein the term "effective amount" refers to the amount or dose of the compound, upon single or multiple dose administration to the patient, which provides the desired effect in the patient.

An effective amount can be readily determined by the attending physician, as one skilled in the art by the use of known techniques and by observing results obtained under analogous circumstances. In determining the effective amount or dose of compound administered, a number of factors are considered by the attending physician, including, but not limited to: the species of mammal; its size, age, and general health; the specific disease involved; the severity of the disease; the response of the individual patient; the particular compound administered; the mode of administration; the bioavailability characteristics of the preparation administered; the dose regimen selected; the use of concomitant medication; and other relevant circumstances. For example, a typical daily dose may contain from about 5 mg to about 500 mg, and more particularly about 25 mg to about 300 mg, of the compound of Formula 1 The compounds can be administered by a variety of routes including oral, rectal, transdermal, subcutaneous, intravenous, intramuscular, bucal or intranasal routes. Alternatively, the compound may be administered by continuous infusion.

"Alkyl" means an aliphatic hydrocarbon group which may be straight or branched.

"Halo" is bromo, chloro, iodo or fluoro.

In a specific embodiment, the term "about" or "approximately" means within 20%, preferably within 10%, and more preferably within 5% of a given value or range.

"Alkoxy" means an alkyl-O— group wherein the alkyl group is as herein described. Representative alkoxy groups include methoxy, ethoxy, n-propoxy, i-propoxy, n-butoxy and isopropoxy.

"N-oxide" means a moiety of the following structure

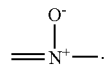

"Acyl" means an H—CO— or alkyl-CO— group wherein the alkyl group is as herein described. Preferred acyls contain a lower alkyl. Exemplary acyl groups include formyl, acetyl, propanoyl, 2-methylpropanoyl, butanoyl and palmitoyl.

"Acylamino" is an acyl-NH— group wherein acyl is as defined above herein.

"Alkylsulfonylamino" means alkyl-$SO_2$—NH— where the alkyl group is as herein described.

Representative mono, di or trifluoro substituted lower alkyl groups include —$CF_3$.

The present invention includes pharmaceutically acceptable salts of the compounds of Formula 1 "Pharmaceutically acceptable salts" refers to the relatively non-toxic, inorganic and organic acid addition salts, and salts made with a base of compounds of the present invention, for example hydrochloride salt. (See, for example 1 M. Berge, et al., "Pharmaceutical Salts," J. Pharm. Sci., 66: p. 1-19 (1977))

As mentioned above, the compounds of the present invention and their pharmaceutically acceptable salts, and N-oxides thereof, antagonize mGlu5 receptors. In view of these properties, the compounds of the present invention and their pharmaceutically acceptable salts, and N-oxides thereof, may be useful for treating disorders which are remedied by antagonism of mGlu5 receptors. The present invention provides compounds which antagonize mGlu5 receptors and may be useful in the treatment or prevention of mood affective disorders such as anxiety (including, for example generalized anxiety disorder, seasonal affective disorder, post traumatic stress disorder or social anxiety disorder) or depression as well as psychosis including bipolar disorder, post traumatic stress disorder or schizophrenia. In addition compounds of the instant invention may also be useful for the treatment of acute and chronic pain states associated with inflammation, cancer surgery and migraine. In particular, compounds of the instant invention may be useful for the treatment of anxiety and/or pain including neuropathic pain. Further, the compounds of the invention may be used in the treatment of acute neurodegenerative diseases, for example stroke, cerebral ischemia, head and spinal cord trauma, eye injury and chronic neurodegenerative diseases such as, for example, Alzheimer's disease, Parkinson's disease, Amyotropic lateral sclerosis, AIDS-induced dementia, senile dementia, anoxic injuries, and Huntington's Chorea and retinopathy. As antagonists of mGlu5 receptors compounds of the instant invention may be useful for treatment of addictive and compulsive behaviors, substance abuse and drug withdrawal (for example, reduction of self administration of cocaine, nicotine or alcohol), epilepsy, movement disorders, obesity, emesis, cognitive disorders, circadian rhythm and sleep disorders. Also as mGlu5 antagonists, compounds of the instant invention may be useful for treatment of gastro, esophageal reflux disease as well as for the treatment of regurgitation and asthma.

Accordingly, the present invention provides a compound of Formula 1, or a pharmaceutically acceptable salt thereof, or an N-oxide thereof, for use in therapy. In particular, the present invention provides a compound of Formula 1, or a pharmaceutically acceptable salt thereof, or an N-oxide thereof, for use as an antagonist of mGlu5 receptors.

In another embodiment, the present invention provides a method for antagonism of mGlu5 receptors, comprising administering to a patient in need of such inhibition an effective amount of a compound of Formula 1 or a pharmaceutically acceptable salt thereof, or an N-oxide thereof. In particular, the present invention provides a method for treating a disorder which is caused by or linked to modulation of the mGlu5 receptor comprising administering to a patient in need of such treatment an effective amount of a compound of Formula 1 or a pharmaceutically acceptable salt thereof, or an N-oxide thereof. Such disorders include, for example, psychosis, stroke, pain or Alzheimer's disease.

In the context of the present specification the terms "treating" and "treatment" include prophylactic treatment as well as therapeutic treatment.

"Patient" includes both human and other mammals.

In another alternative embodiment, the present invention provides for the use of a compound of Formula 1, or a pharmaceutically acceptable salt thereof, or an N-oxide thereof, for the manufacture of a medicament for modulation mGlu5 receptors. In particular, the present invention provides for the use of a compound of Formula 1 or a pharmaceutically acceptable salt thereof, or an N-oxide thereof, for the manufacture of a medicament for the treatment of a disorder which is caused by or linked to modulation of mGlu5 receptors. Such disorders include, for example, anxiety or pain.

The compounds may be administered by various routes and are usually employed in the form of a pharmaceutical composition. Such pharmaceutical compositions may be prepared by methods well known in the pharmaceutical art and normally comprise at least one active compound in association with a pharmaceutically acceptable carrier, diluent or excipient.

Accordingly, in a further embodiment, the present invention provides a pharmaceutical composition comprising a compound of Formula 1, or a pharmaceutically acceptable salt thereof, or an N-oxide thereof, together with a pharmaceutically acceptable carrier, diluent or excipient.

The compositions indicated can be sterilized and/or can contain auxiliaries such as lubricants, preservatives, stabilizers and/or wetting agents, emulsifiers, salts for affecting the osmotic pressure, buffer substances, colorants, flavorings and/or one or more further active compounds. Compositions of the invention may be formulated so as to provide, quick, sustained or delayed release of the active ingredient after administration to the patient by employing procedures well known in the art.

The compositions are preferably formulated in a unit dosage form, each dosage containing from about 5 to about 500 mg of the active ingredient.

In the context of the present specification, the term "unit dosage form" refers to physically discrete units suitable as unitary doses for human subjects and other mammals, each unit containing a predetermined quantity of one or more compounds of Formula 1 or pharmaceutically acceptable salts thereof, or N-oxides thereof, calculated to produce the desired therapeutic effect, together with a pharmaceutically acceptable carrier, diluent or excipient.

Compounds of the present invention are evaluated for effects on glutamate induced calcium flux responses using an AV-12 cell line expressing human recombinant mGlu5a receptor protein (see *Kingston et al Neuropharmacology.* 37(1):1-12, 1998). mGlu5 receptor mediated responses are determined by changes in intracellular calcium concentrations measured by a fluorescent calcium sensitive dye Fluo-3 Cells are harvested and seeded into 96 well microtiter plates. After 48 h incubation in a humidified incubator at 37° C., the cells are loaded with 10 μM fluo-3 AM dye for 60 min at 25° C. Unincorporated extracellular dye is removed from the wells by washing with buffer solution and plates are then transferred to a 96-channel fluorimetric imaging plate reader (FLIPR-Molecular Devices Corporation, La Jolla, Calif., USA). Baseline fluorescence readings are undertaken for 10 seconds prior to addition of test compounds by an automatic pipetting device integral to the FLIPR instrument. Following a 20 second delay, glutamate is then added to the wells at an $EC_{90\%}$ concentration (10 μM) and changes in fluorescence monitored over 60 seconds. The inhibitory effects of the compounds are determined by comparing the peak fluorescence response to glutamate in the presence and absence of compound. $IC_{50}$ values are calculated using a 4 parameter logistic curve fitting program (GraphPad™ Software). All exemplified compounds exhibit an $IC_{50}$ of less than 12.5 μM. Preferred compounds of the present invention which are tested according to the assay described above exhibit an $IC_{50}$ of <500 nM. The most preferred compounds exhibit an $IC_{50}$ or <100 nM As with any group of pharmaceutically active compounds, some groups are preferred in their end use application. Preferred embodiments of the present invention are discussed below.

A preferred compound of the present invention is selected from:
3-Phenylethynylpyridine, 5-Styrylnicotinonitrile,
5-(3,4-Dimethylphenylethynyl)-nicotinonitrile, 5-(2-Cyanophenylethynyl)nicotinonitrile,
3-Trifluoromethyl-5-phenylethynylpyridine,
3-(3-Trifluoromethyl-phenylethynyl)-pyridine hydrochloride,
3-Chloro-5-(3-trifluoromethyl-phenylethynyl)-pyridine,
3-Fluoro-5-(3-trifluoromethyl-phenylethynyl)-pyridine,
3-Bromo-5-(3-methoxyphenylethynyl)pyridine,
3-Methoxy-5-(3-trifluoromethyl-phenylethynyl)-pyridine,
5-(3-Acetylphenylethynyl)-nicotinonitrile,
5-(4-Fluoro-3-ethoxyphenylethynyl)-nicotinonitrile,
5-(3,4-difluorophenylethynyl)-pyridine-3-carbaldehyde O-methyloxime,
3-Methylsulfanyl-5-phenylethynyl-pyridine,
3-(3-Methoxy-phenylethynyl-5-methylsulfanyl-pyridine,
5-(3-Cyanomethyl-4-fluorophenylethynyl)-nicotinonitrile,
(5-Phenylethynyl-pyridin-3-yl)-carbamic acid tert-butyl ester,
3-(5-Aminopyridin-3-ylethynyl)-benzonitrile,
3-Chloro-5-(4-fluoro-3-methylphenylethynyl)-pyridine,
2-Fluoro-5-(5-methoxypyridin-3-ylethynyl)-benzonitrile
2-Fluoro-5-(5-methoxypyridin-3-ylethynyl)-phenylamine,
[5-(3-Cyanophenylethynyl)-pyridin-3-yl]-carbamic acid ethyl ester,
[5-(3-Cyanophenylethynyl)-pyridin-3-yl]-carbamic acid tert-butyl ester,
3-Chloro-5-(3-chloro-4-fluorophenylethynyl)-pyridine,
5-(5-Chloropyridin-3-ylethynyl)-2-fluorophenylamine,
5-(3-Trifluoromethylphenylethynyl)-pyridin-3-ylamine,
5-Phenylethynyl-pyridin-3-ylamine, Acetic acid 5-phenylethynyl-pyridin-3-yl-methyl ester and
3-Methoxymethyl-5-phenylethynyl-pyridine or a pharmaceutically acceptable salt
thereof, or an N-oxide thereof.

A most preferred compound of the present invention is selected from:

3-Methyl-5-phenylethynylpyridine, 5-(3-Cyano-4-fluorophenylethynyl)-nicotinonitrile,
3-(5-Trifluoromethylpyridin-3-ylethynyl)-benzonitrile,
5-(5-Chloropyridin-3-ylethynyl)-2-fluorobenzonitrile,
5-Phenylethynylpyridine-3-carbaldehydeoxime, 5-Phenylethynylpyridine-3-carbaldehyde
O-methyloxime, 3-(5-Phenylethynylpyridin-3-yl)acrylic acid methyl ester,
3-Bromo-5-phenylethynylpyridine, 5-(2-Chlorophenylethynyl)nicotinonitrile,
5-(3-Chlorophenylethynyl)nicotinonitrile, 5-(2-Fluorophenylethynyl)nicotinonitrile,
5-(3-Fluorophenylethynyl)nicotinonitrile, 5-(4-Fluorophenylethynyl)nicotinonitrile,
5-(3,5-Dimethylphenylethynyl)nicotinonitrile,
5-(2,5-Dimethylphenylethynyl)nicotinonitrile,
5-(3-Cyanophenylethynyl)nicotinonitrile, 5-(3-Methoxyphenylethynyl)nicotinonitrile,
5-(4-Methoxyphenylethynyl)nicotinonitrile, 3-Pyridin-3-ylethynylbenzonitrile,
3-Iodo-5-phenylethynylpyridine, 3-Chloro-5-phenylethynylpyridine,
3-Fluoro-5-phenylethynylpyridine, 5-(2-Methylphenylethynyl)nicotinonitrile,
5-(3-Methylphenylethynyl)nicotinonitrile, 3-(3-Chlorophenylethynyl)-pyridine,
3-(3-Methylphenylethynyl)-pyridine, 3-(5-Chloropyridin-3-ylethynyl)-benzonitrile,
3-Bromo-5-(3-chlorophenylethynyl)-pyridine, 3-Bromo-5-m-tolylethynylpyridine,
5-(3-Trifluoromethyl-phenylethynyl)-nicotinonitrile,
3-(5-Fluoropyridin-3-ylethynyl)-benzonitrile,
3-(5-Methylpyridin-3-ylethynyl)-benzonitrile,
3-(5-bromopyridin-3-ylethynyl)-benzonitrile,
5-(3,4-difluorophenylethynyl)-nicotinonitrile,
5-(3,5-difluorophenylethynyl)-nicotinonitrile,
3-(5-Methoxypyridin-3-ylethynyl)-benzonitrile,
(E)-5-[2-(3-Bromophenyl)-vinyl]-nicotinonitrile,
(E)-5-[2-(3-Cyanophenyl)-vinyl]-nicotinonitrile,
(E)-5-[2-(3-Chlorophenyl)-vinyl]-nicotinonitrile,
5-(3-Nitrophenylethynyl)-nicotinonitrile,
5-(3-Aminophenylethynyl)-nicotinonitrile,
5-(3-Chloro-4-fluorophenylethynyl)-nicotinonitrile,
5-(3-Hydroxyphenylethynyl)-nicotinonitrile,
5-(4-Fluoro-3-ethoxyphenylethynyl)-nicotinonitrile,
5-(3-Ethylphenylethynyl)-nicotinonitrile,
1-(5-Phenylethynyl-pyridin-3-yl)-ethanone O-methyloxime,
5-Phenylethynylpyridine-3-carbaldehyde O-methyloxime Z-isomer,
3-Bromo-5-(3-fluorophenylethynyl)-pyridine,
5-Phenylethynyl-pyridine-3-carbaldehyde O-methyloxime E-isomer,
3-(5-Formylpyridin-3-ylethynyl)-benzonitrile,
5-(3-Fluorophenylethynyl)-pyridine-3-carbaldehyde O-methyloxime,
3-[5-(Methoxyiminomethyl)-pyridin-3-ylethynyl]-benzonitrile,
5-(3-Methoxyphenylethynyl)-pyridine-3-carbaldehyde O-methyloxime E Isomer,
5-(3-Methoxyphenylethynyl)-pyridine-3-carbaldehyde O-methyloxime Z isomer,
5-(4-Fluorophenylethynyl)-pyridine-3-carbaldehyde O-methyloxime,
5-(4-Fluorophenylethynyl)-pyridine-3-carbaldehyde oxime,
5-(3,4-difluorophenylethynyl)-pyridine-3-carbaldehyde oxime,
5-(3-Trifluoromethoxy-phenylethynyl)-nicotinonitrile,
3-Methylsulfanyl-5-phenylethynyl-pyridine,
3-(3-Chloro-phenylethynyl)-5-methylsulfanyl-pyridine.
3-Methylsulfanyl-5-m-tolylethynyl-pyridine,
3-(5-Methylsulfanyl-pyridin-3-ylethynyl)-benzonitrile,
(5-Phenylethynyl-pyridin-3-yl)-carbamic acid ethyl ester,
5-(3-Amino-4-fluorophenylethynyl)-nicotinonitrile,
5-(4-Fluoro-3-nitrophenylethynyl)-nicotinonitrile and
1-(5-Phenylethynyl-pyridin-3-yl)-ethanone oxime, or a pharmaceutically acceptable salt thereof, or an N-oxide thereof.

Preparation of Compounds of the Invention

The starting materials and intermediates of compounds of the invention may be prepared by the application or adaptation of known methods, for example methods as described in the Examples or their chemical equivalents.

Compounds of the invention may be prepared by the application or adaptation of known methods, by which is meant methods used heretofore or described in the literature, for example those described by R. C. Larock in Comprehensive Organic Transformations, VCH publishers, 1989.

The invention also provides for a process of preparing a compound of formula 1 (or a pharmaceutically acceptable salt thereof, or an N-oxide thereof) which comprises:

(a) for a compound of formula 1 in which $R^1$ is 1,2-ethenediyl, reacting with a compound of formula II $$\text{(II)}$$

with a compound of formula Ar—CHCH$_2$ in a Heck coupling;

(b) for a compound of formula 1 in which $R^2$ is alkynyl, reacting with a compound of formula III $$\text{(III)}$$

in a Sonogashira coupling with a compound of formula Ar—I or Ar—Br in a suitable solvent;

whereafter, for any of the above procedures, when a pharmaceutically acceptable salt, or an N-oxide thereof, of a compound of formula 1 is required, it is obtained by reacting the basic form of such a compound of formula 1 with an acid affording a physiologically acceptable counterion, or, for a compound of formula 1 which bears an acidic moiety, reacting the acidic form of such a compound of formula 1 with a base which affords a pharmaceutically acceptable cation, or by any other conventional procedure; and wherein, unless more specifically described, the values of $R^1$, Ar or $R^2$ are as defined above.

The skilled artisan will appreciate that certain compounds of Formula 1 may contain at least one chiral center. The present invention contemplates all individual enantiomers, diastereomers or geometric (E/Z) isomers, as well as mixtures of the enantiomers, diastereomers and geometric (E/Z) isomers of said compounds including racemates. The single enantiomers, diastereomers or geometric (E/Z) isomers may be prepared beginning with chiral reagents or by stereoselective or stereospecific synthetic techniques. Alternatively, the single enantiomers, diastereomers or geometric (E/Z) isomers may be isolated from mixtures by standard chiral chromatographic or crystallization techniques.

It will be appreciated that compounds of the present invention may contain asymmetric centers. These asymmetric centers may independently be in either the R or the S configuration. It will be apparent to those skilled in the art that certain compounds of the invention may also exhibit geometrical isomerism. It is to be understood that the present invention includes individual geometrical isomers and stereoisomers and mixtures thereof, including racemic mixtures, of compounds of formula (1) hereinabove. Such isomers can be separated from their mixtures, by the application or adaptation of known methods, for example chromatographic techniques and recrystallisation techniques, or they are separately prepared from the appropriate isomers of their intermediates.

The compounds of the present invention can be prepared by a variety of procedures, some of which are illustrated in the Schemes below. It will be recognized by one of skill in the art that the individual steps in the following schemes may be varied to provide the compounds of Formula 1 The particular order of steps required to produce the compounds of Formula 1 is dependent upon the particular compound being synthesized, the starting compound, and the relative lability of the substituted moieties. Some substituents have been eliminated in the following schemes for the sake of clarity and are not intended to limit the teaching of the schemes in any way.

Schemes

The alkynyl or alkenyl compounds may be prepared as illustrated in Scheme 1 where Ar and $R^1$ are as previously defined. X is iodine, bromine, chlorine or trifluoromethanesulfonate. The products and intermediates are isolated after standard extractive and chromatographic techniques.

the alkyne (c) which is then reacted similarly in a Sonogashira coupling with a compound Ar—X, such as 1-fluoro-4 iodobenzene, to provide a $R^1$-substituted aryl-ethynylpyridine compound of formula (1a).

Additionally, an aryl-alkynyl compound (d) may be reacted directly with compound (a) using Sonogashira conditions, to give compound (1a). Also, a pyridine of formula (a) particularly with X as iodo or bromide may be treated with a compound of formula Ar—CH=CH$_2$ under palladium mediated Heck coupling conditions (Comp. Org. Syn, Vol 4, Ch 4.3; J. Med. Chem., 1997, 40, 4, 470-478) using a suitable solvent, such as N,N-dimethylformamide, to give a $R^1$-substituted aryl-ethenylpyridine (1b). Using similar palladium mediated Heck coupling conditions, compounds of formula (1b) may also be prepared by treating a vinylpyridine compound (e) with an aryl-X.

One of ordinary skill in the art will appreciate that a corresponding amide, sulfonamide or carbamate compounds of formula (1a) may be prepared directly from a corresponding compound of formula (1a) where $R^1$ is a carboxy or amino group or where Ar is substituted with an alkoxy-carbonyl or amino group. When Ar is substituted with an alkoxy-carbonyl group, it may be converted to a carboxylic acid group using known procedures in the literature, such as with lithium hydroxide in water and tetrahydrofuran. A compound of formula (1a) which bears a carboxy group may be treated with a coupling agent, such as 1-[3-(dimethylamino)propyl]-3-ethylcarbodiimide hydrochloride (EDCI) in a suitable solvent, such as N,N-dimethylformamide, and reacted with an amine, such as ammonia, methylamine or dimethylamine to give the corresponding amide. The amide products may be treated with Lawesson's Reagent, [2,4-bis(4-methoxyphenyl)-1,3-dithia-2,4-diphosphate-2,4-disulfide], to give the corresponding thioamide derivatives. When $R^1$ is a substituted Scheme 1

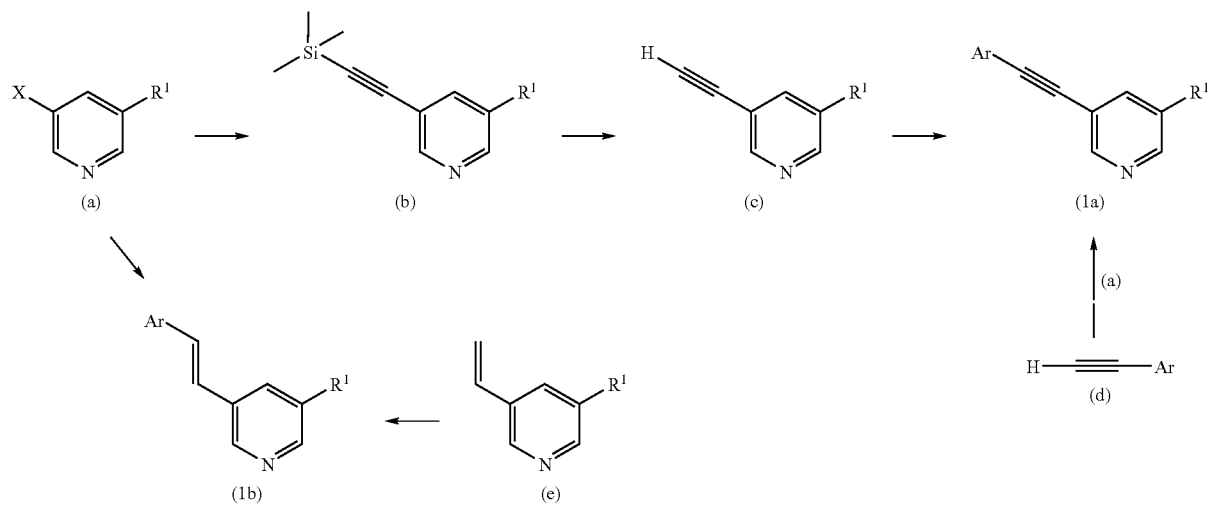

3-$R^1$-pyridine (a) is treated with trimethylsilylacetylene in a palladium catalyzed Sonogashira reaction (Synthesis 1977, 777; Comp. Org. Syn. Vol 3, Ch 2.4; OL 2000, 2, 1729; OL 2001, 3(20), 3111) in triethylamine in a sealed tube to give the silyl protected alkyne (b). The silyl protecting group is cleaved using standard conditions, such as with tetrabutylammonium fluoride or in alcoholic potassium carbonate, to give amino group, or when Ar is substituted with carboxamido, sulfoxamido or alkoxy-carbonylamino in a compound (1a), these various compounds may be prepared by treatment of the corresponding amine with an acid chloride, such as acetyl chloride, a sulfonyl chloride, such as methanesulfonyl chloride or an alkyl-chloroformate, such as ethyl chloroformate, using procedures known in the literature.

Similarly to provide a compound of formula (d) in which Ar is substituted with a carboxamido, sulfoxamido or alkoxycarbonylamino group, the nitrogen of an amino-aryl-halide may be substituted. Then the aryl-halide is converted to compound (d) in a manner similar to that of compound (c) using trimethylsilylacetylene. In a similar fashion, aryl-halides substituted with a methylamine group may be used to synthesize a compound (d) which may be converted to a compounds of formula (1a) where Ar is substituted with a substituted aminomethyl group.

A compound in which $R^1$ or a substituent on Ar is amino may be prepared from a corresponding nitro compound using a reduction method well-known in the literature, such as with iron in aqueous acetic acid. Similar chemistry may be used on the Ar group of compound (d) which can be then be coupled A compound of formula (1a) in which $R^1$ is $S-R^4$ may be prepared from compound (1a) where $R^1$ is bromine by treatment with a Grignard reagent, such as isopropylmagnesium chloride, in a suitable solvent like tetrahydrofuran, followed by the addition of a disulfide $R^4-S-S-R^4$ to give the $R^4$-sulfanyl compound. Oxidation of this compound with an oxidizing agent, such as 3-chloroperoxybenzoic acid, in a suitable solvent like dichloromethane, gives the $R^4$-sulfinyl or $R^4$-sulfonyl compounds depending on the specific conditions.

Compounds in which $R^1$ is the hydroxime, alkyl-oxime and acrylic-ester derivatives may be prepared as illustrated in Scheme 2 where $ArR^2$ of Formula 1 is as previously defined. The products and intermediates are isolated after standard extractive and chromatographic techniques.

Scheme 2

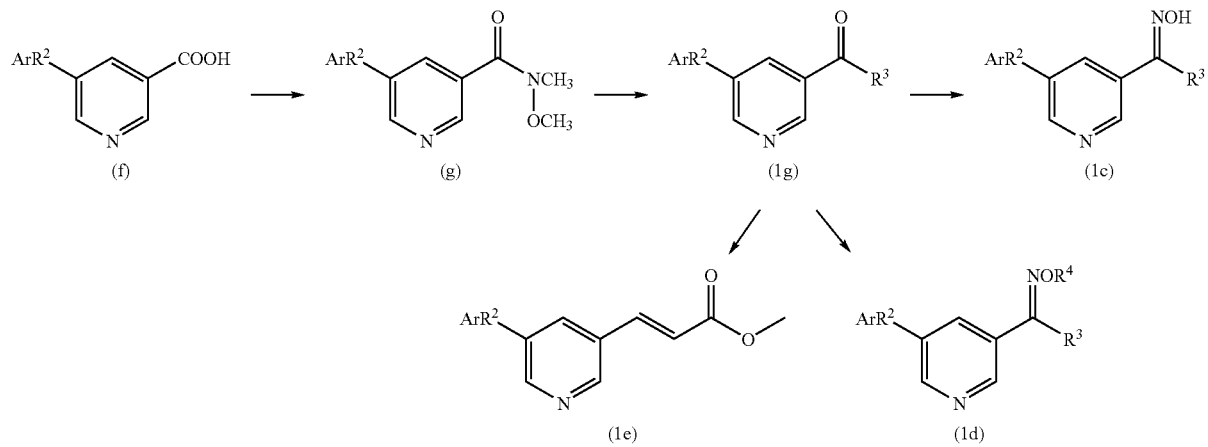

using Sonogashira conditions previously described to give compound (1a) with an amino group. Also, where compound (d) has an amino substituent on Ar, it may be directly reacted with compound (a) using previously described chemistry to give compound (1a). The aniline products may be further reacted to produce amides, sulfonamides and carbamates. A direct attachment of this group may be achieved when X is bromide using copper (I) iodide, potassium carbonate, N,N'-dimethylethylenediamine in 1,4-dioxane at elevated temperatures.

An aminomethyl or alkylated aminomethyl compound may be prepared from the corresponding compound where the Ar group in compound (1a) bears a formyl group. Treatment with an amine, such as methylamine, ethylamine, or propylamine, in the presence of a reducing agent such as sodium triacetoxyborohydride, in a suitable solvent like dichloroethane, gives the appropriately substituted aminomethyl compound. Alternatively the formyl group may be treated with ammonium hydroxide and iodine in a suitable solvent such as tetrahydrofuran to give the cyano group.

Aminomethyl compounds may also be prepared when the Ar group in compound (1a) is a substituted or unsubstituted benzyl alcohol. The alcohol can be converted to a suitable leaving group, such as chlorine, by reacting with thionyl chloride in an appropriate solvent such as dichloromethane. Treatment of the resultant chloride with amines, such as dimethyl amine or n-propylamine gives the corresponding substituted benzylamine. Alternatively the chloride can be treated with sodium cyanide in N,N-dimethylformamide to give the cyanomethyl compound.

The substituted nicotinic acid (f) is reacted with N,O-dimethylhydroxylamine hydrochloride with a coupling reagent, such as 1-[3-(dimethylamino)propyl]-3-ethylcarbodiimide hydrochloride (EDCI), in tetrahydronfuran in the presence of diisopropylethylamine to give the Weinreb amide (g). For example, treatment of (g) with a Grignard reagent, such as methylmagnesium chloride using conditions well-known in the literature, gives the pyridineethanone compound (1g) in which $R^3$ is methyl. Compound (g) may be reduced in a suitable solvent, such as toluene, at −78° C. with diisobutylaluminum hydride to give the pyridinecarboxaldehyde (1g) in which $R^3$ is hydrogen. This aldehyde is reacted with hydroxylamine hydrochloride or methoxylamine hydrochloride in a suitable solvent, such as ethanol, with a base like potassium carbonate to give the resultant compounds (1c) and (1d). Also the pyridinecarboxaldehyde (1g) is reacted with methyl(triphenylphosphoranylide)acetate in a suitable solvent, such as dichloromethane, to give compound (1e) as the pyridineacrylic acid methyl ester.

One of ordinary skill in the art will appreciate that further elaborate starting from the aldehyde (1g) may produce the methyl alcohol derivative after treatment with a reducing agent, such as sodium cyanoborohydride, in an appropriate solvent like methanol. This intermediate may then be reacted with an alkyl-halide, using a base like sodium hydride in a suitable solvent such as N,N-dimethylformamide, to give compound (1a) where $R^1$ is $CH_2-O-R^3$ Also the methyl alcohol compound derived from (1g) may be treated with methanesulfonyl chloride in the presence of a suitable base and solvent, like triethylamine and dichloromethane, to give the mesylate intermediate. Displacement of the leaving group with an amine, such as dimethylamine for example, gives compound (1a) where $R^1$ is $CH_2$—$N(CH_3)_2$.

One of ordinary skill in the art will appreciate that further elaboration of compound (1c) may result in additional compounds. Reduction of the hydroxylamine group, for example, with zinc dust in trifluoroaetic acid, gives the methylamine compound. If desired, this compound may then be acylated with an acyl-chloride, like ethylchloroformate, in the presence of a base, such as triethylamine, in a suitable solvent like dichloromethane, to give the carbamate compound.

The pyridine-N-oxide compound may be prepared as illustrated in Scheme 3 where $ArR^2$, and $R^1$ of Formula 1 are as previously defined. The products and intermediates are isolated after standard extractive and chromatographic techniques.

Scheme 3

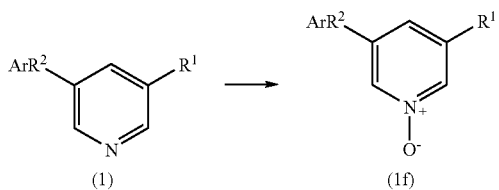

The substituted pyridine compound (1) is dissolved in a suitable solvent, such as dichloromethane, and oxidized using perrhenic acid to give the pyridine-N-oxide compound (1f).

Compounds of formula 1 may be prepared by conventional organic chemistry techniques and also by solid phase synthesis. Further, the compounds of the invention, their methods or preparation and their biological activity will appear more clearly from the examination of the following examples which are presented as an illustration only and are not to be considered as limiting the invention in its scope.

EXAMPLES

The following examples are provided to further describe the invention and are not to be construed as limitations thereof.

The abbreviations, symbols and terms used in the examples have the following meaning:
EI=electron impact
GC-MS=gas chromatography mass spectroscopy
HRMS=high resolution mass spectroscopy
LC-MS=liquid chromatography mass spectroscopy
MS (APCI)=mass spectroscopy atmospheric-pressure chemical ionization
MS (ES)=mass spectroscopy electrospray
NMR=nuclear magnetic resonance Preparation 1

3-Bromo-5-methylpyridine

Add cesium carbonate (1.38 g, 4.22 mmol), trimethylboroxine (0.2 mL, 1.47 mmol) and tetrakis(triphenylphosphine)palladium (0) (0.488 g, 0.42 mmol) to a solution of 3,5-dibromopyridine (1.0 g, 4.22 mmol) in 9:1 dioxane:water (10 mL) and stir under nitrogen at 110° C. for 16 h. Add more trimethylboroxine (0.2 mL, 1.47 mmol) and stir at 100° C. for an additional 16 h. Cool the reaction mixture to room temperature, filter through diatomaceous earth, and wash with ethyl acetate. Concentrate the filtrate and purify the residue by silica gel chromatography, eluting with 80:20 hexane:ethyl acetate, to give the title compound as a colorless oil (0.654 g, 90%).

$^1$H NMR (300 MHz, CDCl$_3$) δ 2.34 (s, 3 H), 7.66 (s, 1 H), 8.36 (s, 1 H), 8.49 (s, 1 H).
GC-MS (EI): m/z=171.0, 173.0 [M].

Preparation 2

N-Methoxy-N-methyl-5-phenylethynylnicotinamide

Add 1-[3-(dimethylamino)propyl]-3-ethylcarbodiimide hydrochloride (EDCI) (3.86 g, 20.2 mmol) and diisopropylethylamine (7.0 mL, 40.3 mmol) to a suspension of 5-phenylethynylnicotinic acid (3.0 g, 13.4 mmol) and N,O-dimethylhydroxylamine hydrochloride (1.97 g, 20.2 mmol) in tetrahydrofuran (100 mL) and stir at room temperature overnight. Concentrate the reaction mixture, dissolve the residue in ethyl acetate and wash sequentially with an aqueous solution of phosphate buffer (pH=7) and a saturated aqueous solution of sodium chloride. Dry the organic layer over magnesium sulfate, filter and concentrate. Purify the residue by silica gel chromatography, eluting with 50:50 ethyl acetate:hexanes, to give the title compound as a pale yellow solid (2.4 g, 67%).

$^1$H NMR (400 MHz, CDCl$_3$) δ 3.40 (s, 3H), 3.58 (s, 3H), 7.39-7.37 (m, 3H), 7.56-7.54 (m, 2H), 8.15 (d, J=2.4 Hz, 1H), 8.81 (d, J=2.0 Hz, 1H), 8.87 (d, J=1.6 Hz, 1H).
MS (ES): m/z=267 [M+H]$^+$.

Preparation 3

5-Trimethylsilanylethynyl-nicotinonitrile

Combine 5-bromonicotinonitrile (10.0 g, 53.0 mmol), bis(triphenylphosphine)palladium (II) dichloride (1.86 g, 2.65 mmol), copper (I) iodide (1.04 g, 5.46 mmol) and triethylamine (50 mL, 359 mmol) in a sealed tube under nitrogen and treat with (trimethylsilyl)acetylene (8.00 mL, 56.75 mmol). Stir the resultant black reaction mixture at 70° C. for 1.7 h and cool to room temperature. Dilute the reaction mixture with ethyl acetate and wash with a saturated aqueous solution of sodium chloride. Dry (sodium sulfate), filter and concentrate. Dissolve the residue in dichloromethane and filter through a pad of diatomaceous earth/silica gel. Wash with 80:20 dichloromethane:ethyl acetate. Concentrate the filtrate to give 11.6 g of the title compound as a brownish-tan solid. This material contains minor impurities, which do not have an adverse effect on subsequent chemistry (see PREPARATION 4). The crude material is purified by silica gel chromatography, eluting with 95:5 to 85:15 hexanes:ethyl acetate to give the title compound.

$^1$H NMR (400 MHz, CDCl$_3$) δ 0.31 (m, 9H), 8.03 (t, J=2.3 Hz, 1H), 8.81 (d, J=2.0 Hz, 1H), 8.87 (d, J=2.3 Hz, 1H); MS (ES): m/z 201.2 [M+H]$^+$; HRMS Calcd for C$_{11}$H$_{13}$N$_2$Si 201.0848 Found 201.0857; Anal Calcd for C$_{11}$H$_{12}$N$_2$Si: C, 65.96; H, 6.04; N, 13.98 Found: C, 65.72; H, 6.12; N, 13.91.

Preparation 4

5-Ethynyl-nicotinonitrile

Add a 1 M solution of tetrabutylammonium fluoride in tetrahydrofuran (50.0 mL, 50.0 mmol) to a suspension of 5-trimethylsilanylethynyl-nicotinonitrile (10.0 g, 50.0 mmol), (prepared as described in PREPARATION 3), in triethylamine (98 mL) at 0° C. After 5 min, dilute the reaction mixture with ethyl acetate and wash twice with water. Back-extract the combined aqueous washes twice with ethyl acetate. Wash the combined organic layers with a saturated aqueous solution of sodium chloride, dry (sodium sulfate), filter, and concentrate. Purify the residue by silica gel chromatography, eluting with a gradient from 98:2 to 90:10 dichloromethane:ethyl acetate, to give the title compound as a white crystalline solid (4.75 g, 74%).

$^1$H NMR (400 MHz, DMSO-$d_6$) δ 4.62 (s, 1H), 8.47 (t, J=2.0 Hz, 1H), 8.90 (d, J=2.2 Hz, 1H), 8.99 (d, J=1.8 Hz, 1H).

Preparation 5

3-Trimethylsilanylethynylbenzonitrile

Add trimethylsilylacetylene (3.4 mL, 24.0 mmol) to a mixture of bis(triphenylphosphine)palladium (II) dichloride (766 mg, 1.1 mmol), copper (I) iodide (418 mg, 2.2 mmol) and 3-iodobenzonitrile (5 g, 21.8 mmol) in triethylamine (20 mL). Upon addition of the trimethylsilylacetylene an exothermic reaction occurs and after about 4 min the reaction mixture solidifies. Cool the reaction mixture for about 15 min, dilute with ethyl acetate (100 mL), filter through fluted filter paper using ethyl acetate and concentrate. Dissolve the residue in ethyl acetate (200 mL) and wash sequentially with an aqueous solution of 0.1 N hydrochloric acid and a saturated aqueous solution of sodium chloride. Dry (sodium sulfate), filter and concentrate. Purify the residue by silica gel chromatography, eluting with 0:100 to 5:95 ethyl acetate:hexanes, to give the title compound as a tan solid (3.6 g, 83%).

$^1$H NMR (400 MHz, CDCl$_3$) δ 0.29 (s, 9H), 7.45 (t, J=8.0 Hz, 1H), 7.60-7.63 (m, 1H), 7.68-7.71 (m, 1H), 7.77-7.78 (m, 1H). LC-MS (ES): m/z=200.0 [M+H]$^+$.

Preparation 6

Trifluoromethanesulfonic acid 5-fluoropyridin-3-yl ester

Add triethylamine (0.65 mL, 4.64 mmol) and N-phenyltrifluoromethanesulfonimide (1.58 g, 4.43 mmol) to a solution of 5-fluoropyridin-3-ol (0.5 g, 4.42 mmol) in dichloromethane (11 mL) at 0° C. and stir under nitrogen for 1 h. Warm the reaction mixture to room temperature and stir overnight. Wash the reaction mixture sequentially with an aqueous solution of 1 M sodium hydroxide and water. Dry over sodium sulfate and concentrate the organic layer to obtain the title compound as a volatile oil (0.568 g, 52%).

$^1$H NMR (300 MHz, CDCl$_3$) δ 7.43-7.47 (dt, J=8.0 Hz, 2.4 Hz, 1 H), 8.47 (s, 1 H), 8.57 (t, J=2.0 Hz, 1 H). GC-MS (EI): m/z=245.0 [M].

Preparation 7

3-Chloro-5-trifluoromethylpyridine

Add zinc dust (1.18 g) to a suspension of 2,3-dichloro-5-trifluoromethyl-pyridine (2.0 g, 9.30 mmol) in 80:20 water and acetic acid (5 mL) and stir at 90° C. for 1 h. Add more zinc dust (1g) and stir at 90° C. for an additional 15 min. Cool the reaction mixture to room temperature, filter, and wash with dichloromethane. Carefully concentrate and purify the residue by silica gel chromatography, eluting with 100:0 to 0:100 hexane:dichloromethane, to obtain the title compound as a volatile oil (0.120g, 7%).

$^1$H NMR (300 MHz, CDCl$_3$) δ 7.93 (s, 1 H), 8.78 (s, 2 H). GC-MS (EI): m/z=181.0, 183.0 [M].

Preparation 8

3-Ethynylbenzonitrile

Add potassium carbonate (0.138 g, 1 mmol) to a solution of 3-trimethylsilanylethynylbenzonitrile from PREPARATION 5 (2.0 g, 10.1 mmol) in methanol (50 mL). Stir the mixture at room temperature for 20 min and add a 10% aqueous hydrochloric acid solution (4 mL). Concentrate to a reduced volume, add diethyl ether and water and separate the phases. Wash once the aqueous phase with diethyl ether. Combine the organic phases, dry over sodium sulfate and concentrate to obtain the title compound as a solid (1.17 g, 92%).

$^1$H NMR (300 MHz, CDCl$_3$) δ 3.19 (s, 1H), 7.45 (t, J=8.0 Hz, 1H), 7.63 (dt, J=6.5 and 1.2 Hz, 1H), 7.70 (dt, J=7.7 and 1.2 Hz, 1H), 7.76 (s, 1H). GC-MS (EI): m/z=127 [M]$^+$.

Preparation 9

3-Bromo-5-methoxypyridine

Add sodium (0.583 g, 25 mmol) to methanol (10 mL) at 0° C. Stir the mixture at 0° C. until obtain a solution and concentrate. Add N,N-dimethylformamide (25 mL) and add 3,5-dibromopyridine (3.0 g, 12.66 mmol). Stir at 70° C. for 4 h. Cool to room temperature and add water. Extract twice with diethyl ether. Combine the organic phases, wash once with water, dry over sodium sulfate and concentrate. Purify the residue by silica gel chromatography, eluting with a gradient of 100:0 to 50:50 hexanes:ethyl acetate, to give the title compound as a solid (1.37 g, 57%).

LC-MS (ES): m/z=187.9, 190.0 [M+H]$^+$.

Preparation 10

3-Ethynyl-5-methoxypyridine (a) 3-Methoxy-5-trimethylsilanylethynyl-pyridine
Add (trimethylsilyl)acetylene (1.3 mL, 9.45 mmol) and bis(triphenylphosphine)palladium (II) dichloride (0.102 g, 0.15 mmol) to a mixture of 3-bromo-5-methoxypyridine from PREPARATION 9 (1.366 g, 7.26 mmol), copper (I) iodide (0.055 g, 0.29 mmol) and triethylamine (4.1 mL, 29.04 mmol) in ethyl acetate (7.5 mL) in a sealed tube. Stir the resultant reaction mixture at 75° C. for 20 h and cool to room temperature. Dilute the reaction mixture with ethyl acetate and filter through a pad of diatomaceous earth. Wash with ethyl acetate and concentrate the filtrate to give the title compound as a solid which is used without further purification (1.48 g, 100%).

LC-MS (ES): m/z=206.2 [M+H]$^+$.
(b) 3-Ethynyl-5-methoxypyridine
Prepare essentially as described in PREPARATION 8 using 3-methoxy-5-trimethylsilanylethynyl-pyridine (1.48 g, 7.26 mmol) to give the title compound (0.90 g, 93%).

$^1$H NMR (300 MHz, CDCl$_3$) δ 3.85 (s, 1H), 7.27 (s, 1H), 8.28 (d, J=2.8 Hz, 1H), 8.32 (d, J=1.6 Hz, 1H). GC-MS (EI): m/z=133 [M]$^+$.

Preparation 11

1-Ethynyl-3-nitrobenzene (a) Trimethyl-(3-nitrophenylethynyl)-silane
Prepare essentially as described in PREPARATION 10 using 1-bromo-3-nitrobenzene (2.0 g, 10.0 mmol). Submit the residue directly to the next reaction.

LC-MS (ES): m/z=207.0, 189.1 [M-O$_2$]$^+$, 174.1 [M-NO$_2$]$^+$.

(b) 1-Ethynyl-3-nitrobenzene

Prepare essentially as described in PREPARATION 8 using trimethyl-(3-nitrophenylethynyl)-silane to give the title compound (0.644 g, 44%, two steps).

$^1$H NMR (300 MHz, CDCl$_3$) δ 3.22 (s, 1H), 7.52 (t, J=8.0 Hz, 1 H), 7.78 (d, J=7.5 Hz, 1H), 8.19 (dd, J=8.3 and 1.2 Hz, 1H), 8.32 (s, 1H). GCMS (EI): m/z=147.1 [M]$^+$.

Preparation 12

1-Chloro-3-ethynylbenzene 4-(3-Chloro-phenyl)-2-methylbut-3-yn-2-ol

Add triethylamine (75 mL), 1-bromo-3-chlorobenzene (24.1 g, 0.126 mol), and 2-methylbut-3-yn-2-ol (15 mL, 0.152 mol) to a degassed mixture of bis(triphenylphosphine) palladium (II) dichloride (49 mg, 7.1 10$^{-5}$ mol) and copper (I) iodide (2.4 mg, 1.26 10$^{-5}$ mol). Stir at 90° C. for 72 h. Cool the reaction mixture to room temperature. Filter, concentrate and dissolve in ethyl acetate. Wash with water and dry the organic phase over sodium sulfate. Filter, concentrate and purify the residue by silica gel chromatography, eluting with hexane: ethyl acetate 6:1, to give the title compound (23 g, 94%).

1-Chloro-3-ethynylbenzene

Add dry toluene to a degassed mixture of 4-(3-chlorophenyl)-2-methylbut-3-yn-2-ol (21.1 g, 0.109 mol), potassium carbonate (45 g, 0.326 mol) and 18-crown-6 (6.89 g, 0.026 mol). Stir at 90° C. for 36 h. Cool the reaction mixture to room temperature, filter and wash with toluene. Concentrate and purify the residue by silica gel chromatography, eluting with 18:1 o 13:1 hexanes:ethyl acetate, to give the title compound (9.85 g, 66%).

$^1$H NMR (300 MHz, CH$_3$OH-d4) δ 3.63 (s, 1H), 7.48-7.32 (m, 4H).

Preparation 13

1-Ethynyl-3-trifluoromethylbenzene (a) Trimethyl-(3-trifluoromethylphenylethynyl)-silane Add copper (I) iodide (48.2 mg, 0.25 mmol), bis(triphenylphosphine)palladium (II) dichloride (155.8 m g, 0.22 mmol) and triethylamine (2.51 mL, 17.8 mmol), to a solution of 1-bromo-3-trifluoromethylbenzene (0.62 mL, 4.44 mmol) and trimethylsilylacetylene (0.81 mL, 5.78 mmol), in ethyl acetate (4 mL). Stir at 50° C. for 18h. Cool the reaction mixture to room temperature, concentrate and purify the residue by silica gel chromatography, eluting with hexanes, to give the title compound (1.1 g, 100%).

$^1$H NMR (300 MHz, CDCl$_3$) δ 0.27 (s, 9H), 7.42 (t, J=7.8 Hz, 1H), 7.56 (d, J=7.8 Hz, 1H), 7.62 (d, J=7.8 Hz, 1H), 7.73 (s, 1H).

(b) 1-Ethynyl-3-trifluoromethylbenzene

Add potassium carbonate (307 mg, 2.22 mmol) to a solution of trimethyl-(3-trifluoromethylphenylethynyl)-silane (1.07 g, 4.42 mmol) in ethanol (15 mL). Stir at room temperature for 16 h. Neutralized with 10% aqueous hydrochloric acid solution. Add water and extract the product with hexanes. Evaporate hexanes slowly in a cool water bath (<15° C.) to give the title compound (580 mg, 77%).

$^1$H NMR (300 MHz, CDCl$_3$) δ 3.15 (s, 1H), 7.45 (t, J=7.7 Hz, 1H), 7.60 (d, J=7.7 Hz, 1H), 7.66 (d, J=7.7 Hz, 1H), 7.75 (s, 1H).

Preparation 14

4-Ethynyl-1,2-difluorobenzene (a) (3,4-Difluorophenylethynyl)-trimethylsilane

Add copper (I) iodide (109.4 mg, 0.57 mmol), bis(triphenylphosphine)palladium (II) dichloride (365 mg, 0.52 mmol) and triethylamine (5.88 mL, 41.6 mmol), to a solution of 4-bromo-1,2-difluorobenzene (1.17 mL, 10.4 mmol) and trimethylsilylacetylene (1.89 mL, 13.5 mmol), in ethyl acetate (8 mL). Stir at 50° C. for 18h. Cool to room temperature, concentrate and purify the residue by silica gel chromatography, eluting with hexanes, to give the title compound (2.20 g, 100%).

$^1$H NMR (300 MHz, CDCl$_3$) δ 0.25 (s, 9H), 7.12-7.03 (m, 1H), 7.30-7.17 (m, 2H).

(b) 4-Ethynyl-1,2-difluorobenzene

Add potassium carbonate (719 mg, 5.2 mmol) to a solution of (3,4-difluorophenylethynyl)-trimethylsilane (2.20 g, 10.4 mmol) in ethanol (30 mL). Stir at room temperature for 16 h. Neutralize with 10% aqueous hydrochloric acid. Add water and extract the product with hexanes. Concentrate hexanes slowly in a cooled water bath (~10° C.) to give the title compound (1.10 g, 76%).

$^1$H NMR (300 MHz, CDCl$_3$) δ 3.07 (s, 1H), 7.15-7.07 (m, 1H), 7.33-7.20 (m, 2H).

Preparation 15

2-Fluoro-5-iodophenol

Add a 2 M solution of n-butyllithium in hexanes (63 mL, 157.5 mmol) to a −20° C. solution of 2,2,6,6-tetramethylpiperidine (28 mL, 165 mmol) in tetrahydrofuran (400 μL). Cool to −78° C. and add 1-iodo-4-fluorobenzene (17.3 mL, 150 mmol) dropwise over 10 min. Stir the reaction mixture at −78° C. for 3 h and add triisopropylborate (40 mL, 172.5 mmol) dropwise over 20 min. Stir for another 30 min and warm the reaction to 40° C. and add of 5 N hydrochloric acid (75 mL). Partition the reaction mixture between diethyl ether (500 mL) and add 1 N hydrochloric acid (500 mL). Separate the organic layer and extract with 2 N sodium hydroxide (400 mL). Make the aqueous layer slightly acidic (pH ~5-6) by dropwise addition of 5 N hydrochloric acid and collect the resulting white precipitate by filtration. Dry the precipitate overnight under vacuum to provide 2-fluoro-5-iodophenylboronic acid as a white solid, which is used directly without further purification (39g, 98%).

To a cooled solution of 2-fluoro-5-iodophenylboronic acid in tetrahydrofuran (200 mL) at 0° C. add an aqueous solution of 30% hydrogen peroxide (9.92 mL, 103 mmol) dropwise, stir 10 min, and add an aqueous 4 N solution of sodium hydroxide (1.78 mL, 7.12 mmol). Warm the reaction to room temperature and stir overnight. Add manganese dioxide (250 mg) to the reaction, stir 90 min and filter through fluted filter paper. Concentrate and partition the residue between diethyl ether and water. Separate the layers and sequentially wash the organic layer with water and an aqueous saturated solution of sodium chloride. Dry (sodium sulfate), filter and concentrate. Purify the resulting tan oil by silica gel chromatography, eluting with a gradient of 0:100 to 30:70 ethyl acetate:hexanes, to give the title compound as a yellow waxy solid (18.1 g, 65%).

$^1$H NMR (400 MHz, DMSO-d$_6$) δ 6.93 (dd, J=8 Hz, 11 Hz, 1H), 7.10 (m, 1H), 7.24 (dd, J=8.5 Hz, 2.4 Hz, 1H), 10.21 (s, 1H); LC-MS (ES): m/z=238.3 [M+H]$^+$.

Preparation 16

5-Trimethylsilanylethynyl-nicotinic acid ethyl ester

A solution of ethyl-5-bromonicotinate (30 g, 130.40 mmol), triethylamine (78 mL) and ethyl acetate (130 mL) is degassed for 15 min. Add trimethylsilylacetylene (88.46 mL, 625.92 mmol), bis(triphenylphosphine)palladium (II) dichloride (4.57 g, 6.52 mmol) and copper (I) iodide (0.25 g, 1.30 mmol) and stir at 50° C. under-nitrogen for 16 h. Cool to room temperature, filter through diatomaceous earth, wash with ethyl acetate, and concentrate. Purify the residue by silica gel chromatography, eluting with 10:1 hexanes:ethyl acetate, to give the title compound (27.7 g, 86%).

$^1$H NMR (300 MHz, CDCl$_3$) δ 0.20 (s, 9 H), 1.34 (t, J=7.1 Hz, 3 H), 4.34 (q, J=7.1 Hz, 2 H), 8.25 (t, J=2.0 Hz, 1 H), 8.73 (d, J=2.0 Hz, 1 H), 9.03 (d, J=2.0 Hz, 1 H); MS (ES): m/z=248 [M+H]$^+$.

Preparation 17

5-(3-Fluorophenylethynyl)-nicotinic acid ethyl ester

Add a 1 M solution of tetrabutylammonium fluoride in tetrahydrofuran (0.88 g, 3.38 mmol) to a mixture of 3-iodofluorobenzene (0.50 g, 2.25 mmol), 5-trimethylsilanylethynyl-nicotinic acid ethyl ester (0.84 g, 3.38 mmol), (prepared essentially as described in PREPARATION 16), bis(triphenylphosphine)palladium (II) dichloride (0.03 g, 0.05 mmol) and copper (I) iodide (0.02 g, 0.09 mmol) at −780C. Warm to room temperature, stir overnight and dilute the mixture with ethyl acetate and an aqueous saturated solution of ammonium chloride. Separate the organic layer; dry (magnesium sulfate), filter and concentrate. Purify the resulting residue by silica gel chromatography, eluting with 2.5:45:52.5 ethyl acetate:chloroform:hexanes, to give the title compound as a pale yellow solid (0.46 g, 80%).

$^1$H NMR (400 MHz, CDCl$_3$) δ 1.43 (t, J=7.3 Hz, 3 H), 4.44 (q, J=7.1 Hz, 2 H), 7.10 (m, 1 H), 7.25 (m, 1 H), 7.35 (m, 2 H), 8.41 (t, J=2.0 Hz, 1H), 8.90 (s, 1H), 9.16 (s, 1 H);

MS (ES): m/z=270 [M+H]$^+$.

Preparation 18

5-(3-Fluorophenylethynyl)-N-methoxy-N-methylnicotinamide

Sequentially add a 2 M solution of trimethylaluminum in toluene (0.64 g, 8.91 mmol) and 5-(3-fluorophenylethynyl)-nicotinic acid ethyl ester (0.24 g, 0.89 mmol), (prepared essentially as described in PREPARATION 17), to a solution of N,O-dimethylhydroxylamine (0.435 g, 4.46 mmol) in anhydrous toluene (4.0 mL) at 0° C. After 30 min, warm to room temperature and stir overnight. Dilute the reaction with ethyl acetate and an aqueous saturated solution of Rochelle salt (potassium sodium tartrate) and stir vigorously for 1 h. Separate the organic layer; dry (magnesium sulfate), filter and concentrate. Purify the resulting residue by silica gel chromatography, eluting with a linear gradient of 100:0 to 60:40 tetrahydrofuran:hexanes, to give the title compound as a pale yellow oil (0.084 g, 33%).

$^1$H NMR (400 MHz, CDCl$_3$) δ 3.41 (s, 3H), 3.58 (s, 3H), 7.27-7.22 (m, 2H), 7.38-7.31 (m, 2H), 8.15 (t, J=2.0 Hz, 1H), 8.82 (s, 1H), 8.89 (s, 1H); MS (ES): m/z=285 [M+H]$^+$.

Preparation 19

3-(5-Bromopyridin-3-ylethynyl)-benzonitrile

Prepare essentially as described in PREPARATION 17 using a 1 M solution of tetrabutylammonium fluoride in tetrahydrofuran (4.2 mL, 4.2 mmol), 3,5-dibromopyridine (1.00 g, 4.2 mmol), 3-trimethylsilanylethynylbenzonitrile (0.84 g, 4.2 mmol), (prepared as described in PREPARATION 5), bis(triphenylphosphine)palladium (II) dichloride (0.06 g, 0.08 mmol) and copper (I) iodide (0.03 g, 0.17 mmol) to give the title compound (0.45 g, 39%).

$^1$H NMR (400 MHz, CDCl$_3$) δ 7.51 (t, J=7.9 Hz, 1H), 7.66 (dt, J=4.6 Hz, 2.6 Hz, 1H), 7.75 (dt, J=4.5 Hz, 2.6 Hz, 1H), 7.82 (t, J=1.3 Hz, 1H), 7.98 (t, J=2.0 Hz, 1H), 8.71-8.63 (m, 2H); MS (ES): m/z=284 [M+H]$^+$.

Preparation 20

3-Bromo-5-(3-methoxyphenylethynyl)-pyridine

Add 1-ethynyl-3-methoxybenzene (0.56 g, 4.22 mmol) to a mixture of 3,5-dibromopyridine (1.00 g, 4.22 mmol), bis (triphenylphosphine)palladium (II) dichloride (0.06 g, 0.08 mmol) and copper (I) iodide (0.03 g, 0.17 mmol) in triethylamine (8 mL) and heat at 70° C. for 2 h. Cool to room temperature, dilute with ethyl acetate and an aqueous saturated solution of ammonium chloride, and separate the layers. Wash the organic layer with an aqueous saturated solution of sodium chloride, dry (magnesium sulfate), filter and concentrate. Purify the resulting residue by silica gel chromatography, eluting with 2.5% ethanol in 50:50 chloroform/hexanes, to give the title compound (0.86 g, 71%).

$^1$H NMR (400 MHz, CDCl$_3$) δ 3.83 (s, 3H), 7.06 (m, 1H), 7.13 (dt, J=4.5 Hz, 2.5 Hz, 1H), 7.31-7.25 (m, 2H), 7.97 (t, J=2.0 Hz, 1H), 8.62 (s, 1H), 8.67 (s, 1H); MS (ES): m/z=289 [M+H]$^+$.

Preparation 21

3-Bromo-5-iodopyridine

Sequentially slowly add a 2 M solution of isopropylmagnesium chloride in tetrahydrofuran (0.25 g, 2.41 mmol) and a solution of iodine (0.62 g, 2.41 mmol) in anhydrous tetrahydrofuran to a solution of 3,5-dibromopyridine (0.52 g, 2.19 mmol) in anhydrous tetrahydrofuran (4 mL) at −100° C. with the internal temperature below −5° C. Stir approximately 5 min and dilute the reaction with ethyl acetate and an aqueous saturated solution of sodium hydrogen sulfite solution. Separate the organic layer and dry (magnesium sulfate), filter and concentrate to give the title compound (4.85 g, 98%), which is used directly with out further purification.

$^1$H NMR (400 MHz, CDCl$_3$) δ 7.54-7.51 (m, 1H), 8.26 (s, 1H), 8.42 (s, 1H); MS (ES): m/z=284 [M+H]$^+$.

Preparation 22

3-Bromo-5-[(trimethylsilanyl)-ethynyl]-pyridine

Add trimethylsilylacetylene (54.6 mL, 389.4 mmol) to a stirred mixture of 3-bromo-5-iodopyridine (100 g, 354 mmol) in triethylamine (800 mL) and acetonitrile (800 mL). Purge the system with nitrogen and add bis(triphenylphosphine)palladium(II) dichloride (3.54 mmol, 2.48 g) and stir for 16 h. Concentrate and suspend the residue in 1800 mL of hexanes. Stir for 2 h, filter and concentrate to give the title compound as a brown solid (92g, 99%).
¹H NMR (300 MHz, CDCl₃) δ 8.54 (m, 2 H), 7.58 (m, 1 H), 0.22 (s, 9 H); LC-MS (ES): m/z=254, 256 [M+H]⁺.

Preparation 23

3-Bromo-5-ethynylpyridine

Add a 1 M aqueous solution of potassium hydroxide (369.7 mmol, 370 mL) to a stirred solution of 3-bromo-5-trimethylsilanylethynyl-pyridine (85.4 g, 336.1 mmol), (prepared essentially as described in PREPARATION 22), in 850 mL of methanol at 15° C. Stir at room temperature for 2 h and concentrate. Dissolve the residue in 800 mL of dichloromethane, sequentially wash with water (160 mL) and an aqueous saturated solution of sodium chloride (160 mL), dry (magnesium sulfate) and concentrate with only slight heating to give the title compound as a pale volatile brown solid (53.84 g, 88%).
¹H NMR (300 MHz, CDCl₃) δ 8.60 (m, 2H), 7.90 (s, 1H), 3.25 (s, 1H); MS (ES): LC-MS (ES): m/z=181, 183 [M+H]⁺.

Preparation 24

3-Bromo-5-(4-fluorophenylethynyl)-pyridine

Sequentially add triethylamine (161 mL, 1156 mmol), bis(triphenylphosphine)palladium(II) dichloride (2 g, 2.89 mmol) and copper (I) iodide (1.1 g, 5.78 mmol) to a solution of 3-bromo-5-ethynylpyridine (52.7 g, 289 mmol), (prepared essentially as described in PREPARATION 23), and 1-fluoro-4-iodobenzene (58.4 g, 262.7 mmol) in acetonitrile (1000 mL). Purge the system with nitrogen and heat the reaction mixture at 50° C. for 16 h. Concentrate, dissolve the residue in 10:1 hexanes:dichloromethane (1000 mL), filter and concentrate. Stir the residue in 150 mL of hexanes at room temperature for 30 min to produce a slurry. Cool the slurry at 0° C. and filter to give the title compound. From the filtrate, a second crop of the title compound can be isolated (45.5 g, 63%).
¹H NMR (300 MHz, CDCl₃) δ 8.65 (d, J=1.9 Hz, 1H), 8.61 (d, J=2.9 Hz, 1H), 7.95 (t, J=2.3 Hz, 1H), 7.52 (m, 1H), 7.08 (t, J=8.9 Hz, 1H); LC-MS (ES): m/z=275, 277 [M+H]⁺.

Preparation 25

Trifluoromethanesulfonic acid 5-chloropyridin-3-yl ester

Sequentially add triethylamine (1.1 mL, 8.1 mmol) and N-phenylbistrifluoromethanesulfonimide (2.76 g, 7.72 mmol) to a suspension of 5-chloropyridin-3-ol (1.0 g, 7.72 mmol) in dichloromethane (20 mL) at 0° C. under nitrogen and stir for 1 h. Warm to room temperature and stir for 1.5 h. Wash the reaction mixture with 1 N sodium hydroxide (100 mL) followed by water (100 mL). Dry (sodium sulfate), filter, and concentrate to give the title compound as a yellow oil (1.95 g, 97%).
¹H NMR (300 MHz, CDCl₃) δ 7.68-7.69 (m, 1H), 8.51 (d, J=2.4 Hz, 1H), 8.64 (d, J=1.9 Hz, 1H); MS (APCI): m/z=262 [M+H]⁺.

Preparation 26

3-Chloro-5-trimethylsilanylethynyl-pyridine

Sequentially add triethylamine (16 mL, 114 mmol), trimethylsilyl acetylene (4.5 mL, 34.1 mmol), bis(triphenylphosphine)palladium (II) dichloride (0.538 g, 0.77 mmol), and copper (I) iodide (270 mg, 1.42 mmol) to a solution of trifluoromethanesulfonic acid 5-chloropyridin-3-yl ester (7.4 g, 28.4 mmol), (prepared as described in PREPARATION 25), in ethyl acetate (25 mL) under nitrogen. Heat at 60° C. for 1 h, cool to room temperature, stir for 12 h, filter through diatomaceous earth and wash with diethyl ether. Concentrate and purify the residue by silica gel chromatography, eluting with 20:80 ethyl acetate:hexanes, to give the title compound as an orange oil (5.51 g, 92%).
¹H NMR (300 MHz, CDCl₃) δ 0.07 (s, 9H), 7.54-7.55 (m, 1H), 8.30 (d, J=2.3 Hz, 1H), 8.36 (d, J=1.7 Hz, 1H); MS (APCI): m/z=210 [M+H]⁺.

Preparation 27

3-Chloro-5-ethynylpyridine

Add potassium carbonate (4.35 g, 31.5 mmol) to a solution of 3-chloro-5-trimethylsilanylethynyl-pyridine (5.51 g, 26.3 mmol), (prepared as described in PREPARATION 26), in methanol (120 mL) and stir for 2 h. Concentrate, add water (150 mL), and extract with diethyl ether (2×100 mL). Wash the organic phase with an aqueous saturated solution of sodium chloride (100 mL), dry (sodium sulfate), filter, and concentrate. Purify the residue by silica gel chromatography, eluting with 20:80 ethyl acetate:hexanes to give the title compound as a pale yellow solid (1.9 g, 52%).
¹H NMR (300 MHz, CDCl₃) δ 3.26 (s, 1H), 7.76-7.77 (m, 1H), 8.54 (d, J=2.3 Hz, 1H), 8.59 (d, J=1.7 Hz, 1H); MS (APCI): m/z=138 [M+H]⁺.

Preparation 28

1-Ethynyl-3-trifluoromethoxybenzene (a) Trimethyl-(3-trifluoromethoxyphenylethynyl)-silane
Add copper (I) iodide (45.0 mg, 0.24 mmol), bis(triphenylphosphine)palladium (II) dichloride (147.4 m g, 0.21 mmol) and triethylamine (2.37 mL, 16.8 mmol), to a solution of 1-bromo-3-trifluoromethoxybenzene (0.62 mL, 4.15 mmol) and trimethylsilylacetylene (0.78 mL, 5.4 mmol), in ethyl acetate (4 mL) and stir at 50° C. for 18h. Cool the reaction mixture to room temperature, concentrate and purify by silica gel chromatography, eluting with hexanes to give the title compound (1.07 g, 100%).
¹H NMR (300 MHz, CDCl₃) δ 0.26 (s, 9H), 7.16 (br d, J=7.7 Hz, 1H), 7.31 (m, 2H), 7.37 (br d, J=7.7 Hz, 1H).
(b) 1-Ethynyl-3-trifluoromethoxybenzene
Add potassium carbonate (257 mg, 1.86 mmol) to a solution of trimethyl-(3-trifluoromethoxyphenylethynyl)-silane (960 mg, 3.72 mmol) in ethanol (15 mL) and stir for 16 h. Add a 10% aqueous solution of hydrochloric acid to neutralize the reaction mixture and then partition between water and hexanes. Separate the organic layer and concentrate with cooling to give the title compound (571.4 mg, 83%).
¹H NMR (300 MHz, CDCl₃) δ 3.14 (s, 1H), 7.21 (br d, J=7.7 Hz, 1H), 7.35 (m, 2H), 7.42 (br d, J=7.7 Hz, 1H).

Preparation 29

3-Bromo-5-methylsulfanylpyridine

Add 1,8-diazabicyclo[5.4.0]undec-7-ene (0.8 mL, 5.28 mmol) to a solution of 3-bromo-5-iodopyridine (500 mg, 1.76 mmol), (prepared as described in PREPARATION 21), sodium methanethiolate (370 mg, 5.28 mmol) and copper bromide (50.2 mg, 0.35 mmol) in toluene (3 mL). Stir in a sealed flask at 90° C. overnight and then partition between water and ethyl acetate. Separate the organic layer and wash with an aqueous saturated solution of sodium chloride. Dry (magnesium sulfate), filter and concentrate. Purify the residue by silica gel chromatography, eluting with hexane:ethyl acetate, to give the title compound (250 mg, 70%).

$^1$H NMR (300 MHz, CDCl$_3$) δ 2.51 (s, 3H), 7.67 (br s, 1H), 8.39 (br s, 1H), 8.41 (br s, 1H).

Preparation 30

N-(5-Bromo-2-fluorobenzyl)acetamide

Add acetyl chloride (0.18 mL, 2.49 mmol) to a mixture of 5-bromo-2-fluorobenzylamine hydrochloride (500 mg, 2.08 mmol) in dichloromethane (8 mL) and diisopropylethylamine (0.90 mL, 5.20 mmol) and stir 3 h. Dilute with diethyl ether and separate the layers. Wash the organic layer twice with 1 N hydrochloric acid and once with an aqueous saturated solution of sodium chloride. Dry (sodium sulfate), filter, and concentrate to give the title compound as a white crystalline solid (490 mg, 96%).

$^1$H NMR (400 MHz, DMSO-d$_6$) δ 1.83 (s, 3H), 4.22 (d, J=5.7 Hz, 2H), 7.13 (dd, J=9.7 Hz, J=8.4 Hz, 1H), 7.47-7.41 (m, 2H), 8.32 (t, J=5.3 Hz, 1H).

Preparation 31

N-(2-Fluoro-5-trimethylsilanylethynylbenzyl)-acetamide

Combine N-(5-bromo-2-fluorobenzyl)acetamide, (prepared as described in PREPARATION 30), (370 mg, 1.50 mmol, zinc(II) bromide (588 mg, 2.25 mmol), and triethylamine (1.00 mL, 7.20 mmol) in tetrahydrofuran (3.7 mL). After stirring for 5 min, add trimethylsilylacetylene (0.53 mL, 3.76 mmol) and tetrakis(triphenylphosphine)palladium (0) (87 mg, 0.075 mmol). Heat the mixture in a sealed tube at 60° C. overnight. Cool the reaction to room temperature and filter through diatomaceous earth. Concentrate the filtrate and purify the residue by silica gel chromatography, eluting with a gradient from 75:25 to 65:35 with a solution of (1:1 hexanes and dichloromethane):ethyl acetate to give the title compound as a yellow oil which crystallizes upon standing (309 mg, 78%).

$^1$H NMR (400 MHz, DMSO-d6) δ 0.18 (s, 9H), 1.83 (s, 3H), 4.21 (d, J=6.2 Hz, 2H), 7.16-7.12 (m, 1H), 7.37-7.34 (m, 2H), 8.30 (t, J=5.5 Hz, 1H).

Preparation 32

5-(3-Chloromethyl-4-fluorophenylethynyl)-nicotinonitrile

Add thionyl chloride (0.59 mL, 8.07 mmol) to a solution of 5-(4-fluoro-3-hydroxymethyl-phenylethynyl)-nicotinonitrile (1.85 g, 7.33 mmol), (prepared as described in EXAMPLE 142). After 3 h add an additional 0.2 mL of thionyl chloride and stir for another 1 h. Dilute the reaction mixture with ethyl acetate and wash with an aqueous saturated solution of sodium bicarbonate and an aqueous saturated solution of sodium chloride. Dry (sodium sulfate), filter, and concentrate. Purify the crude material by silica gel chromatography, eluting with a gradient from 85:15 to 75:25 hexanes:ethyl acetate, then elute with 50:50 hexanes:ethyl acetate to give the title compound. Further purify by additional silica gel chromatography, eluting with 90:10 (70:30 hexanes:dichloromethane):ethyl acetate. Combine clean fractions from both chromatographies and concentrate to give the title compound as a crystalline solid (1.5 g, 75%).

$^1$H NMR (400 MHz, DMSO-d$_6$) δ 4.78 (s, 2H), 7.35 (dd, J=9.9 Hz, J=8.6 Hz, 1H), 7.64 (ddd, J=8.6 Hz, J=5.1 Hz, J=2.4 Hz, 1H), 7.79 (dd, J=7.5 Hz, J=2.2 Hz, 1H), 8.53 (t, J=2.2 Hz, 1H), 9.00-8.99 (m, 2H); MS (ES): m/z=271.0 [M+H]$^+$.

Preparation 33

2-Fluoro-5-iodobenzyl alcohol

Dissolve 2-fluoro-5-iodobenzaldehyde, (prepared essentially as described in Tet. Lett., 33, 7499, (1992)), (6.54 g, 26.1 mmol) in 4:1 tetrahydrofuran:methanol (200 mL) and treat with sodium borohydride (1.98 g, 52.3 mmol) and stir overnight. Concentrate the reaction mixture, then partition between ethyl acetate and water. Wash the organic layer with an aqueous saturated solution of sodium chloride, dry (sodium sulfate), filter, and concentrate. Purify the crude oil by silica gel chromatography, eluting with 85:15 hexanes:ethyl acetate, to give the title compound as a white crystalline solid (5.8 g, 88%).

$^1$H NMR (400 MHz, DMSO-d$_6$) δ 4.46 (d, J=5.7 Hz, 2H), 5.31 (t, J=5.7 Hz, 1H), 6.96 (dd, J=10.1, 8.8 Hz, 1H), 7.58 (ddd, J=8.6, 4.8, 2.4 Hz, 1H), 7.72 (dd, J=6.8, 2.4 Hz, 1H).

Preparation 34

N-(2-Fluoro-5-trimethylsilanylethynylbenzyl)-methanesulfonamide

Dissolve zinc (II) bromide (313 mg, 1.20 mmol) in tetrahydrofuran (2.5 mL) and treat with triethylamine (0.64 mL, 4.80 mmol). After 4 min add N-(5-bromo-2-fluorobenzyl)methanesulfonamide (282 mg, 1.00 mmol), (prepared as described in PREPARATION 35), trimethylsilylacetylene (0.30 mL, 2.12 mmol), and tetrakis(triphenylphosphine)palladium (0) (58 mg, 0.050 mmol) to the reddish solution. Heat to 60° C. in a sealed tube overnight, cool to room temperature and filter through diatomaceous earth with ethyl acetate. Concentrate the filtrate and purify the residue by silica gel chromatography, eluting with 75:25 hexanes:ethyl acetate, to give the title compound as a white crystalline solid (220 mg, 74%).

$^1$H NMR (400 MHz, DMSO-d$_6$) δ 0.19 (s, 9H), 2.88 (s, 3H), 4.14 (d, J=6.2 Hz, 2H), 7.17 (dd, J=10.1, 8.4 Hz, 1H), 7.39 (ddd, J=8.5, 4.9, 2.3 Hz, 1H), 7.50 (dd, J=7.5, 2.2 Hz, 1H), 7.54 (t, J=6.2 Hz, 1H); MS (ES): m/z=298.1 [M−H]$^−$.

Preparation 35

N-(5-Bromo-2-fluorobenzyl)methanesulfonamide

Dissolve 5-bromo-2-fluorobenzylamine hydrochloride (500 mg, 2.08 mmol) in dichloromethane (8 mL) and diisopropylethylamine (0.90 mL, 5.20 mmol) and treat with methanesulfonyl chloride (0.19 mL, 2.49 mmol). After 4.5 h dilute with ethyl acetate and wash with 0.5 N hydrochloric acid, an aqueous saturated solution of sodium bicarbonate, and an aqueous saturated solution of sodium chloride. Dry (sodium sulfate), filter, and concentrate to give the title compound as a pale orange oil, which crystallizes upon standing (573 mg, 98%).

$^1$H NMR (400 MHz, DMSO-d$_6$) δ 2.89 (s, 3H), 4.16 (d, J=6.2 Hz, 2H), 7.16 (dd, J=10.1, 8.8 Hz, 1H), 7.49 (ddd, J=8.8, 4.4, 2.6 Hz, 1H), 7.59-7.56 (m, 2H).

Preparation 36

(2-Fluoro-5-trimethylsilanylethynylbenzyl)-carbamic acid tert-butyl ester

Prepare according to the general procedure outlined in PREPARATION 31 using (5-bromo-2-fluorobenzyl)carbamic acid tert-butyl ester (0.912 g, 3.00 mmol), (prepared as described in PREPARATION 37). Purify the residue by silica gel chromatography, eluting with 95:5 hexanes:ethyl acetate, to give the title compound as a colorless oil, which crystallizes upon standing (653 mg, 68%).

$^1$H NMR (400 MHz, DMSO-d$_6$) δ 0.18 (s, 9H), 1.35 (s, 9H), 4.10 (d, J=6.2 Hz, 2H), 7.13 (dd, J=9.9, 8.6 Hz, 1H), 7.39-7.32 (m, 2H).

Preparation 37

(5-Bromo-2-fluorobenzyl)carbamic acid tert-butyl ester

Dissolve 5-bromo-2-fluorobenzylamine hydrochloride (1.00 g, 4.16 mmol) in 1,4-dioxane (16 mL) and 0.5 N sodium hydroxide (10 mL). Add di-tert-butyl dicarbonate (1.09 g, 4.99 mmol) and stir the biphasic mixture overnight. Make the aqueous layer acidic with aqueous saturated solution of sodium hydrogensulfate and extract three times with ethyl acetate. Combine the organic layers and wash with an aqueous saturated solution of sodium chloride, dry (sodium sulfate), filter, and concentrate to give the title compound as a colorless oil, which crystallizes upon standing (1.3 g, 100%).

$^1$H NMR (400 MHz, DMSO-d$_6$) δ 1.35 (s, 9H), 4.11 (d, J=5.7 Hz, 2H), 7.12 (dd, J=9.7, 8.8 Hz, 1H), 7.46-7.38 (m, 2H).

Preparation 38

5-(4-Fluoro-3-formylphenylethynyl)-nicotinonitrile

Combine 5-trimethylsilanylethynyl-nicotinonitrile (1.30 g, 11.5 mmol), (prepared as described in PREPARATION 3), 2-fluoro-5-iodobenzaldehyde (3.45 g, 13.8 mmol, (prepared essentially as described in Tet. Lett., 33, 7499, (1992)), bis(triphenylphosphine)palladium (II) dichloride (404 mg, 0.575 mmol), copper (I) iodide (219 mg, 1.15 mmol), and triethylamine (22.4 mL, 161 mmol) in tetrahydrofuran (9 mL). Cool the suspension to −78° C. and treat with a 1.0 M solution of tetrabutylammonium fluoride (11.5 mL) in tetrahydrofuran. After 10 min, heat to 60° C. for 2 h. Cool to room temperature and filter through diatomaceous earth washing with ethyl acetate. Purify the crude product by silica gel chromatography, eluting with a gradient from 80:20 to 60:40 hexanes:ethyl acetate, to give the title compound as an off-white crystalline solid (1.3 g, 45%).

$^1$H NMR (400 MHz, DMSO-d$_6$) δ 7.51 (dd, J=10.5, 8.8 Hz, 2H), 7.93 (ddd, J=8.7, 4.9, 2.3 Hz, 1H), 8.02 (dd, J=6.6, 2.2 Hz, 1H), 8.56 (t, J=2.2 Hz, 1H), 9.01 (d, J=2.2 Hz, 1H), 9.02 (d, J=2.2 Hz, 1H), 10.16 (s, 1H); MS (ES): m/z=251.0 [M−H]$^−$.

Preparation 39

2-Fluoro-5-iodo-N-methylbenzamide

Add methylamine hydrochloride (0.57 g, 8.4 mmol) and triethylamine (2.17 mL, 15.5 mmol) to a solution of 2-fluoro-5-iodobenzoyl chloride (2.0 g, 7.0 mmol) in dichloromethane (100 mL) at 0° C. Warm to room temperature and stir 20 h. Concentrate and purify by silica gel chromatography, eluting with a gradient of 75:25 to 60:40 hexanes:ethyl acetate, to give the title compound as a white solid (1.7 g, 87%).

$^1$H NMR (300 MHz, CDCl$_3$) δ 3.02-3.07 (m, 3H), 6.48-6.65 (br s, 1H), 6.84-6.95 (m, 1H), 7.71-7.79 (m, 1H), 8.38-8.43 (m, 1H).

Preparation 40

5-Bromo-2-fluorophenylamine

Add 4-bromo-1-fluoro-2-nitrobenzene (19.4 g, 88.2 mmol) and 10 g of fine mesh iron to a solution of acetic acid (75 mL) and water (5 mL) and heat to 105° C. for 4 h or until the 4-bromo-1-fluoro-2-nitrobenzene is completely consumed. Concentrate to remove most of the acetic acid, pour into water and extract with ethyl acetate. Wash the ethyl acetate layers with water, an aqueous saturated solution of sodium chloride, dry (potassium carbonate), filter and concentrate. Purify the residue by silica gel chromatography, eluting with hexanes:ethyl acetate, to give the title compound as an amber oil (11.3 g, 67%).

$^1$H NMR (400 MHz, DMSO-d$_6$) δ 5.39 (s, 2H), 6.57 (ddd, J=8.6 Hz, J=4.0 Hz, J=2.4 Hz, 1H), 6.92-6.85 (m, 2H).

Preparation 41

2-Fluoro-5-trimethylsilanylethynyl-phenylamine

Prepare essentially as described in PREPARATION 31 using 5-bromo-2-fluorophenylamine (6.0 g, 31.6 mmol), (prepared as described in PREPARATION 40), to give the title compound as a dark oil (5.6 g, 85.5%).

$^1$H NMR (400 MHz, CDCl$_3$) δ 0.20 (s, 9H), 3.73 (s, 2H), 6.81-6.77 (m, 1H), 6.89-6.84 (m, 2H).

Preparation 42

5-Bromo-2-fluorobenzoic acid methyl ester

Heat a solution of 5-bromo-2-fluorobenzoic acid (20 g, 92 mmol) and p-toluenesulfonic acid monohydrate (52 g, 275 mmol) in methanol (200 mL) at reflux overnight. Concentrate and dissolve the residue in ethyl acetate, wash twice with an aqueous saturated solution of sodium bicarbonate, once with an aqueous saturated solution of sodium chloride, dry (sodium sulfate), filter and concentrate to give the title compound as a clear liquid (19.7 g, 92%).

$^1$H NMR (400 MHz, CDCl$_3$) δ 3.92 (s, 3H), 7.00-7.05 (m, 1H), 7.58-7.62 (m, 1H), 8.04 (dd, J=2.6 Hz, J=6.2 Hz, 1H).

Preparation 43

2-Bromo-1-fluoro-4-iodobenzene

Add at 0° C. a solution of sodium nitrite (2.0 g, 28.9 mmol) in water (15 mL) to a suspension of 3-bromo-4-fluorophenylamine (5.0 g, 26.3 mmol) in a 6 N aqueous solution of hydrochloric acid (25 mL) at 0° C. slowly over 10 min. Stir the mixture at 0° C. for 5 min. Add this solution to a solution of potassium iodide (4.37 g, 26.3 mmol) in water (125 mL) via syringe at 0° C. under nitrogen over 15 min. Stir at 0° C. for 30 min. Warm to room temperature. Extract with four times with dichloromethane (100 mL), dry (sodium sulfate), filter, and concentrate. Purify by silica gel chromatography, eluting with 100:0 to 95:5 hexanes:ethyl acetate to give the title compound as a colorless oil (5.83 g, 74%).

$^1$H NMR (300 MHz, CDCl$_3$) δ 6.82-6.91 (t, J=8.5 Hz, 1H), 7.54-7.61 (m, 1H), 7.83-7.90 (dd, J=2.1 Hz, J=6.4 Hz, 1H).

Preparation 44

2-Fluoro-5-iodobenzamide

Add slowly 2-fluoro-5-iodobenzoyl chloride (4.0 g, 14.1 mmol) to a 7 N solution of ammonia in methanol (20 mL, 141 mmol) cooled to 0° C. Stir at 0° C. for 45 min then warm to room temperature and stir 5 h. Add an additional amount of the 7 N solution of ammonia in methanol (20 mL) to the reaction mixture and stir for 15 h. Concentrate, dilute with ethyl acetate (300 mL) and wash twice with water (30 mL) and twice with an aqueous saturated solution of sodium chloride (30 mL). Dry (sodium sulfate), filter, and concentrate. Purify by silica gel chromatography, eluting with 60:40 to 40:60 hexanes:ethyl acetate, to give the title compound as a white solid (3.45 g, 92%).

$^1$H NMR (300 MHz, CDCl$_3$) δ 6.06-6.32 (br s, 1H), 6.47-6.76 (br s, 1H), 6.87-6.96 (m, 1H), 7.75-7.84 (m, 1H), 8.40-8.47 (dd, J=2.4 Hz, 7.3 Hz, 1H); MS (APCI): m/z=266 [M+H]$^+$.

Preparation 45

2-Fluoro-5-iodo-N,N-dimethylbenzamide

Add a 2.0 M solution of dimethylamine in tetrahydrofuran (5 mL, 10.1 mmol) to a solution of 2-fluoro-5-iodobenzoyl-chloride (1.3 g, 4.6 mmol) in dichloromethane (20 mL) and stir at room temperature for 0.5 h. Sequentially wash the reaction mixture with a 1 N hydrochloric acid (50 mL), a 1 N sodium hydroxide (50 mL), and an aqueous saturated solution of sodium chloride (50 mL). Dry (sodium sulfate), filter, and concentrate to give the title compound as a white solid (1.3 g, 98%).

$^1$H NMR (300 MHz, CDCl$_3$) δ 2.94 (s, 3H), 3.12 (s, 3H), 6.84-6.90 (m, 1H), 7.65-7.71 (m, 2H); MS (APCI): m/z 293 [M+H]$^+$.

Preparation 46

1-Fluoro-4-iodo-2-nitrobenzene

Add isoamyl nitrite (18.6 g, 160 mmol) to a suspension of 4-fluoro-3-nitrophenylamine (5.0 g, 32 mmol) in diiodomethane (150 mL). Stir under nitrogen at room temperature for 1 h. Heat at 70° C. for 1 h. Cool to room temperature and concentrate. Dilute with dichloromethane (500 mL) and water (100 mL). Collect the organic, concentrate and purify (silica gel chromatography, eluting with a gradient of 100:0 to 80:20 hexanes:ethyl acetate), to give the title compound as a yellow oil (1.22 g, 14%).

$^1$H NMR (300 MHz, CDCl$_3$) δ 7.02-7.11 (m, 1H), 7.89-7.97 (m, 1H), 8.32-8.39 (dd, J=2.2 Hz, 6.9 Hz, 1H).

Preparation 47

1-Fluoro-4-iodo-2-methoxybenzene

Dissolve 4-fluoro-3-methoxyphenylamine (5.0 g, 35 mmol) in water (25 mL) and concentrated sulfuric acid (8 mL). Cool to less than 0° C. in an ice/methanol bath and add sodium nitrite (2.7 g, 39 mmol) dropwise in a solution in water (20 mL) and stir one h. Dissolve potassium iodide (9.9 g, 60 mmol) in water (35 mL) and add dropwise. Warm to room temperature and stir 18 h. Extract with ethyl acetate (300 mL), wash with water (200 mL), saturated aqueous sodium thiosulfate (300 mL), and saturated aqueous sodium chloride (300 mL). Dry (sodium sulfate), filter, and concentrate to give the title compound as an orange oil (8.8 g, 99%).

$^1$H NMR (300 MHz, CDCl$_3$) δ 3.88 (s, 3H), 6.77-6.87 (m, 1H), 7.16-7.26 (m, 2H).

Preparation 48

(5-Bromo-2-fluorobenzyl)-carbamic acid ethyl ester

Add ethyl chloroformate (0.24 mL, 2.49 mmol) to a solution of 5-bromo-2-fluorobenzylamine hydrochloride (500 mg, 2.08 mmol) in dichloromethane (8 mL) and diisopropylethylamine (0.90 mL, 5.20 mmol). After 3 h dilute the reaction with diethyl ether and wash twice with 1 N hydrochloric acid and once with an aqueous saturated solution of sodium chloride. Dry (sodium sulfate), filter, and concentrate to give the title compound as a colorless oil (0.527 g, 92%).

$^1$H NMR (400 MHz, DMSO-d$_6$) δ 1.12 (t, J=7.0 Hz, 3H), 3.96 (q, J=7.2 Hz, 2H), 4.16 (d, J=6.2 Hz, 2H), 7.13 (dd, J=9.7, 8.8 Hz, 1H), 7.47-7.40 (m, 2H), 7.64 (t, J=5.3 Hz, 1H).

Preparation 49

(2-Fluoro-5-trimethylsilanylethynylbenzyl)-carbamic acid ethyl ester

Prepare according to the general procedure outlined in PREPARATION 31 using (5-bromo-2-fluorobenzyl)-carbamic acid ethyl ester (0.912 g, 3.00 mmol), (prepared as described in PREPARATION 48). Purify the residue by silica gel chromatography, eluting with 90:10 hexanes:ethyl acetate, to give the title compound as a colorless oil (390 mg, 89%).

$^1$H NMR (400 MHz, DMSO-d$_6$) δ 0.18 (s, 9H), 1.12 (t, J=7.3 Hz, 3H), 3.96 (q, J=7.0 Hz, 2H), 4.15 (d, J=6.2 Hz, 2H), 7.13 (dd, J=9.9, 9.0 Hz, 1H), 7.37-7.34 (m, 2H), 7.62 (t, J=6.2 Hz, 1H).

Preparation 50

5-(3-Chloromethylphenylethynyl)-nicotinonitrile

Prepare according to the general procedure outlined in PREPARATION 32 using 5-(3-hydroxymethylphenylethynyl)-nicotinonitrile (0.360 g, 1.54 mmol), (prepared as described in EXAMPLE 197). Purify by silica gel chromatography, eluting with a gradient from 90:10 to 70:30 hexanes:ethyl acetate, to give the title compound as a white crystalline solid (318 mg, 82%).

$^1$H NMR (400 MHz, DMSO-d$_6$) δ 4.77 (s, 2H), 7.45 (t, J=7.5 Hz, 1H), 7.56-7.50 (m, 2H), 7.66-7.65 (m, 1H), 8.54 (t, J=2.0 Hz, 1H), 9.00 (d, J=2.6 Hz, 2H).

Preparation 51

5-Vinylnicotinonitrile

Add bis(triphenylphosphine)palladium (II) dichloride (0.460 g, 0.66 mmol) and tributyl-vinyl-stannane (7.2 mL, 24.6 mmol) to a solution of 5-bromonicotinonitrile (3.0 g, 16.4 mmol) in toluene (50 mL) and stir at 110° C. for 150 min. Add an aqueous saturated solution of ammonium chloride and ethyl acetate and separate the layers. Wash the organic layer twice with an aqueous saturated solution of potassium fluoride and once with water. Dry (sodium sulfate), filter, and concentrate. Purify the residue by silica gel chromatography, eluting with 3:1 hexane:ethyl acetate, to give the title compound (1.5 g, 70%).

$^1$H NMR (300 MHz, CDCl$_3$) δ 5.54 (d, J=11.0 Hz, 1H), 5.92 (d, J=17.5 Hz, 1H), 6.70 (dd, J=17.5 and 11.0 Hz, 1H), 7.96 (t, J=2.2 Hz, 1H), 8.74 (d, J=2.2 Hz, 1H), 8.79 (d, J=2.2 Hz, 1H); MS (ES): mm/z=131.1 [M+H]$^+$.

Example 1

3-Methyl-5-phenylethynylpyridine

Add phenylacetylene (0.460 mL, 4.2 mmol), copper (I) iodide (0.072 g, 0.38 mmol) and bis(triphenylphosphine)palladium (II) dichloride (0.133 g, 0.19 mmol) to a solution of 3-bromo-5-methylpyridine, (prepared essentially as described in PREPARATION 1), (0.654 g, 3.8 mmol) in degassed triethylamine (20 mL) and stir under nitrogen at 80° C. for 16 h. Cool the reaction mixture to room temperature, filter through diatomaceous earth, wash with ethyl acetate, and concentrate. Purify the residue by silica gel chromatography, eluting with 80:20 hexanes:ethyl acetate, to give the title compound as a brown oil (0.398 g, 54%).

$^1$H NMR (300 MHz, CDCl$_3$) δ 2.36 (s, 3 H), 7.39-7.35 (m, 3 H), 7.56-7.52 (m, 2 H), 7.65 (s, 1 H), 8.39 (s, 1 H), 8.58 (s, 1 H); $^{13}$C NMR (300 MHz, CDCl$_3$) δ 18.6, 86.4, 92.8, 120.3, 123.9, 128.8, 129.1, 132.1, 133.1, 1394, 149.4, 149.6; MS (ES): m/z=194.1 [M+H]$^+$.

Example 2

3-Methyl-5-phenylethynylpyridine hydrochloride

Add a 4 N solution of hydrogen chloride in 1,4-dioxane (0.6 mL) to a solution of 3-methyl-5-phenylethynylpyridine (0.398 g, 2.06 mmol), (prepared essentially as described in EXAMPLE 1), in diethyl ether (2 mL). Concentrate the reaction mixture and triturate the resulting solid with hexanes and diethyl ether to give the title compound as a solid (0.477 mg, 100%).

$^1$H NMR (300 MHz, CDCl$_3$) δ 2.61 (s, 3 H), 7.43-7.41 (m, 3 H), 7.57-7.55 (m, 2 H), 8.26 (br s, 1 H), 8.62 (br s, 1 H), 8.69 (br s, 1 H); $^{13}$C NMR (300 MHz, CDCl$_3$) δ 19.5, 82.1, 98.5, 120.9, 124.6, 129.1, 130.7, 132.6, 138.6, 140.3, 140.9, 147.9; MS (ES): m/z=194.1 [M+H]$^+$.

Example 3

3-Phenylethynylpyridine

Add phenylacetylene (0.175 mL, 1.6 mmol), copper (I) iodide (0.028 g, 0.15 mmol) and bis(triphenylphosphine)palladium (II) dichloride (0.051 g, 0.07 mmol) to a solution of 3-bromopyridine (0.140 mL, 1.45 mmol) in degassed triethylamine (6 mL) and stir under nitrogen at 80° C. for 16 h. Cool to room temperature, filter through diatomaceous earth, wash with ethyl acetate, and concentrate. Purify the residue by silica gel chromatography, eluting with 100:0 to 0:100 hexanes:dichlormethane, to give the title compound (91.1 mg, 35%).

$^1$H NMR (300 MHz, CDCl$_3$) δ 7.32 (br s, 1 H), 7.33-7.39 (m, 3 H), 7.52-7.57 (m, 2 H), 7.84 (d, J=1.6 Hz, 1 H), 8.61 (br s, 1 H), 8.83 (br s, 1 H); MS (ES): m/z=180 [M+H]$^+$.

Example 4

1-Oxy-5-phenylethynylnicotinonitrile

Add bis(trimethylsilyl)peroxide (3 mL, 15 mmol) to a suspension of 5-phenylethynylnicotinonitrile (2.04 g, 10 mmol) and 65-70% perrhenic acid (8.5 μL, 0.05 mmol) in dichloromethane (1.5 mL) and stir at room temperature for 24 h. Add dichloromethane (1.5 mL) and stir for an additional 8 h. Dilute with hexanes (30 mL) and collect the solid. Purify by silica gel chromatography, eluting with 100:0 to 0:100 dichloromethane:ethyl acetate, and recrystallize in ethyl acetate to give the title compound as a white solid (910 mg, 41%).

$^1$H NMR (300 MHz, CDCl$_3$) δ 8.41 (t, J=1.4 Hz, 1H), 8.33 (t, J=1.4 Hz, 1 H), 7.57 (t, J=1.4 Hz, 1 H), 7.54 (m, 2 H), 7.43 (m, 3 H); $^{13}$C NMR (75 MHz, CDCl$_3$) δ 144.7, 140.7, 132.4, 130.6, 130.2, 129.1, 125.1, 121.1, 113.9, 113.2, 97.7, 81.8; MS (ES): m/z=221 [M+H]$^+$.

Example 5

5-Phenylethynylpyridine-3-carbaldehyde

Charge an oven dried round bottom flask under nitrogen with a solution of N-methoxy-N-methyl-5-phenylethynylnicotinamide (2.00 g, 7.51 mmol), (prepared essentially as described in PREPARATION 2), in anhydrous toluene (20 mL) and cool to −78° C. Add a 1 M solution of diisobutylaluminum hydride in toluene (18 mL, 18 mmol) dropwise over 30 min and stir for an additional 30 min. Rapidly add methanol (15 mL) and warm to room temperature. Pour the reaction mixture into 100 mL of a saturated aqueous solution of Rochelle salt (potassium sodium tartrate) and stir vigorously for about 30 min. Upon standing, separate the organic layer, dry (magnesium sulfate), filter and concentrate. Purify the residue by silica gel chromatography, eluting with 50:50 hexanes:ethyl acetate, to obtain the title compound as a white solid (1.2 g, 77%).

$^1$H NMR (400 MHz, CDCl$_3$) δ 7.38-7.41 (m, 3H), 7.55-7.58 (m, 2H), 8.26-8.27 (m, 1H), 8.98 (dd, J=13.6, 2.0 Hz, 2H), 10.13 (s, 1H); LC-MS (ES): m/z=208 [M+H]$^+$.

Example 6

5-Phenylethynylpyridine-3-carbaldehyde oxime hydrochloride

Dissolve 5-phenylethynylpyridine-3-carbaldehyde (prepared essentially as described in EXAMPLE 5), (0.19 g, 0.70 mmol) in ethanol (2.0 mL) and sequentially add potassium carbonate (0.48 g, 3.5 mmol) and hydroxylamine hydrochloride (0.39 g, 5.6 mmol). Heat at reflux for 3 h, cool to room temperature and filter. Concentrate the filtrate and purify by reverse phase chromatography (ISCO-130™ C-18 column), using a linear gradient of 0% to 100% over 40 min and a mobile phase of water (0.05% trifluoroacetic acid and acetonitrile) to obtain the trifluoroacetic acid salt of the title compound.

Dissolve the above trifluoroacetic acid salt of the title compound in diethyl ether with enough dichloromethane to obtain a homogenous solution and add a 1 N solution of hydrochloric acid (0.5 mL, 1.1 eq to trifluoroacetic acid salt) in diethyl ether. Stir at room temperature for 2 h and filter to give the title compound, after drying, as a solid (0.12 g, 65%).

$^1$H NMR (400 MHz, CH$_3$OH-d4) δ 7.46-7.49 (m, 3H), 7.65 (dd, J=7.6 Hz, 1.6 Hz, 2H), 8.29 (s, 1H), 8.75 (s, 1H), 8.99 (s, 2H); LC-MS (ES): z/z=223 [M+H]$^+$; Anal Calcd for C$_{14}$H$_{10}$N$_2$O—HCl: C, 64.99; H, 4.28; N, 10.82 Found C, 65.17; H, 4.40; N, 10.79.

Example 7

(E)-5-Phenylethynylpyridine-3-carbaldehyde O-methyloxime hydrochloride

Dissolve 5-phenylethynylpyridine-3-carbaldehyde (0.20 g, 0.97 mmol), (prepared essentially as described in EXAMPLE 5), in ethanol (2.0 mL) and sequentially add potassium carbonate (0.67 g, 4.8 mmol) and methoxylamine hydrochloride (0.64 g, 5.6 mmol). Heat at reflux overnight, cool to room temperature and filter. Concentrate and purify by silica gel chromatography, eluting with a linear gradient of 90:10 to 50:50 hexanes:ethyl acetate to obtain the free base of the title compound as a colorless oil as well as a minor amount of EXAMPLE 86.

Dissolve the above free base of the title compound in diethyl ether and add a 1 N solution of hydrochloric acid in diethyl ether (0.9 mL, 1.1 eq to free base). Stir at room temperature for 2 h and filter to give the title compound, after drying under high vacuum overnight, as a solid (0.22 g, 84%).

$^1$H NMR (400 MHz, CH$_3$OH-d4): 4.06 (s, 3H), 7.46 (d, J=7.2 Hz, 2H), 7.47 (s, 1H), 7.63 (dd, J=7.6, 1.2 Hz, 2H), 8.30 (s, 1H), 8.76 (s, 1H), 8.97 (d, J=9.2 Hz, 2H); LC-MS (ES): m/z=237 [M+H]$^+$.

Example 8

(E)-3-(5-Phenylethynylpyridin-3-yl)acrylic acid methyl ester hydrochloride

Dissolve 5-phenylethynyl-pyridine-3-carbaldehyde (0.20 g, 0.97 mmol), (prepared essentially as described in EXAMPLE 5), and methyl(triphenylphosphoranylide)acetate (0.36 g, 1.1 mmol) in dichloromethane (3.0 mL) and stir at room temperature overnight. Concentrate and purify the residue by silica gel chromatography, eluting with a linear gradient of 90:10 to 50:50 hexanes:ethyl acetate, to obtain the free base of the title compound as a white solid.

Dissolve the above free base of the title compound in diethyl ether and add a 1 N solution of hydrochloric acid in diethyl ether (0.92 mL, 1.1 eq to free base). Stir at room temperature for 2 h, filter and dry to give the title compound as a solid (0.25 g, 86%).

$^1$H NMR (400 MHz, DMSO-d$_6$) δ 3.83 (s, 3H), 6.97 (d, J=16.0 Hz, 1H); 7.45-7.47 (m, 3H); 7.63-7.65 (m, 2H); 7.80 (d, J=16.4 Hz, 1H), 8.93 (s, 1H), 9.02 (s, 1H), 9.06 (s, 1H); LC-MS (ES): m/z=264 [M+H]$^+$.

Example 9

3-Bromo-5-phenylethynyl-pyridine

Add phenylacetylene (1.11 mL, 10.10 mmol) dropwise to a mixture of 3,5-dibromopyridine (2.05 g, 8.65 mmol), bis(triphenylphosphine)palladium (II) dichloride (300 mg, 0.427 mmol), and copper (I) iodide (160 mg, 0.840 mmol) in triethylamine (8.50 mL, 60.98 mmol) and stir for 3 h at room temperature. Dilute the reaction mixture with ethyl acetate and wash with a saturated aqueous solution of sodium chloride. Dry (sodium sulfate), filter and concentrate. Purify the residue by silica gel chromatography, eluting with a gradient of 100:0 to 90:10 hexanes:ethyl acetate, to give the title compound (710 mg, 32%).

$^1$H NMR (400 MHz, CDCl$_3$) δ 7.40-7.43 (m, 3H), 7.57-7.59 (m, 2H), 8.00 (t, J=2.2 Hz, 1H), 8.65 (d, J=1.8 Hz, 1H), 8.70 (br s, 1H); MS (ES): m/z=258.0 (99%), 260.0 (100%) [M+H]$^+$; HRMS Calcd for C$_{13}$H$_9$BrN 257.9918 Found 257.9921.

Example 10

5-(2-Chlorophenylethynyl)-nicotinonitrile

Add bis(triphenylphosphine)palladium (II) dichloride (63.2 mg, 0.090 mmol), copper (I) iodide (34.3 mg, 0.180 mmol), and 5-ethynylnicotinonitrile (242 mg, 1.89 mmol), (prepared essentially as described in PREPARATION 4), to a solution of 1-chloro-2-iodobenzene (0.22 mL, 1.77 mmol) in triethylamine (3.60 mL, 25.8 mmol) and heat to 70° C. in a sealed tube for 1.5 h. Cool to room temperature and dilute with ethyl acetate. Wash with a saturated aqueous solution of sodium chloride, dry (sodium sulfate), filter and concentrate. Purify the residue by silica gel chromatography, eluting with a gradient from 95:5 to 80:20 (90:10 hexanes:ethyl acetate):dichloromethane, to give the title compound as a yellow solid. Further purify the title compound by recrystallizing from cyclohexane (20 mL) to give a white solid (95 mg, 22%).

$^1$H NMR (400 MHz, CDCl$_3$) δ 7.33 (dt, J=7.5, 1.3 Hz, 1H), 7.39 (dt, J=7.5, 1.8 Hz, 1H), 7.51 (dd, J=7.9, 1.3 Hz, 1H), 7.62 (dd, J=7.5, 1.8 Hz, 1H), 8.14 (t, J=2.2 Hz, 1H), 8.86 (br s, 1H), 9.00(br s, 1H); HRMS Calcd for C$_{14}$H$_8$ClN$_2$ 239.0376 Found 239.0384; Anal Calcd for C$_{14}$H$_7$ClN$_2$: C, 70.45; H, 2.96; N, 11.74 Found: C, 70.01; H, 3.02; N, 11.23.

Example 11

5-(3-Chlorophenylethynyl)-nicotinonitrile

Combine 5-Trimethylsilanylethynyl-nicotinonitrile (3.00 g, 15.0 mmol), (prepared as described in PREPARATION 3), bis(triphenylphosphine)palladium (II) dichloride (526 mg, 0.750 mmol), copper (I) iodide (286 mg, 1.50 mmol), and 3-chloroiodobenzene (2.24 μL, 18.0 mmol) in triethylamine (29.3 mL, 210 mmol). Cool the mixture to −78° C. and add a 1 M solution of tetrabutylammonium fluoride in tetrahydrofuran (15.3 mL, 15.3 mmol). After 5 min warm to room temperature and stir 72 h. Filter the reaction through diatomaceous earth, washing with ethyl acetate. Concentrate the filtrate and purify by silica gel chromatography, eluting with a gradient from 95:5 to 70:30 (90:10 hexanes:ethyl acetate):dichloromethane. Further purify by silica gel chromatography, eluting with dichloromethane, then 90:10 dichloromethane:ethyl acetate. Dissolve the chromatographed material (2.91 g) in cyclohexane (120 mL) at 80° C. and cool to room temperature. Collect the recrystallized material via vacuum filtration to give the title compound as a white crystalline solid (2.58 g, 72%).

$^1$H NMR (400 MHz, DMSO-d$_6$) δ 7.49 (t, J=7.7 Hz, 1H), 7.58-7.54 (m, 2H), 7.69 (t, J=1.8 Hz, 1H), 8.57 (t, J=2.0 Hz, 1H), 9.02 (d, J=1.8 Hz, 1H), 9.04 (d, J=2.2 Hz, 1H); HRMS Calcd for C$_{14}$H$_8$ClN$_2$ 239.0376 Found 239.0376; Anal Calcd for C$_{14}$H$_7$ClN$_2$.0.1H$_2$O: C, 70.45; H, 2.96; N, 11.74 Found: C, 69.85; H, 2.92; N, 11.36.

Example 12

5-(2-Fluorophenylethynyl)-nicotinonitrile

Prepare according to the general procedure outlined in EXAMPLE 10 using 1-fluoro-2-iodobenzene (0.22 mL, 1.89 mmol) to give the title compound (50 mg, 12%).

¹H NMR (400 MHz, CDCl₃) δ 7.16-7.24 (m, 2H), 7.42-7.47 (m, 1H), 7.58 (dt, J=7.0, 1.8 Hz, 1H), 8.13 (t, J=2.2 Hz, 1H), 8.85 (d, J=1.8 Hz, 1H), 8.98 (d, J=1.8 Hz, 1H); HRMS Calcd for $C_{14}H_8FN_2$ 223.0671 Found 223.0695; Anal Calcd for $C_{14}H_7FN_2$: C, 75.67; H, 3.18; N, 12.60 Found: C, 75.45; H, 3.32; N, 12.53.

Example 13

5-(3-Fluorophenylethynyl)-nicotinonitrile

Add bis(triphenylphosphine)palladium (II) dichloride (390 mg, 0.56 mmol), copper (I) iodide (211 mg, 1.11 mmol), and 5-ethynylnicotinonitrile (1.50 g, 11.7 mmol), (prepared essentially as described in PREPARATION 4), to a solution of 1-fluoro-3-iodobenzene (1.31 mL, 11.1 mmol) in triethylamine (21.6 mL, 155 mmol) and heat to 80° C. in a sealed tube for 1.5 h. Cool to room temperature and dilute with ethyl acetate. Wash with a 50% saturated aqueous solution of sodium bicarbonate. Back-extract the aqueous layer three times with dichloromethane and twice with ethyl acetate until the aqueous layer is no longer an emulsion. Combine all organic layers and wash with a saturated aqueous solution of sodium chloride, dry (sodium sulfate), filter and concentrate. Dissolve the residue in ethyl acetate and filter through diatomaceous earth then purify by silica gel chromatography, eluting with a gradient from 95:5 to 80:20 (90:10 hexanes:ethyl acetate):dichloromethane. Further purify by silica gel chromatography, eluting with dichloromethane then 95:5 dichloromethane:ethyl acetate, to give the title compound as a white crystalline solid (1.8 g, 71%).

¹H NMR (400 MHz, CDCl₃) δ 7.14-7.19 (m, 1H), 7.27-7.30 (m, 1H), 7.36-7.44 (m, 2H), 8.11 (t, J=1.8 Hz, 1H), 8.86 (br s, 1H), 8.96 (br s, 1H); HRMS Calcd for $C_{14}H_8FN_2$ 223.0671 Found 223.0691; Anal Calcd for $C_{14}H_7FN_2 \cdot 0.1H_2O$: C, 75.06; H, 3.24; N, 12.51 Found: C, 74.85; H, 3.21; N, 12.20.

Example 14

5-(4-Fluorophenylethynyl)-nicotinonitrile

Prepare according to the general procedure outlined in EXAMPLE 11 using 1-fluoro-4-iodobenzene (4.39 mL, 19.8 mmol) to give the title compound (2.44 g, 66%).

¹H NMR (400 MHz, CDCl₃) δ 7.11-7.16 (m, 2H), 7.56-7.60 (m, 2H), 8.09 (t, J=2.2 Hz, 1H), 8.83 (d, J=1.8 Hz, 1H), 8.95 (d, J=1.8 Hz, 1H); HRMS Calcd for $C_{14}H_8FN_2$ 223.0671 Found 223.0669 Anal Calcd for $C_{14}H_7FN_2$: C, 75.67; H, 3.18; N, 12.60.

Found: C, 75.61; H, 3.21; N, 12.51.

Example 15

(E)-5-Styrylnicotinonitrile

Add tris(dibenzylideneacetone)dipalladium (125 mg, 0.136 mmol) and tri-o-tolylphosphine (86 mg, 0.273 mmol) to a solution of triethylamine (0.77 mL, 5.46 mmol), 5-bromonicotinonitrile (500 mg, 2.73 mmol) and styrene (0.48 mL, 4.1 mmol) in anhydrous N,N-dimethylformamide (10 mL) under an inert atmosphere, and stir at 100° C. for 3.5 h. Cool to room temperature, add water and extract three times with diethyl ether. Combine the organic layers, dry (sodium sulfate), filter, and concentrate. Purify the residue by silica gel chromatography, eluting with dichloromethane, to give the title compound as a white solid (190 mg, 34%).

¹H NMR (300 MHz, CDCl₃) δ 8.90 (d, J=1.9 Hz, 1H); 8.73 (d, J=1.9 Hz, 1H); 8.07 (t, J=1.9 Hz, 1H); 7.56-7.52 (m, 2H); 7.44-7.32 (m, 3H); 7.23 (d, J=16.0 Hz, 1H); 7.05 (d, J=16.0 Hz, 1H); ¹³C NMR (75 MHz, CDCl₃) δ 151.2; 150.3; 135.7; 135.5; 133.7; 133.5; 129.1; 128.9; 126.9; 122.3; 116.5; 110.1; MS (ES): m/z=207 [M+H]⁺.

Example 16

5-(3,4-Dimethylphenylethynyl)-nicotinonitrile

Combine 4-iodo-o-xylene (0.362 g, 1.561 mmol), bis(triphenylphosphine)palladium (II) dichloride (55 mg, 0.078 mmol), and copper (I) iodide (30 mg, 0.156 mmol) in triethylamine (0.653 mL, 4.683 mmol) and stir under nitrogen for 5 min at 80° C. Add a solution of 5-ethynylnicotinonitrile, (prepared essentially as described in PREPARATION 4), (200 mg, 1.561 mmol) in anhydrous acetonitrile (2.50 mL), and stir under nitrogen overnight. Cool to room temperature and dilute with diethyl ether. Wash with a saturated aqueous solution of sodium bicarbonate, dry (sodium sulfate), filter, and concentrate. Purify the residue by silica gel chromatography, eluting with 95:5 to 50:50 dichloromethane:ethyl acetate, to give the title compound as a yellow solid (225 mg, 62%).

¹H NMR (400 MHz, CH₃OH-d4) δ 2.32 (s, 3H), 2.34 (s, 3H), 7.21 (d, J=7.9 Hz, 1H), 7.33 (d, J=8.0 Hz, 1H), 7.39 (s, 1H), 8.33 (t, J=2.0 Hz, 1H), 8.87 (br s, 1H), 8.94 (br s, 1H); LC-MS (ES): m/z=233 [M+H]⁺.

Example 17

5-(3,5-Dimethylphenylethynyl)-nicotinonitrile

Prepare according to the general procedure outlined in EXAMPLE 16 using 5-iodo-m-xylene (246 mg, 1.061 mmol). Purify by silica gel chromatography, eluting with a gradient of 95:5 to 60:40 dichloromethane:ethyl acetate, to give the title compound as a white solid (60 mg, 24%).

¹H NMR (400 MHz, CH₃OH-d4) δ 2.35 (s, 6H), 7.13 (s, 1H), 7.24 (s, 2H), 8.34 (t, J=2.0 Hz, 1H), 8.88 (d, J=2.2 Hz, 1H), 8.94 (d, J=2.2 Hz, 1H); LC-MS (ES): m/z=233 [M+H]⁺.

Example 18

5-(2,4-Dimethylphenylethynyl)-nicotinonitrile

Prepare according to the general procedure outlined in EXAMPLE 16 using 4-iodo-m-xylene (362 mg, 1.561 mmol). Purify by silica gel chromatography, eluting with a gradient of 95:5 to 60:40 dichloromethane:ethyl acetate, to give the title compound as a tan solid (247 mg, 68%).

¹H NMR (400 MHz, CDCl₃) δ 2.39 (s, 3H), 2.51 (s, 3H), 7.06 (d, J=7.9 Hz, 1H), 7.12 (s, 1H), 7.44 (d, J=7.9 Hz, 1H), 8.06-8.08 (m, 1H), 8.84 (br s, 1H), 8.95 (br s, 1H); LC-MS (ES): m/z=233 [M+H]⁺.

Example 19

5-(2,5-Dimethylphenylethynyl)-nicotinonitrile

Prepare according to the general procedure outlined in EXAMPLE 16 using 2-iodo-p-xylene (362 mg, 1.561 mmol). Purify by silica gel chromatography, eluting with a gradient of 95:5 to 60:40 dichlromethane:ethyl acetate, to give the title compound as an off-white solid (183 mg, 78%).

$^1H$ NMR (400 MHz, $CDCl_3$) δ 2.37 (s, 3H), 2.50 (s, 3H), 7.13-7.21 (m, 2H), 7.37 (s, 1H), 8.07 (s, 1H), 8.83 (br s, 1H), 8.96 (br s, 1H); LC-MS (ES): m/z=233 $[M+H]^+$.

Example 20

5-(2-Cyanophenylethynyl)-nicotinonitrile

Prepare according to the general procedure outlined in EXAMPLE 10 using 2-iodobenzonitrile (0.45 g, 2.0 mmol) to give the title compound (35 mg, 8%).

$^1H$ NMR (300 MHz, $CDCl_3$) δ 7.56 (dt, J=1.7, 7.6 Hz, 1H), 7.64-7.80 (m, 3H), 8.18 (t, J=2.0 Hz, 1H), 8.88 (d, J=2.0 Hz, 1H), 9.03 (d, J=2.3 Hz, 1H). HRMS Calcd for $C_{15}H_8N_3$ 230.0718 Found 230.0730; Anal Calcd for $C_{15}H_7N_3$: C, 78.59; H, 3.08; N, 18.33 Found: C, 78.33; H, 3.12; N, 18.09.

Example 21

5-(3-Cyanophenylethynyl)-nicotinonitrile

Prepare essentially as described in EXAMPLE 10 using 3-iodobenzonitrile (0.45 g, 2.0 mmol) to give the title compound (140 mg, 31%).

$^1H$ NMR (300 MHz, $CDCl_3$) δ 7.56 (dt, J=0.7 Hz, 7.9 Hz, 1H), 7.73 (td, J=1.3 Hz, 7.9 Hz, 1H), 7.81 (td, J=1.3 Hz, 7.9 Hz, 1H), 7.87-7.88 (m, 1H), 8.12 (t, J=2.0 Hz, 1H), 8.88 (d, J=2.0 Hz, 1H), 8.97 (d, J=2.0 Hz, 1H); HRMS Calcd for $C_{15}H_8N_3$ 230.0718. Found 230.0739.

Example 22

5-(4-Cyanophenylethynyl)-nicotinonitrile

Prepare essentially as described in EXAMPLE 10 using 4-iodobenzonitrile (0.45 g, 2.0 mmol) to give the title compound (200 mg, 44%).

$^1H$ NMR (300 MHz, $CDCl_3$) δ 7.74-7.67 (m, 4H), 8.13 (s, 1H), 8.87 (s, 1H), 8.97 (s, 1H); HRMS Calcd for $C_{15}H_8N_3$ 230.0718 Found 230.0754; Anal Calcd for $C_{15}H_7N_3$: C, 78.59; H, 3.08; N, 18.33 Found: C, 78.09; H, 3.05; N, 17.97.

Example 23

5-(2-Methoxyphenylethynyl)-nicotinonitrile

Prepare essentially as described in EXAMPLE 10 using 2-iodoanisole (0.46 g, 2.0 mmol) to give the title compound (40 mg, 9%).

$^1H$ NMR (300 MHz, $CDCl_3$) δ 3.97 (s, 3H), 7.0 (q, J=7.9 Hz, 1H), 7.40-7.45 (m, 1H), 7.53 (dd, J=1.3 Hz, 7.6 Hz, 1H), 8.11 (t, J=2.0 Hz, 1H), 8.81 (t, J=2.0 Hz, 1H), 8.97 (d, J=2.0 Hz, 1H); HRMS Calcd for $C_{15}H_{11}N_2O$ 235.0871 Found 235.0868.

Example 24

5-(3-Methoxyphenylethynyl)-nicotinonitrile

Prepare essentially as described in EXAMPLE 10 using 3-iodoanisole (0.46 g, 2.0 mmol) to give the title compound (38 mg, 8%).

$^1H$ NMR (300 MHz, $CDCl_3$) δ 3.88 (s, 3H), 7.01 (ddd, J=1.0 Hz, 2.6 Hz, 8.2 Hz, 1H), 7.10-7.11 (m, 1H), 7.17-7.20 (m, 1H), 7.34 (t, J=8.2 Hz, 1H), 8.10 (t, J=2.0 Hz, 1H), 8.83 (d, J=2.0 Hz, 1H), 8.95 (d, J=2.0 Hz, 1H); HRMS Calcd for $C_{15}H_{11}N_2O$ 235.0871 Found 235.0848.

Example 25

5-(4-Methoxyphenylethynyl)-nicotinonitrile

Prepare essentially as described in EXAMPLE 10 using 4-iodoanisole (0.46 g, 2.0 mmol) to give the title compound (44 mg, 10%).

$^1H$ NMR (300 MHz, $CDCl_3$) δ 3.89 (s, 3H), 6.93-6.97 (m, 2H), 7.51-7.55 (m, 2H), 8.07 (t, J=2.0 Hz, 1H), 8.80 (d, J=2.0 Hz, 1H), 8.92 (d, J=2.0 Hz, 1H); HRMS Calcd for $C_{15}H_{11}N_2O_1$ 235.0871 Found 235.0890; Anal Calcd for $C_{15}H_{10}N_2O$: C, 76.91; H, 4.30; N, 11.96 Found: C, 76.67; H, 4.39; N, 11.83.

Example 26

3-Pyridin-3-ylethynyl-benzonitrile

Add triethylamine (5 mL) to a stirring mixture of 3-iodopyridine (1.03 g, 5.03 mmol), bis(triphenylphosphine)palladium (II) dichloride (176 mg, 0.252 mmol), copper (I) iodide (96 mg, 0.503 mmol), and 3-trimethylsilanylethynylbenzonitrile, (prepared essentially as described in PREPARATION 5), (1.0 g, 5.03 mmol) at −78° C. After about 3 min, add a 1 M solution of tetrabutylammonium fluoride in tetrahydrofuran (5.03 mL, 5.03 mmol) in one portion, warm to room temperature and stir overnight. Filter the reaction mixture through fluted filter paper and concentrate. Dissolve the residue in ethyl acetate, wash sequentially with a saturated solution of aqueous sodium bicarbonate, a saturated solution of aqueous sodium chloride, dry (sodium sulfate), filter, concentrate and purify (silica gel chromatography, eluting with 0:100 to 40:60 ethyl acetate:hexanes, followed by a second silica gel chromatography, eluting with 0:100 to 40:60 ethyl acetate:dichloromethane), to give the title product as a yellow solid (730 mg, 71%).

$^1H$ NMR (400 MHz, $CDCl_3$) δ 7.41 (br s, 1H), 7.54 (t, J=8.0 Hz, 1H), 7.67-7.70 (m, 1H), 7.78-7.81 (m, 1H), 7.87-7.89 (m, 2H), 8.60-9.10 (br m, 2H); LC-MS (ES): m/z=205 $[M+H]^+$.

Example 27

3-Pyridin-3-ylethynyl-benzonitrile hydrochloride

Bubble anhydrous hydrogen chloride gas through a solution of 3-pyridin-3-ylethynyl-benzonitrile, (prepared essentially as described in EXAMPLE 26), (730 mg, 3.58 mmol) in anhydrous diethyl ether (160 mL) at 0° C. for about 2 min and concentrate. Triturate the solid with diethyl ether, filter, and wash with diethyl ether to give the title compound, after drying under vacuum, as a light tan solid (789 mg, 92%).

$^1H$ NMR (400 MHz, DMSO-$d_6$) δ 7.71 (t, J=8.4 Hz, 1H), 7.85 (br s, 1H), 7.97 (dd, J=1.4 Hz, 8.2 Hz, 2H), 8.15-8.16 (m, 1H), 8.37 (d, J=7.9 Hz, 1H), 8.70-9.3 (br m, 2H); LC-MS (ES): m/z=205 $[M+H]^+$.

Example 28

3-Iodo-5-phenylethynylpyridine

Heat a mixture of 3-bromo-5-phenylethynylpyridine (5.71 g, 22.12 mmol), (prepared essentially as described in EXAMPLE 9), copper (I) iodide (211 mg, 1.1 mmol), sodium iodide (6.63 g, 44.24 mmol) and N,N'-dimethylethylenediamine (0.24 mL, 2.21 mmol) in 1,4-dioxane (20 mL) at 110° C. for 60 h. Cool to room temperature, dilute with ethyl acetate and wash with a saturated aqueous solution of sodium chloride, and dry (sodium sulfate). Purify the residue by silica gel chromatography, eluting with 15:1 hexanes:ethyl acetate, to give the title compound (5.45 g, 81%).

$^1$H NMR (300 MHz, CDCl$_3$) δ 7.34-7.40 (m, 3 H), 7.49-7.56 (m, 2 H), 8.15 (dd, J=2.0, 1.6 Hz, 1 H), 8.68 (d, J=1.6 Hz, 1 H), 8.75 (d, J=2.0 Hz, 1 H); MS (ES): m/z=306 [M+H]$^+$.

Example 29

3-Chloro-5-phenylethynylpyridine

Charge a Schlenk tube under a positive pressure of argon with bis(acetonitrile)palladium (II) chloride (5 mg), 2-dicyclohexylphosphinodiphenyl (21 mg), cesium carbonate (1.69 g, 5.2 mmol) and 3,5-dichloropyridine (0.3 g, 2 mmol) in acetonitrile and stir at room temperature for 25 min (Angew. Chem. Int. Ed. 42, 5993-5996, (2003)). Add phenylacetylene (0.285 mL, 2.6 mmol) and stir at 95° C. for 16 h. Dilute the reaction mixture with water and diethyl ether and separate the phases. Wash the organic layer with water, concentrate and purify the residue by silica gel chromatography, eluting with 50:50 hexanes:dichloromethane to obtain the title compound (68 mg, 16%).

$^1$H NMR (300 MHz, CDCl$_3$) δ 7.36-7.39 (m, 3 H), 7.53-7.56 (m, 2 H), 7.80 (t, J=2.0 Hz, 1 H), 8.50 (d, J=2.4 Hz, 1 H), 8.62 (d, J=1.6 Hz, 1 H); $^{13}$C NMR (75 MHz, 1$_3$) δ 84.9, 94.3, 121.9, 122.4, 128.9, 129.6, 132.0, 132.2, 138.3, 147.9, 150.2; MS (ES): m/z=316.3, 318.4 [M+H]$^+$.

Example 30

3-Methoxy-5-phenylethynylpyridine

Add phenylacetylene (0.180 mL, 1.6 mmol), copper (I) iodide (0.029 g, 0.15 mmol) and bis(triphenylphosphine)palladium (II) dichloride (0.053 g, 0.08 mmol) to a solution of 3-bromo-5-methoxypyridine (0.282 g, 1.5 mmol) in degassed triethylamine (8 mL) and heat at 80° C. for 16 h. Cool the reaction mixture to room temperature, filter through diatomaceous earth, wash with ethyl acetate, and concentrate. Purify the residue by silica gel chromatography, eluting with 50:50 to 0:100 hexanes:ethyl acetate to give the title compound (0.206 g, 66%).

$^1$H NMR (300 MHz, DMSO-d$_6$) δ 3.86 (s, 3 H), 7.44-7.47 (m, 3 H), 7.56-7.60 (m, 3 H), 8.85 (br s, 1 H); MS (ES): m/z=210 [M+H]$^+$.

Example 31

3-Hydroxy-5-phenylethynylpyridine

Add boron tribromide (1 mL, 1 mmol) dropwise to solution of 3-methoxy-5-phenylethynylpyridine, (prepared as described in EXAMPLE 30), (0.073 g, 0.35 mmol) in dichloromethane (0.7 mL) at −78° C. and stir for 15 min. Warm the reaction mixture to room temperature and stir overnight. Add a saturated aqueous solution of sodium bicarbonate to the reaction mixture and stir for 10 min to provide a biphasic solution. Separate the organic layer and wash it sequentially with a saturated solution of aqueous sodium bicarbonate and a saturated aqueous solution of sodium chloride. Dry (sodium sulfate), concentrate and purify by silica gel chromatography, eluting with 100:0 to 0:100 hexanes:ethyl acetate, to obtain the title compound (0.003 g, 4%).

$^1$H NMR (300 MHz, CH$_3$OH-d4) δ 7.41-7.47 (m, 4 H), 7.56-7.59 (m, 3 H), 8.13 (s, 1 H), 8.24 (s, 1 H); MS (ES): m/z=196.2 [M+H]$^+$.

Example 32

3-Fluoro-5-phenylethynylpyridine

Add phenylacetylene (0.180 mL, 1.6 mmol), copper (I) iodide (0.015 g, 0.08 mmol) bis(triphenylphosphine)palladium (II) dichloride (0.027 g. 0.04 mmol) and triethylamine (0.85 mL, 6 mmol) to a solution of trifluoromethanesulfonic acid 5-fluoro-pyridin-3-yl ester, (prepared essentially as described in PREPARATION 6), (0.367 g, 1.5 mmol) in degassed ethyl acetate (1.5 mL) and heat at 60° C. for 16 h. Cool the reaction mixture to room temperature, filter through diatomaceous earth, wash with ethyl acetate, and concentrate. Purify the residue by silica gel chromatography, eluting with dichloromethane, to give the title compound (0.192 g, 65%).

$^1$H NMR (300 MHz, CDCl$_3$) δ 7.34-7.38 (m, 3 H), 7.48 (s, 1 H), 7.51-7.56 (m, 2 H), 8.44 (br s, 1 H), 8.59 (br s, 1 H); $^{13}$C NMR (75 MHz, CDCl$_3$) δ 85.0, 94.1, 122.4, 125.2, 125.4, 128.9, 129.5, 132.2, 137.4, 137.7, 148.5; MS (ES): m/z=198.1 [M+H]$^+$.

Example 33

3-Trifluoromethyl-5-phenylethynylpyridine

Charge a sealed tube under a positive pressure of argon with bis(acetonitrile)palladium (II) chloride (18 mg, 0.07 mmol), 2-dicyclohexylphosphino diphenyl (73 mg, 0.21 mmol), cesium carbonate (0.557 g, 1.71 mmol) and 3-chloro-5-trifluoromethylpyridine, (prepared essentially as described in PREPARATION 7), (0.12 g, 0.66 mmol) in acetonitrile and stir at room temperature for 25 min (Angew. Chem. Int. Ed. 42, 5993-5996, (2003)). Add phenylacetylene (0.1 mL, 0.86 mmol) and stir at 100° C. for 16 h. Cool to room temperature, dilute with water, and wash twice with ethyl acetate. Combine the ethyl acetate layers, dry (sodium sulfate), and concentrate. Purify the residue by silica gel chromatography, eluting with 100:0 to 50:50 hexanes:dichloromethane, to obtain the title compound (30 mg, 10%).

$^1$H NMR (300 MHz, CDCl$_3$) δ 7.27-7.41 (m, 3 H), 7.54-7.59 (m, 2 H), 8.05 (s, 1 H), 8.81 (s, 1 H), 8.93 (s, 1 H); $^{13}$C NMR (75 MHz, CDCl$_3$) δ 84.7, 94.9, 121.2, 121.7, 122.2, 125.3, 126.8 (q), 128.9, 129.7, 132.2, 135.7, 145.4, 155.4; GC-MS (EI): m/z=247.1 [M].

Example 34

5-(4-Chlorophenylethynyl)-nicotinonitrile

Prepare according to the general procedure outlined in EXAMPLE 10 using 1-chloro-3-iodobenzene (440 mg, 1.85 mmol) to give the title compound (160 mg, 36%).

$^1$H NMR (400 MHz, CDCl$_3$) δ 7.40-7.43 (m, 2H), 7.51-7.53 (m, 2H), 8.10 (t, J=1.8 Hz, 1H), 8.85 (br s, 1H), 8.96 (br s, 1H); HRMS Calcd for C$_{14}$H$_8$ClN$_2$ 239.0376 Found 239.0378; Anal Calcd for C$_{14}$H$_7$ClN$_2$.0.2H$_2$O: C, 69.40; H, 3.08; N, 11.56 Found: C, 69.37; H, 3.10; N, 11.41.

Example 35

5-(2-Methylphenylethynyl)-nicotinonitrile

Prepare essentially as described in EXAMPLE 10 using 2-iodotoluene (510 mg, 2.34 mmol) to give the title compound (143.4 mg, 16%).

$^1$H NMR (300 MHz, CDCl$_3$) δ 2.55 (s, 3H), 7.2-7.4 (m, 3H), 7.54 (d, J=7.92 Hz, 1H), 8.09 (t, J=1.98 Hz, 1H), 8.83 (d, J=1.98 Hz, 1H), 8.95 (d, J=1.65 Hz, 1H); MS (ES): m/z=219 [M+H]$^+$.

Example 36

5-(3-Methylphenylethynyl)-nicotinonitrile

Prepare essentially as described in EXAMPLE 10 using 3-iodotoluene (510 mg, 2.34 mmol) to give the title compound (191.1 mg, 37%).

$^1$H NMR (300 MHz, CDCl$_3$) δ 2.41 (s, 3H), 7.2-7.4 (m, 4H), 8.07-8.08 (m, 1H), 8.82 (s, 1H), 8.95 (s, 1H); MS (ES): m/z=219 [M+H]$^+$.

Example 37

5-(4-Methylphenylethynyl)-nicotinonitrile

Prepare essentially as described in EXAMPLE 10 using 4-iodotoluene (0.51 g, 2.34 mmol) to give the title compound (50 mg, 10%).

$^1$H NMR (300 MHz, CDCl$_3$) δ 2.43 (s, 3H), 7.2-7.5 (m, 4H), 8.06-8.07 (m, 1H), 8.81 (s, 1H), 8.94 (s, 1H); MS (ES): m/z=219 [M+H]$^+$.

Example 38

3-(3-Chlorophenylethynyl)-pyridine hydrochloride

Add triethylamine (0.55 mL, 3.92 mmol), copper (I) iodide (19 mg, 0.098 mmol) and bis(triphenylphosphine)palladium (II) dichloride (35 mg, 0.049 mmol) to a solution of 3-iodopyridine (200 mg, 0.97 mmol) and 1-chloro-3-ethynylbenzene, (prepared essentially as described in PREPARATION 12), (133.7 mg, 0.98 mmol) in ethyl acetate (1 mL). Stir under nitrogen at room temperature for 18 h, filter through diatomaceous earth, wash with ethyl acetate and dichloromethane, and concentrate. Purify the residue by silica gel chromatography, eluting with 100:0 to 0:100 hexanes:dichloromethane. Treat with a 2 M solution of hydrogen chloride in diethyl ether to give the title compound (202 mg, 83%).

$^1$H NMR (300 MHz, CH$_3$OH-d4) δ 7.51 (m, 2H), 7.58 (m, 1H), 7.68 (m, 1H), 8.12 (m, 1H), 8.74 (m, 1H), 8.86 (br s, 1H), 9.13 (br s, 1H); MS (ES): m/z=214 [M+H]$^+$.

Example 39

3-(3-Fluorophenylethynyl)-pyridine hydrochloride

Prepare essentially as described in EXAMPLE 38 using 1-fluoro-3-ethynylbenzene (0.13 mL, 0.98 mmol) to give the title compound (200 mg, 88%).

$^1$H NMR (300 MHz, CH$_3$OH-d4) δ 7.32 (m, 1H), 7.45 (br d, J=9.7 Hz, 1H), 7.53 (m, 2H), 8.03 (br s, 1H), 8.59 (br d, J=8.1 Hz, 1H), 8.91 (br s, 1H), 9.16 (br s, 1H); MS (ES): m/z=198 [M+H]$^+$.

Example 40

3-(3-Methoxyphenylethynyl)-pyridine hydrochloride

Prepare essentially as described in EXAMPLE 38 using 1-methoxy-3-ethynylbenzene (0.12 mL, 0.98 mmol) to give the title compound (200 mg, 83%).

$^1$H NMR (300 MHz, CH$_3$OH-d4) δ 3.84 (s, 3H), 7.07 (m, 1H), 7.19 (m, 1H), 7.23 (br s, 1H), 7.37 (t, J=8.07 Hz, 1H), 8.12 (dd, J=8.07 Hz, 6.06 Hz, 1H), 8.73 (br d, J=8.5 Hz, 1H), 8.84 (br s, 1H), 9.11 (br s, 1H); MS (ES): m/z=210 [M+H]$^+$.

Example 41

3-(3-Methylphenylethynyl)-pyridine hydrochloride

Prepare essentially as described in EXAMPLE 38 using 1-methyl-3-ethynylbenzene (169.9 mg, 1.46 mmol) to give the title compound (170 mg, 51%).

$^1$H NMR (300 MHz, CH$_3$OH-d4) δ 3.27 (s, 3H), 7.26 (br s, 2H), 7.37 (br s, 1H), 7.41 (br s, 1H), 8.06 (br s, 1H), 8.67 (br s, 1H), 8.79 (br s, 1H), 9.04 (br s, 1H); MS (ES): m/z=194 [M+H]$^+$.

Example 42

3-Chloro-5-(3-methoxyphenylethynyl)-pyridine

Prepare essentially as described in EXAMPLE 38 using 1-methoxy-3-ethynylbenzene (0.67 mL 5.27 mmol) to give the title compound (0.320 g, 33%).

$^1$H NMR (300 MHz, CDCl$_3$) δ 3.80 (s, 3H), 6.90 (dd, J=8.5 Hz, 2.8 Hz, 1H), 7.02 (m, 1H), 7.10 (d, J=8.5 Hz, 1H), 7.23 (d, J=8.5 Hz, 1H), 7.77 (t, J=2.0 Hz, 1H), 8.47 (d, J=2.0 Hz, 1H), 8.59 (d, J=2.0 Hz, 1H); MS (ES): m/z=244 [M+H]$^+$.

Example 43

3-(5-Chloropyridin-3-ylethynyl)-benzonitrile

Add cesium carbonate (6.59 g, 20.25 mmol) to a degassed mixture of 3,5-dichloropyridine (1 g, 6.75 mmol), 3-ethynylbenzonitrile, (prepared as described in PREPARATION 8), (1.29 g, 10.12 mmol) 2-dicyclohexylphosphino-2',4',6'-triisopropyl-1,1'-biphenyl (X-PHOS) (96.3 mg, 0.202 mmol) and bis(acetonitrile) palladium (II) chloride (17.5 mg, 0.068). Stir at 110° C. in a sealed tube for 16 h. Cool to room temperature. Quench with water, and extract the product with ethyl acetate. Concentrate and purify the residue by silica gel chromatography, eluting with 100:0 to 100:50 hexanes:ethyl acetate, to give the title compound (300 mg, 19%).

$^1$H NMR (300 MHz, CDCl$_3$) δ 7.51 (t, J=7.7 Hz, 1H), 7.67 (dt, J=7.7 Hz, 1.2 Hz, 1H), 7.75 (dt, J=7.7 Hz, 1.2 Hz, 1H), 7.82 (m, 2H), 8.56 (d, J=2.4 Hz, 1H), 8.64 (d, J=2.4 Hz, 1H); MS (ES): m/z=239 [M+H]$^+$.

Example 44

3-Bromo-5-(3-chlorophenylethynyl)-pyridine

Add triethylamine (2.38 mL, 16.88 mmol), copper (I) iodide (80.4 mg, 0.422 mmol) and bis(triphenylphosphine)palladium (II) dichloride (148 mg, 0.211 mmol) to a solution of 3,5-dibromopyridine (1 g, 4.22 mmol) and 1-chloro-3-ethynylbenzene, (prepared as described in PREPARATION 12), (574 mg, 4.22 mmol) in ethyl acetate (4.22 mL). Stir under nitrogen at 50° C. for 18 h. Concentrate and purify the residue by silica gel chromatography, eluting with 100:0 to 0:100 hexanes:ethyl acetate, to give the title compound (571 mg, 46%).

$^1$H NMR (300 MHz, CDCl$_3$) δ 7.27 (t, J=7.26 Hz, 1H), 7.33 (br d, J=7.26 Hz, 1H), 7.38 (br d, J=7.26 Hz, 1H), 7.49 (br s, 1H), 7.92 (t, J=2.0 Hz, 1H), 8.59 (d, J=2.0 Hz, 1H), 8.62 (d, J=2.0 Hz, 1H); MS (ES): m/z=292 [M+H]$^+$.

Example 45

3-Bromo-5-m-tolylethynylpyridine

Prepare essentially as described in EXAMPLE 44 using 1-methyl-3-ethynylbenzene (0.55 mL, 4.23 mmol) to give the title compound (740 mg, 65%).

$^1$H NMR (300 MHz, CDCl$_3$) δ 2.37 (s, 3H), 7.20 (br d, J=7.7 Hz, 1H), 7.26 (m, 1H), 7.33 (br s, 1H), 7.37 (br s, 1H), 7.96 (br s, 1H), 8.60 (br s, 1H), 8.65 (br s, 1H); MS (ES): m/z=272 [M+H]$^+$.

Example 46

5-(3-Trifluoromethylphenylethynyl)-nicotinonitrile

Add triethylamine (1.93 mL, 13.64 mmol), copper (I) iodide (37.3 mg, 0.190 mmol) and bis(triphenylphosphine) palladium (II) dichloride (120 mg, 0.170 mmol) to a solution of 5-bromonicotinonitrile (624 mg, 3.41 mmol) and 1-ethynyl-3-trifluoromethylbenzene, (prepared essentially as described in PREPARATION 13), (580 mg, 3.41 mmol) in ethyl acetate (3 mL). Stir in a sealed tube at 50° C. for 18 h, concentrate and purify by silica gel chromatography, eluting with 100:0 to 0:100 hexanes:ethyl acetate to give the title compound (400 mg, 43%).

$^1$H NMR (300 MHz, CDCl$_3$) δ 7.54 (t, J=7.7 Hz, 1H), 7.67 (d, J=7.7 Hz, 1H), 7.72 (d, J=7.7 Hz, 1H), 7.83 (s, 1H), 8.08 (t, J=2.0 Hz, 1H), 8.83 (d, J=2.0 Hz, 1H), 8.94 (d, J=2.0 Hz, 1H); $^{13}$C NMR (300 MHz, CDCl$_3$) δ 83.90, 92.48, 108.99, 114.71, 119.56, 121.49, 125.10, 127.63, 128.19, 130.09, 130.53, 133.87, 140.19, 149.96, 154.08.

Example 47

3-(5-Fluoropyridin-3-ylethynyl)-benzonitrile

Add triethylamine (0.79 mL, 5.64 mmol), copper (I) iodide (15.43 mg, 0.08 mmol) and bis(triphenylphosphine)palladium (II) dichloride (49.48 mg, 0.07 mmol) to a solution of trifluoromethanesulfonic acid 5-fluoropyridin-3-ylester, (prepared as described in PREPARATION 6), (345 mg, 1.41 mmol) and 3-ethynylbenzonitrile, prepared as described in PREPARATION 8), (230 mg, 1.41 mmol) in ethyl acetate (2 mL). Stir in a sealed tube at 70° C. for 18 h. Concentrate and purify by silica gel chromatography, eluting with 100:0 to 0:100 hexanes:ethyl acetate, to give the title compound (109 mg, 35%).

$^1$H NMR (300 MHz, CDCl$_3$) δ 7.56-7.48 (m, 2H), 7.66 (dt, J=7.3 Hz, 1.4 Hz, 1H), 7.76 (dt, J=7.3 Hz, 1.4 Hz, 1H), 7.83 (m, 1H), 8.47 (br s, 1H), 8.59 (br s, 1H); MS (ES): m/z =223 [M+H]$^+$.

Example 48

3-(3-Trifluoromethylphenylethynyl)-pyridine hydrochloride

Prepare essentially as described in EXAMPLE 46 using 3-iodopyridine (361 mg, 1.76 mmol). Treat the resulting free base with 2 M hydrogen chloride in diethyl ether to give the title compound (265.5 mg, 94%).

$^1$H NMR (300 MHz, CH$_3$OH-d4) δ 7.68 (t, J=7.3, 1H), 7.79 (d, J=7.3 Hz, 1H), 7.90 (d, J=7.3 Hz, 1H), 7.96 (br s, 1H), 8.14 (br s, 1H), 8.77 (br s, 1H), 8.89 (br s, 1H), 9.17 (br s, 1H); MS (ES): m/z=248 [M+H]$^+$.

Example 49

3-Chloro-5-(3-trifluoromethylphenylethynyl)-pyridine hydrochloride

Prepare essentially as described in EXAMPLE 43 using 1-ethynyl-3-trifluoromethylbenzene, (prepared essentially as described in PREPARATION 13), (300 mg, 1.76 mmol). Treat the resulting free base with 2 M hydrogen chloride in diethyl ether to give the title compound (104 mg, 19%).

$^1$H NMR (300 MHz, CH$_3$OH-d$_4$) δ 7.63 (br t, J=7.3 Hz, 1H), 7.74 (d, J=7.3 Hz, 1H), 7.85 (d, J=7.3 Hz, 1H), 7.91 (br s, 1H), 8.46 (br s, 1H), 8.83 (br s, 1H), 8.89 (br s, 1H); MS (ES): m/z=282 [M+H]$^+$.

Example 50

3-(3,4-Difluorophenylethynyl)-pyridine

Prepare essentially as described in EXAMPLE 46 using 3-iodopyridine (445 mg, 2.17 mmol) and 4-ethynyl-1,2-difluorobenzene, (prepared essentially as described in PREPARATION 14), (300 mg, 2.17 mmol) to give the title compound (87.6 mg, 21%).

$^1$H NMR (300 MHz, CH$_3$OH-d4) δ 7.42-7.34 (m, 1H), 7.48 (m, 1H), 7.61 (m, 1H), 8.13 (t, J=8.0 Hz, 1H), 8.72 (d, J=8.0 Hz, 1H), 8.88 (br s, 1H), 9.14 (br s, 1H); MS (ES): m/z=216 [M+H]$^+$.

Example 51

3-Fluoro-5-(3-trifluoromethylphenylethynyl)-pyridine hydrochloride

Prepare essentially as described in EXAMPLE 47 using 1-ethynyl-3-trifluoromethylbenzene, (prepared essentially as described in PREPARATION 13), (51.3 mg, 0.302 mmol), Treat the resulting free base with 2 M hydrogen chloride in diethyl ether in to give the title compound (20 mg, 22%).

$^1$H NMR (300 MHz, CH$_3$OH-d4) δ 7.64 (t, J=7.3 Hz, 1H), 7.74 (d, J=7.3 Hz, 1H), 7.85 (d, J=7.3 Hz, 1H), 7.91 (br s, 1H), 8.08 (br d, J=8.8 Hz, 1H), 8.66 (br s, 1H), 8.73 (br s, 1H); MS (ES): m/z=266 [M+H]$^+$.

Example 52

3-Methyl-5-(3-trifluoromethylphenylethynyl)-pyridine hydrochloride

Add cesium carbonate (267 mg, 0.82 mmol) and tetrakis (triphenylphosphine) palladium (95 mg, 0.082 mmol) to a solution of 3-bromo-5-(3-trifluoromethyl-phenylethynyl)-pyridine, (prepared essentially as described in EXAMPLE 55), (265 mg, 0.82 mmol), and trimethylboroxine (0.03 mL, 0.20 mmol) in 10% aqueous 1,4-dioxane. Stir at 80° C. for 16 h. Quench with 10% aqueous hydrochloric acid, neutralize with a saturated sodium bicarbonate solution and extract with ethyl acetate. Dry (magnesium sulfate), concentrate and purify by silica gel chromatography, eluting with 100:0 to 0:100 hexanes:ethyl acetate. Treat the resulting free base with a 2 M hydrogen chloride solution in diethyl ether to give the title compound (56.1 mg, 30%).

$^1$H NMR (300 MHz, CH$_3$OH-d4) δ 2.60 (s, 3H), 7.65 (br s, 1H), 7.75 (m, 1H), 7.91 (m, 1H), 8.62 (br s, 1H), 8.73 (br s 1H), 8.95 (br s, 1H); MS (ES): m/z=262 [M+H]$^+$.

Example 53

3-(5-Methylpyridin-3-ylethynyl)-benzonitrile

Prepare essentially as described in EXAMPLE 52 using 3-(5-bromopyridin-3-ylethynyl)-benzonitrile (445 mg, 2.17 mmol), (prepared as described in EXAMPLE 56) to give the title compound (75 mg, 28%).

$^1$H NMR (300 MHz, CH$_3$OH-d4) δ 2.39 (s, 3H), 7.60 (t, J=8.1 Hz, 1H), 7.76 (d, J=8.1 Hz, 1H), 7.84 (m, 2H), 7.93 (br s, 1H), 8.40 (br s, 1H), 8.52 (br s, 1H); MS (ES): m/z=219 [M+H]$^+$.

Example 54

3-(3,4-Difluorophenylethynyl)-5-methylpyridine

Prepare essentially as described in EXAMPLE 52 using 3-bromo-5-(3,4-difluorophenylethynyl)-pyridine (363 mg, 1.24 mmol), (prepared as described in EXAMPLE 100), to give the title compound (80 mg, 28%).

$^1$H NMR (300 MHz, CDCl$_3$) δ 2.35 (s, 3H), 7.19-7.11 (m, 1H), 7.37-7.25 (m, 2H), 7.62 (br s, 1H), 8.40 (br s, 1H), 8.56 (br s, 1H); MS (ES): m/z=230 [M+H]$^+$.

Example 55

3-Bromo-5-(3-trifluoromethylphenylethynyl)-pyridine

Add triethylamine (6.2 mL, 44 mmol), copper (I) iodide (120.3 mg, 1.10 mmol) and bis(triphenylphosphine)palladium (II) dichloride (386 mg, 0.55 mmol) to a solution of 3-bromo-5-ethynylpyridine, (prepared essentially as described in PREPARATION 23), (2.0 g, 11 mmol) and 1-iodo-3-trifluoromethylbenzene (1.53 mL, 11 mmol) in ethyl acetate (12 mL). Stir at room temperature for 18 h. Concentrate and purify the residue by silica gel chromatography, eluting with 100:0 to 100:50 hexanes:ethyl acetate to give the title compound (2.1 g, 61%).

$^1$H NMR (300 MHz, CDCl$_3$) δ 7.52 (t, J=8.0 Hz, 1H), 7.64 (d, J=8.0 Hz, 1H), 7.71 (d, J=8.0 Hz, 1H), 7.80 (br s, 1H), 7.98 (t, J=2.2 Hz, 1H), 8.64 (d, J=2.2 Hz, 1H), 8.68 (d, J=2.2 Hz, 1H); MS (ES): m/z=326 [M+H]$^+$.

Example 56

3-(5-Bromopyridin-3-ylethynl)-benzonitrile

Combine 3-iodobenzonitrile (884 mg, 3.86 mmol), bis (triphenylphosphine)-palladium (II) chloride (0.135 g, 0.193 mmol), copper (I) iodide (74 mg, 0.386 mmol), triethylamine (7.5 mL, 54.0 mmol) and (trimethylsilyl)acetylene (0.57 mL, 4.05 mmol). Heat to 80° C. for 3 h. Cool to −78° C. and treat with bis(triphenylphosphline)palladium (II) dichloride (135 mg, 0.193 mmol), copper (I) iodide (74 mg, 0.386 mmol), a 1 M solution of tetrabutylammonium fluoride in tetrahydrofuran (3.93 mL, 3.93 mmol) and 3,5-dibromopyridine (1.1 g, 4.6 mmoles). After 5 min remove the cooling bath and heat at 80° C. for 2 h. Cool to room temperature and stir overnight. Dilute the reaction with ethyl acetate and wash with an aqueous saturated solution of sodium bicarbonate and an aqueous saturated solution of sodium chloride. Dry (sodium sulfate), filter, concentrate and purify (silica gel chromatography, eluting with 85:15 to 80:20 hexanes:ethyl acetate) to give the title compound (382 mg, 35%).

$^1$H NMR (400 MHz, CDCl$_3$) δ 7.51 (t, J=7.7 Hz, 1H), 7.67 (d, J=7.9 Hz, 1H), 7.75 (d, J=7.5 Hz, 1H), 7.82 (s, 1H), 7.99 (s, 1H), 8.68 (s, 2H); MS (ES): m/z=283.0, 285.0 [M+H]$^+$.

Example 57

3-Bromo-5-(3-methoxyphenylethynyl)-pyridine

Combine 3-iodoanisole (0.50 mL, 4.2 mmol) bis(triphenylphosphine)palladium (II) dichloride (147 mg, 0.21 mmol), copper (I) iodide (80 mg, 0.42 mmol) in triethylamine (8.2 mL, 59 mmoles) and add (trimethylsilyl)acetylene (0.62 mL, 4.4 mmol). Heat to 80° C. in a sealed tube for 3 h. Cool to −78° C. and treat with additional bis(triphenylphosphine) palladium (II) dichloride (147 mg, 0.21 mmol) and copper (I) iodide (80 mg, 0.42 mmol) followed by a 1 M solution of tetrabutylammonium fluoride in tetrahydrofuran (4.3 mL, 4.2 mmol) and 3,5-dibromopyridine (1.1 g, 4.6 mmoles). After 5 min remove the cooling bath and stir at room temperature overnight. Heat to 80° C. in a sealed tube for 2 h. Cool to room temperature, dilute with ethyl acetate, wash with an aqueous saturated solution of sodium bicarbonate, an aqueous saturated solution of sodium chloride, dry (sodium sulfate), filter, concentrate and purify (silica gel chromatography, eluting with 80:15:5 hexanes:dichloromethane:ethyl acetate) to give the title compound (544 mg, 44%).

$^1$H NMR (400 MHz, CDCl$_3$) δ 3.83 (s, 3H), 6.95 (ddd, J=8.3, 2.7, 0.8 Hz, 1H), 7.06-7.05 (m, 1H), 7.15-7.12 (m, 1H), 7.29 (t, J=8.1 Hz, 1H), 7.99 (t, J=1.8 Hz, 1H), 8.63 (d, J=1.8 Hz, 1H), 8.68 (s, 1H); HRMS Calcd for C$_{14}$H$_{11}$BrNO 288.0024 Found 288.0046; Anal Calcd for C$_{14}$H$_{10}$BrNO: C, 58.36; H, 3.50; N, 4.86 Found: C, 58.21; H, 3.69; N, 4.76.

Example 58

5-(3,4-Difluorophenylethynyl)-nicotinonitrile

Prepare according to the general procedure outlined in EXAMPLE 10 using 3,4-difluoroiodobenzene (0.25 mL, 2.05 mmol). Purify the crude material by silica gel chromatography, eluting with 85:15 hexanes:ethyl acetate, and then further purify on C-18 silica, eluting from 60:40 to 20:80 (0.1% aqueous solution of trifluoroacetic acid):(0.1% solution of trifluoroacetic acid in acetonitrile). Concentrate the desired fractions, partition the residue between ethyl acetate and an aqueous saturated solution of sodium bicarbonate and separate the layers. Wash the organic layer with an aqueous saturated solution of sodium chloride, dry (sodium sulfate), filter and concentrate to give the title compound as a white solid (265 mg, 56%).

$^1$H NMR (400 MHz, CDCl$_3$) δ 7.23-7.17 (m, 1H), 7.33-7.29 (m, 1H), 7.38 (ddd, J=10.5, 7.5, 2.2 Hz, 1H), 8.06 (t, J=2.0 Hz, 1H), 8.83 (s, 1H), 8.92 (s, 1H). HRMS Calcd for C$_{14}$H$_7$F$_2$N$_2$ 241.0577 Found 241.0602; Anal Calcd for C$_{14}$H$_6$F$_2$N$_2$: C, 70.00; H, 2.52; N, 11.66 Found: C, 70.22; H, 2.65; N, 11.43.

Example 59

5-(3,5-Difluorophenylethynyl)-nicotinonitrile

Prepare according to the general procedure outlined in EXAMPLE 10 using 3,5-difluorobromobenzene (0.24 mL, 2.05 mmol). Purify the crude material by silica gel chromatography, eluting with 85:15 hexanes:ethyl acetate, and then further purify on C-18 silica, eluting from 60:40 to 20:80 (0.1% aqueous solution of trifluoroacetic acid):(0.1% solution of trifluoroacetic acid in acetonitrile). Concentrate the desired fractions, partition the residue between ethyl acetate and an aqueous saturated solution of sodium bicarbonate and separate the layers. Wash the organic layer with an aqueous saturated solution of sodium chloride, dry (sodium sulfate), filter and concentrate to give the title compound as a white solid (79 mg, 17%).

$^1$H NMR (400 MHz, DMSO-d$_6$) δ 7.45-7.35 (m, 3H), 8.56 (t, J=2.0 Hz, 1H), 9.01 (d, J=1.8 Hz, 1H), 9.03 (d, J=2.2 Hz, 1H); HRMS Calcd for C$_{14}$H$_7$F$_2$N$_2$ 241.0577 Found 241.0587; Anal Calcd for C$_{14}$H$_6$F$_2$N$_2$: C, 70.00; H, 2.52; N, 11.66 Found: C, 69.08; H, 2.80; N, 11.07.

Example 60

5-(3,4,5-Trifluorophenylethynyl)-nicotinonitrile

Prepare according to the general procedure outlined in EXAMPLE 10 using 3,4,5-difluorobromobenzene (0.24 mL, 2.05 mmol). Purify using C-18 silica, eluting from 60:40 to 20:80 (0.1% aqueous solution of trifluoroacetic acid):(0.1% solution of trifluoroacetic acid in acetonitrile). Concentrate the desired fractions, partition the residue between ethyl acetate and an aqueous saturated solution of sodium bicarbonate and separate the layers. Wash the organic layer with an aqueous saturated solution of sodium chloride, dry (sodium sulfate), filter and concentrate to give the title compound (70 mg, 14%) as a white solid.

$^1$H NMR (400 MHz, CDCl$_3$) δ 7.20-7.13 (m, 2H), 8.04 (t, J=2.0 Hz, 1H), 8.81 (d, J=1.8 Hz, 1H), 8.89 (d, J=2.2 Hz, 1H); HRMS Calcd for C$_{14}$H$_6$F$_3$N$_2$ 259.0483 Found 259.0482; Anal Calcd for C$_{14}$H$_5$F$_3$N$_2$: C, 65.12; H, 1.95; N, 10.85 Found: C, 64.78; H, 2.06; N, 10.72.

Example 61

3-(5-Methoxypyridin-3-ylethynyl)-benzonitrile

Prepare essentially as described in PREPARATION 10 using 3-iodobenzonitrile (681 mg, 3.0 mmol) and 3-ethynyl-5-methoxypyridine from PREPARATION 10 (415 mg, 3.1 mmol) at room temperature for 16 h to give the title compound (564 mg, 68%).

$^1$H NMR (300 MHz, CDCl$_3$) δ 3.87 (s, 3H), 7.30 (dd; J=1.5 Hz, 1H), 7.48 (t, J=7.9 Hz, 1H), 7.62 (dt, J=8.0 and 1.5 Hz, 1H), 7.74 (dt, J=8.0 and 1.5 Hz, 1H), 7.81 (br s, 1H), 8.29 (d, J=2.9 Hz, 1H), 8.36 (d, J=1.5 Hz, 1H); LC-MS (ES): m/z=235.0 [M+H]$^+$.

Example 62

(E) 5-[2-(3-Bromophenyl)-vinyl]-nicotinonitrile

Prepare essentially as described in EXAMPLE 15 using palladium(II) acetate (10 mg, 0.04 mmol), tri-o-tolylphosphine (27 mg, 0.09 mmol) and 1-bromo-3-vinylbenzene (0.570 mL, 4.37 mmol) at 120° C. for 18 h to give the title compound (30 mg, 5%).

$^1$H NMR (300 MHz, CDCl$_3$) δ 7.05 (d, J=16.1 Hz, 1H), 7.15 (d, J=16.1 Hz, 1H), 7.28 (t, J=8.0 Hz, 1H), 7.43-7.49 (m, 2H), 7.69 (t, J=1.7 Hz, 1H), 8.07 (t, J=1.8 Hz, 1H), 8.76 (d, J=1.5 Hz, 1H), 8.90 (d, J=2.1 Hz, 1H); LC-MS (ES): m/z=285.0, 287.0 [M+H]$^+$.

Example 63

(E) 5-[2-(3-Cyanophenyl)-vinyl]-nicotinonitrile

Prepare essentially as described in EXAMPLE 15 using palladium(II) acetate (0.009 g, 0.04 mmol), tri-o-tolylphosphine (0.024 g, 0.08 mmol), copper (I) iodide (0.004 g, 0.02 mmol), 3-iodobenzonitrile (0.9 g, 3.93 mmol) and 5-vinylnicotinonitrile, (prepared essentially as described in PREPARATION 51), (0.715 g, 5.5 mmol) at 110° C. for 5 h. Add diethyl ether and wash with water three times. Filter the organic layer and concentrate to give the title compound (0.530g, 59%).

$^1$H NMR (300 MHz, CDCl$_3$) δ 7.11 (d, J=16.8 Hz, 1H), 7.21 (d, J=16.8 Hz, 1H), 7.53 (t, J=7.7 Hz, 1H), 7.63 (br d, J=7.3 Hz, 1H), 7.76 (br d, J=7.3 Hz, 1H), 7.82 (br s, 1H), 8.10 (t, J=2.2 Hz, 1H), 8.79 (d, J=1.5 Hz, 1H), 8.92 (d, J=2.2 Hz, 1H); LC-MS (ES): m/z=232.1 [M+H]$^+$.

Example 64

(E) 5-[2-(3-Chlorophenyl)-vinyl]-nicotinonitrile

Prepare essentially as described in EXAMPLE 15 using palladium(II) acetate (7 mg, 0.03 mmol), tri-o-tolylphosphine (20 mg, 0.07 mmol) and 1-chloro-3-vinylbenzene (0.340 mL, 2.68 mmol) at 120° C. for 58 h to give the title compound (55 mg, 14%).

$^1$H NMR (300 MHz, CDCl$_3$) δ 7.05 (d, J=16.8 Hz, 1H), 7.17 (d, J=16.1 Hz, 1H), 7.32-7.34 (m, 2H), 7.37-7.42 (m, 1H), 7.53 (s, 1H), 8.07 (t, J=2.2 Hz, 1H), 8.76 (br s, 1H), 8.90 (br s, 1H); LC-MS (ES): m/z=241.0, 243.0 [M+H]$^+$.

Example 65

(E) 5-[2-(2-Chlorophenyl)-vinyl]-nicotinonitrile

Prepare essentially as described in EXAMPLE 15 using the dichloromethane complex of 1,1'-bis(diphenylphosphino)ferrocenedichloropalladium(II) (67 mg, 0.08 mmol) and 1-chloro-2-vinylbenzene (0.315 mL, 2.46 mmol) for 20 h to give the title compound (18 mg, 5%).

$^1$H NMR (300 MHz, CDCl$_3$) δ 7.04 (d, J=16.4 Hz, 1H), 7.29 (d, J=12.1 Hz, 1H), 7.28-7.33 (m, 1H), 7.43-7.46 (m, 1H), 7.63-7.70 (m, 2H), 8.12 (t, J=1.8 Hz, 1H), 8.78 (br s, 1H), 8.94 (br s, 1H); LC-MS (ES): m/z=241.1, 243.1 [M+H]$^+$.

Example 66

3-(4-Fluorophenylethynyl)-pyridine

Prepare essentially as described in PREPARATION 10 using 3-iodopyridine (153 mg, 0.75 mmol) and 1-ethynyl-4-fluorobenzene (100 mg, 0.83 mmol) to give the title compound (60 mg, 40%).

$^1$H NMR (300 MHz, CDCl$_3$) δ 7.06 (tt, J=6.6 and 2.2 Hz, 1H), 7.28 (dd, J=7.8 and 5.0 Hz, 1H), 7.50-7.55 (m, 1H), 7.79 (dt, J=7.7 and 1.7 Hz, 1H), 8.55 (dd, J=2.9 Hz, 1H), 8.75 (d, J=5.1 and 1.5 Hz, 1H); LC-MS (ES): m/z=198.1 [M+H]$^+$.

Example 67

3-(4-Fluorophenylethynyl)-5-methylpyridine

Prepare essentially as described in PREPARATION 10 using 3-bromo-5-methylpyridine, (prepared as described in PREPARATION 1), (196 mg, 1.14 mmol) and 1-ethynyl-4-fluorobenzene (150 mg, 1.25 mmol) to give the title compound (60 mg, 25%).

$^1$H NMR (300 MHz, CDCl$_3$) δ 2.39 (s, 1H), 7.05 (tt, J=8.6 Hz, 2H), 7.46-7.52 (m, 2H), 7.67 (br s, 1H); LC-MS (ES): m/z=212.1 [M+H]$^+$.

Example 68

5-(3-Nitrophenylethynyl)-nicotinonitrile

Prepare essentially as described in PREPARATION 10 using 5-bromonicotinonitrile (400 mg, 2.19 mmol) and 1-ethynyl-3-nitrobenzene, (prepared as described in PREPARATION 11), (644 mg, 4.38 mmol) to give the title compound (118 mg, 65%).

$^1$H NMR (300 MHz, CDCl$_3$) δ 3.87 (s, 3H), 7.31 (dd, J=1.5 Hz, 1H), 7.49 (t, J=7.6 Hz, 1H), 7.61 (d, J=8.0 Hz, 1H), 7.74 (d, J=8.0 Hz, 1H), 7.80 (br s, 1H), 8.29 (d, J=3.0 Hz, 1H), 8.38 (d, J=1.5 Hz, 1H); LC-MS (ES): m/z=278.1 [M+H]$^+$.

Example 69

3-Methoxy-5-(3-trifluoromethyl-phenylethynyl)-pyridine

Prepare essentially as described in PREPARATION 10 using 1-iodo-3-trifluoromethylbenzene (0.430 mL, 3.0 mmol) and 3-ethynyl-5-methoxypyridine, (prepared essentially as described in PREPARATION 10), (415 mg, 3.1 mmol) at room temperature for 16 h to give the title compound (541 mg, 65%).

$^1$H NMR (300 MHz, CDCl$_3$) δ 3.87 (s, 3H), 7.31 (dd, J=1.5 Hz, 1H), 7.49 (t, J=7.6 Hz, 1H), 7.61 (d, J=8.0 Hz, 1H), 7.74 (d, J=8.0 Hz, 1H), 7.80 (br s, 1H), 8.29 (d, J=3.0 Hz, 1H), 8.38 (d, J=1.5 Hz, 1H); LC-MS (ES): m/z=278.1 [M+H]$^+$.

Example 70

(E) 5-[2-(4-Fluorophenyl)-vinyl]-nicotinonitrile

Prepare essentially as described in EXAMPLE 15 using palladium(II) acetate (10 mg, 0.04 mmol), tri-o-tolylphosphine (24 mg, 0.08 mmol), copper (I) iodide (2 mg, 0.01 mmol), and 1-fluoro-4-vinylbenzene (0.480 mL, 4.0 mmol) at 120° C. for 27 h to give the title compound (101 mg, 23%).

$^1$H NMR (300 MHz, CDCl$_3$) δ 6.96 (d, J=16.1 Hz, 1H), 7.20 (d, J=16.8 Hz, 1H), 7.10 (t, J=8.8 Hz, 2H), 7.50-7.54 (m, 2H), 8.06 (t, J=1.8 Hz, 1H), 8.73 (d, J=1.5 Hz, 1H), 8.88 (d, J=2.2 Hz, 1H); LC-MS (ES): m/z=225.1 [M+H]$^+$.

Example 71

5-(3-Aminophenylethynyl)-nicotinonitrile

Prepare according to the general procedure outlined in EXAMPLE 30 using 3-ethynylaniline (1.0 g, 8.5 mmol) and 5-bromonicotinonitrile (1.56 g, 8.54 mmol) to give the title compound (0.7 g, 38%).

$^1$H NMR (400 MHz, DMSO-d$_6$) δ 6.64 (ddd, J=8.1 Hz, 2.4 Hz, 1.1 Hz, 1H), 6.70 (td, J=7.6 Hz, 1.3 Hz, 1H), 6.74 (t, J=1.8 Hz, 1H), 7.07 (t, J=7.7 Hz, 1H), 8.52 (t, J=2.0 Hz, 1H), 8.97 (d, J=1.8 Hz, 1H), 8.99 (d, J=1.8 Hz, 1H); MS (ES): m/z=220 [M+H]$^+$.

Example 72

5-(3-Chloro-4-fluorophenylethynyl)-nicotinonitrile

Stir 5-trimethylsilanylethynyl-nicotinonitrile (300 mg, 1.5 mmol), (prepared essentially as described in PREPARATION 3), 2-chloro-1-fluoro-4-iodobenzene (390 mg, 1.5 mmol), bis(triphenylphosphine)palladium (II) dichloride (50 mg, 0.08 mmol) and copper (I) iodide (20 mg, 0.15 mmol) in triethylamine (15 mL) under nitrogen and cool to −78° C. Add a 1 M solution of tetrabutylammonium fluoride (1.5 mL) in tetrahydrofuran and warm to room temperature and then heat at 70° C. until complete by thin layer chromatography. Concentrate and purify the residue by silica gel chromatography, eluting with hexanes:ethyl acetate, and then recrystallize from hexanes:ethyl acetate to give the title compound (120 mg, 31%).

$^1$H NMR (400 MHz, CDCl$_3$) δ 7.18 (t, J=8.8 Hz, 1H), 7.46-7.42 (m, 1H), 7.62 (dd, J=6.8 Hz, 2.0 Hz, 1H), 8.06 (t, J=2.2 Hz, 1H), 8.82 (d, J=1.8 Hz, 1H), 8.91 (d, J=2.2 Hz, 1H); HRMS calcd for C$_{14}$H$_7$ClFN$_2$ 257.0282 Found 257.0266; Anal. Calcd for C$_{14}$H$_6$ClFN$_2$: C, 65.52; H, 2.37; N, 10.91 Found: C, 65.59; H, 2.48; N, 10.67.

Example 73

5-(3-Hydroxyphenylethynyl)-nicotinonitrile

Prepare essentially as described in EXAMPLE 10 using 3-iodophenol (0.69 g, 3.0 mmol) and 5-ethynylnicotinonitrile (0.4 g, 3.0 mmol) to give the title compound (110 mg, 17%).

$^1$H NMR (400 MHz, CDCl$_3$) δ 6.84 (ddd, J=8.1 Hz, 2.4 Hz, 1.1 Hz, 1H), 6.92 (t, J=2.0 Hz, 1H), 6.99 (td, J=7.6 Hz, 1.1 Hz, 1H), 7.22 (t, J=7.9 Hz, 1H), 8.51 (t, J=2.2 Hz, 1H), 8.97 (t, J=1.8 Hz, 2H), 9.76 (s, 1H); MS (ES): m/z=219 [M−H]$^+$.

Example 74

5-(3-Acetylphenylethynyl)-nicotinonitrile

Prepare according to the general procedure outlined in EXAMPLE 72 using 3'-iodoacetophenone (1.29 g, 5.24 mmol) and 5-trimethylsilanylethynyl-nicotinonitrile (1.0 g, 5.0 mmol), (prepared as described in PREPARATION 3), to give the title compound (600 mg, 49%).

$^1$H NMR (400 MHz, CDCl$_3$) δ 2.65 (s, 3H), 7.52 (t, J=7.5 Hz, 1H), 7.74 (td, J=7.6 Hz, 1.4 Hz, 1H), 8.00 (td, J=7.9 Hz, 1.5 Hz, 1H), 8.09 (t, J=2.0 Hz, 1H), 8.83 (d, J=2.2 Hz, 1H), 8.94 (d, J=2.2 Hz, 1H). MS (ES): m/z=247 [M+H]$^+$; HRMS calcd for C$_{16}$H$_{11}$N$_2$O 247.0871 Found 247.0860; Anal. Calcd for C$_{16}$H$_{10}$N$_2$O: C, 78.04; H, 4.09; N, 11.38 Found: C, 77.77; H, 4.13; N, 11.29.

Example 75

5-(5-Chloro-2-methoxyphenylethynyl)-nicotinonitrile

Prepare according to the general procedure outlined in EXAMPLE 72 using 4-chloro-2-iodo-1-methoxybenzene (510 mg, 1.9 mmol) and 5-trimethylsilanyl-ethynylnicotinonitrile (350 mg, 1.75 mmol), (prepared as described in PREPARATION 3), to give the title compound (260 mg, 53%).

$^1$H NMR (400 MHz, CDCl$_3$) δ 3.88 (s, 3H), 6.84 (d, J=8.8 Hz, 1H), 7.31 (dd, J=8.8 Hz, 2.6 Hz, 1H), 7.44 (d, J=2.6 Hz, 1H), 8.05 (t, J=2.2 Hz, 1H), 8.77 (s, 1H), 8.90 (s, 1H); HRMS calcd for C$_{15}$H$_{10}$CN$_2$O 269.0482 Found 269.0471.

Example 76

5-(3-Chloro-4-methoxyphenylethynyl)-nicotinonitrile

Prepare according to the general procedure outlined in EXAMPLE 72 using 2-chloro-4-iodo-1-methoxybenzene (520 mg, 19 mmol) and 5-trimethylsilanylethynyl-nicotinonitrile (350 mg, 1.75 mmol), (prepared as described in PREPARATION 3), to give the title compound (820 mg, 47%).

$^1$H NMR (400 MHz, CDCl$_3$) δ 3.92 (s, 3H), 6.91 (d, 1H, J=8.4 Hz), 7.41 (dd, 1H, J=8.8, 2.2 Hz), 7.55 (d, 1H, J=1.8 Hz), 8.01 (t, 1H, J=2.0 Hz), 8.76 (d, 1H, J=2.2 Hz), 8.86 (d, 1H, J=2.2 Hz); HRMS calcd for C$_{15}$H$_{10}$ClN$_2$O 269.0482 Found 269.0471.

Example 77

5-(3-Hydroxy-4-fluorophenylethynyl)-nicotinonitrile

Add bis(phenylnitrile)palladium (II) chloride (115 mg, 0.3 mmol) to a suspension of copper (I) iodide (38 mg, 0.2 mmol) in anhydrous 1,4-dioxane (1 mL) under nitrogen and stir for 10 min. Sequentially add 5-ethynyl-nicotinonitrile (1.28 g, 10 mmol), (prepared essentially as described in PREPARATION 4), 2-fluoro-5-iodophenol, (prepared essentially as described in PREPARATION 15), (2.37 g, 10 mmol) and tri-tert-butylphosphine (121 mg, 0.6 mmol) in 1,4-dioxane (5 mL) and diethylamine (2.1 mL, 12 mmol) to the reaction mixture and heat at 60° C. for 16 h. Cool to room temperature, dilute with diethyl ether, stir for 10 min and filter through diatomaceous earth. Wash the filtrate sequentially with water and an aqueous saturated solution of sodium chloride. Dry (magnesium sulfate), concentrate and purify by silica gel chromatography, eluting with 0:100 to 35:100 ethyl acetate:hexanes, to give the title compound (1.0 g, 42%) as a yellow solid.

$^1$H NMR (400 MHz, DMSO-d$_6$) δ 7.03 (m, 1H), 7.13 (dd, J=8 Hz, 2 Hz, 1H), 7.22 (dd, J=11 Hz, 8 Hz, 1H), 8.53 (t, J=2 Hz, 1H), 8.90 (d, J=2 Hz, 1H), 8.99 (d, J=2 Hz, 1H), 10.30 (s, 1H); LC-MS (ES): m/z 239.3 [M+H]$^+$.

Example 78

5-(4-Fluoro-3-methoxyphenylethynyl)-nicotinonitrile

Dissolve 5-(3-hydroxy-4-fluorophenylethynyl)-nicotinonitrile, (prepared essentially as described in EXAMPLE 77), (150 mg, 0.63 mmol) in anhydrous acetonitrile (5 mL) and sequentially add iodomethane (59 μL, 0.95 mmol) and potassium carbonate (174 mg, 1.26 mmol). Stir at room temperature for 12 h, dilute with an aqueous saturated solution of sodium carbanate and extract with dichloromethane. Sequentially wash the organic layer with water and an aqueous saturated solution of sodium chloride, dry (magnesium sulfate), filter and concentrate. Purify by silica gel chromatography, eluting with 30:70 ethyl acetate:hexanes, to give the title compound (70 mg, 44%) as white solid.

$^1$H NMR (400 MHz, CDCl$_3$) δ 3.92 (s, 3H), 7.13-7.05 (m, 3H), 8.05 (t, J=1.8 Hz, 1H), 8.81 (d, J=2 Hz, 1H), 8.92 (d, J=2 Hz, 1H); LC-MS (ES): m/z=253 [M+H]$^+$.

Example 79

5-(4-Fluoro-3-ethoxyphenylethynyl)-nicotinonitrile

Prepare according to the general procedure outlined in EXAMPLE 78 using bromoethane (104 mg, 71 μL, 0.95 mmol) to give the title compound (71 mg, 42%).

$^1$H NMR (400 MHz, CDCl$_3$) δ 1.48 (t, J=7.1 Hz, 3H), 4.13 (q, J=7.1 Hz, 2H), 7.13-7.05 (m, 3H), 8.04 (t, J=2 Hz, 1H), 8.79 (d, J=1.8 Hz, 1H), 8.90 (d, J=1.8 Hz, 1H); LC-MS (ES): m/z=267 [M+H]$^+$.

Example 80

5-(4-Fluoro-3-isopropoxyphenylethynyl)-nicotinonitrile

Prepare according to the general procedure outlined in EXAMPLE 78 using 2-iodopropane (214 mg, 125 μL, 1.26 mmol) to give the title compound (138 mg, 78%).

$^1$H NMR (400 MHz, CDCl$_3$) δ 1.39 (d, J=5.0 Hz, 6H), 4.57 (q, J=5.0 Hz, 1H), 7.17-7.04 (m, 3H), 8.04 (t, J=2 Hz, 1H), 8.79 (d, J=1.8 Hz, 1H), 8.91 (d, J=1.8 Hz, 1H); MS (ES): m/z=281.2 [M+H]$^+$.

Example 81

5-(3-Isopropylphenylethynyl)-nicotinonitrile

Prepare according to the general procedure outlined in EXAMPLE 77 using 1-bromo-3-isopropylbenzene (199 mg, 1.0 mmol) to give the title compound (191 mg, 78%).

$^1$H NMR (400 MHz, CDCl$_3$) δ 1.27 (d, J=5.0 Hz, 6H), 2.93 (q, J=5.0 Hz, 1H), 7.42-7.27 (m, 4H), 8.05 (t, J=1.8 Hz, 1H), 8.78 (d, J=2.0 Hz, 1H), 8.91 (d, J=2.0 Hz, 1H); LC-MS (ES): m/z=247 [M+H]$^+$.

Example 82

5-(3-Ethylphenylethynyl)-nicotinonitrile

Prepare according to the general procedure outlined in EXAMPLE 77 using 1-bromo-3-ethylbenzene (185 mg, 1.0 mmol) to give the title compound (52 mg, 22%).

$^1$H NMR (400 MHz, CDCl$_3$) δ 1.26 (t, J=5.5 Hz, 3H), 2.67 (q, J=5.5 Hz, 2H), 7.39-7.42 (m, 4H), 8.05 (t, J=1.8 Hz, 1H), 8.85 (d, J=2.0 Hz, 1H), 8.90 (d, J=2.0 Hz, 1H); LC-MS (ES): m/z=233 [M+H]$^+$.

Example 83

3-(4-Fluorophenylethynyl)-5-iodopyridine

Add a 2 M solution of isopropylmagnesium chloride in tetrahydrofuran (81 mL, 161.7 mmol) to a solution of 3-bromo-5-(4-fluorophenylethynyl)-pyridine, (prepared essentially as described in PREPARATION 24), (40.5 g, 147 mmol) in anhydrous tetrahydrofuran (400 mL) at room temperature under nitrogen. Stir for 1 h, add a solution of iodine (41 g, 161.7 mmol) in anhydrous tetrahydrofuran (250 mL) and stir for an additional 16 h. Add water (200 mL) to the reaction mixture, dilute with diethyl ether (400 mL) and separate the layers. Sequentially wash the organic layer with a 10% aqueous solution of sodium thiosulfate (150 mL), water (200 mL) and an aqueous saturated solution of sodium chloride, dry (magnesium sulfate), filter and concentrate. Purify by silica gel chromatography, eluting with 15:1 hexanes:ethyl acetate, to give the title compound as a pale yellow solid (25.4 g, 53%).

$^1$H NMR (300 MHz, CDCl$_3$) δ 8.75 (d, J=2.0 Hz, 1H), 8.66 (d, J=2.0 Hz, 1H), 8.13 (t, J=2.2 Hz, 1H), 7.52 (m, 1H), 7.07 (t, J=8.9 Hz, 1H); LC-MS (ES): m/z=324 [M+H]$^+$.

Example 84

1-(5-Phenylethynylpyridin-3-yl)-ethanone

Add methylmagnesium bromide (1.25 mL, 3.7 mmol) dropwise at 0° C. to a solution of N-methoxy-N-methyl-5-phenylethynylnicotinamide, (prepared essentially as described in PREPARATION 2), (1.0 g, 3.76 mmol). Allow the mixture to warm to room temperature overnight. Dilute with ethyl acetate and saturated ammonium chloride, dry (magnesium sulfate), concentrate and purify (silica gel chromatography, eluting with 10:90 to 30:70 tetrahydrofuran:hexanes) to give title compound as a white solid (0.70 g, 84%).

$^1$H NMR (400 MHz, CDCl$_3$) δ 2.66 (s, 3H), 7.42-7.36 (m, 3H), 7.53 (m, 2H), 8.34 (t, J=2.2 Hz, 1H), 8.91 (d, J=1.8 Hz, 1H), 9.08 (d, J=1.8 Hz, 1H); MS (ES): m/z=222 [M+H]$^+$.

Example 85

1-(5-Phenylethynyl-pyridin-3-yl)-ethanone O-methyloxime hydrochloride

Prepare essentially as described in EXAMPLE 6 using methoxylamine hydrochloride (700 mg, 8.4 mmol), 1-(5-phenylethynylpyridin-3-yl)-ethanone, (prepared as described in EXAMPLE 84), (230 mg, 1.05 mmol) and potassium carbonate (720 mg, 5.24 mmol) to give the title compound (115 mg, 38%).

$^1$H NMR (400 MHz, CDCl$_3$) δ 2.22 (s, 3H), 3.95 (s, 3H), 7.48-7.42 (m, 3H), 7.63-7.57 (m, 2H), 8.23 (t, J=2.2 Hz, 1H), 8.79 (d, J=1.8 Hz, 1H), 8.85 (d, J=1.8 Hz, 1H); MS (ES): m/z=251 [M+H]$^+$.

Example 86

(Z)-5-Phenylethynylpyridine-3-carbaldehyde O-methyloxime

Minor isomer isolated from the reaction mixture of EXAMPLE 7. $^1$H NMR (400 MHz, CDCl$_3$) δ 4.05 (s, 3H), 7.42-7.37 (m, 3H), 7.60-7.52 (m, 2H), 8.48 (t, J=2.0 Hz, 1H), 8.67 (d, J=1.8 Hz, 1H), 8.92 (d, J=1.8 Hz, 1H); MS (ES): m/z=237[M+H]$^+$.

Example 87

3-Bromo-5-(3-fluorophenylethynyl)-pyridine

Add 1-ethynyl-3-fluorobenzene (250 mg, 2.11 mmol) to a mixture of 3,5-dibromopyridine (500 mg, 2.11 mmol) in triethylamine (4 mL) containing bis(triphenylphosphine)palladium (II) dichloride (28 mg, 0.04 mmol) and copper (I) iodide (15 mg, 0.08 mmol) and heat at 70° C. for 2 h. Cool to room temperature, dilute with ethyl acetate and an aqueous solution of ammonium chloride and separate the resulting layers. Wash the organic layer with an aqueous saturated solution of sodium chloride, dry (magnesium sulfate), filter and concentrate. Purify by silica gel chromatography, eluting with 0.5% ethanol in 50:50 dichloromethane:hexanes to give the title compound (160 mg, 28%).

$^1$H NMR (400 MHz, CDCl$_3$) δ 7.36-7.29 (m, 1H), 7.54-7.41 (m, 3H), 8.31 (t, J=2.0 Hz, 1H), 8.75-8.72 (m, 2H); MS (ES): m/z=277 [M+H]$^+$.

Example 88

(E)-5-Phenylethynylpyridine-3-carbaldehyde O-methyloxime

Prepared in the essentially the same manner as EXAMPLE 7, but isolated as the free base.

$^1$H NMR (400 MHz, CH$_3$OH-d4) δ 8.68 (dd, 2H, J=11.0, 1.8 Hz), 8.18-8.14 (m, 2H), 7.59-7.54 (m, 2H), 7.43-7.37 (m, 3H), 3.99 (s, 3H); MS (ES): m/z=237 [M+H]$^+$.

Example 89

5-(3-Fluorophenylethynyl)-pyridine-3-carbaldehyde

Prepare essentially as described in EXAMPLE 5 using a 1 M solution of diisobutylaluminum hydride in toluene (1.2 mL, 1.20 mmol), 5-(3-fluorophenylethynyl)-N-methoxy-N-methylnicotinamide, (prepared as described in PREPARATION 18), (170 mg, 0.60 mmol) to give the title compound (86 mg, 64%).

$^1$H NMR (400 MHz, CDCl$_3$) δ 7.16-7.07 (m, 1H), 7.28-7.24 (m, 1H), 7.39-7.32 (m, 2H), 8.28 (t, J=2.0 Hz, 1H), 9.08-8.90 (m, 2H), 10.13 (s, 1H); MS (ES): m/z=226 [M+H]$^+$.

Example 90

3-(5-Formylpyridin-3-ylethynyl)-benzonitrile

Add a 2 M solution of isopropylmagnesium chloride in tetrahydrofuran (220 mg, 2.12 mmol) to a −20° C. solution of 3-(5-bromopyridin-3-ylethynyl)-benzonitrile, (prepared essentially as described in PREPARATION 19), (300 mg, 1.06 mmol) in tetrahydrofuran (2 mL) and stir for 1 h. Add N,N-dimethylformamide (150 mg, 2.12 mmol) in one portion, warm to room temperature, dilute with ethyl acetate and an aqueous saturated solution of sodium bicarbonate and separate the layers. Dry (magnesium sulfate), filter and concentrate. Purify by silica gel chromatography, eluting with 0:100 to 60:40 tetrahydrofuran:hexanes to give the title compound (92 mg, 37%).

$^1$H NMR (400 MHz, CDCl$_3$) δ 7.55-7.50, (m, 1H), 7.68 (dt, J=4.6 Hz, 2.6 Hz, 1H), 7.78 (dt, J=4.7, 2.6 Hz, 1H), 7.86-7.84 (m, 1H), 8.28 (t, J=2.2 Hz, 1H), 8.97 (d, J=2.2 Hz, 1H), 9.04 (d, J=2.2 Hz, 1H), 10.14 (s, 1H); MS (ES): m/z=233 [4+H]$^+$.

Example 91

5-(3-Methoxyphenylethynyl)-pyridine-3-carbaldehyde

Prepare essentially as described in EXAMPLE 90 using a 1 M solution of isopropylmagnesium chloride in tetrahydrofuran (2.98 mL, 2.98 mmol), 3-bromo-5-(3-methoxyphenylethynyl)-pyridine, (prepared as described in PREPARATION 20), (430 mg, 1.49 mmol) to give the title compound (290 mg, 82%).

$^1$H NMR (400 MHz, CDCl$_3$) δ 3.84 (s, 3H), 6.96 (ddd, J=8.3 Hz, 2.6 Hz, 0.9 Hz, 1H), 7.10-7.07 (m, 1H), 7.16 (dt, J=4.4 Hz, 2.3 Hz, 1H), 7.30 (t, J=8.1 Hz, 1H), 8.27 (t, J=2.0

Hz, 1H), 8.96 (d, J=1.8 Hz, 1H), 9.00 (d, J=1.8 Hz, 1H), 10.13 (s, 1H); MS (ES): m/z=238 [M+H]+.

Example 92

5-(3-Fluorophenylethynyl)-pyridine-3-carbaldehyde O-methyloxime

Heat a mixture of 5-(3-fluorophenylethynyl)-pyridine-3-carbaldehyde, (prepared essentially as described in EXAMPLE 89), (90 mg, 0.38 mmol) and methoxylamine hydrochloride (160 mg, 3.02 mmol) and potassium carbonate (260 mg, 1.89 mmol) in ethanol at 80° C. overnight. Cool to room temperature, filter solids and concentrate. Purify the residue by silica gel chromatography, eluting with 5:45:45 ethyl acetate:chloroform:hexanes, to give the title compound as a white solid (45 mg, 47%).
$^1$H NMR (400 MHz, CDCl$_3$) δ 4.02 (s, 3H), 7.13-7.05 (m, 1H), 7.26 (s, 2H), 7.38-7.30 (m, 2H), 8.06 (s, 1H), 8.10 (t, J=2.0 Hz, 1H), 8.70 (d, J=18.5 Hz, 2H); MS (ES): m/z=255 [M+H]+.

Example 93

3-[5-(Methoxyiminomethyl)-pyridin-3-ylethynyl]-benzonitrile

Prepare essentially as described in EXAMPLE 6 using methoxylamine hydrochloride (2.88 g, 34.45 mmol), potassium carbonate (2.97 g, 21.53 mmol) and 3-(5-formylpyridin-3-ylethynyl)-benzonitrile (1.00 g, 4.31 mmol), (prepared as described in EXAMPLE 90), to give the title compound (0.84 g, 75%).
$^1$H NMR (400 MHz, CDCl$_3$) δ 4.02 (s, 3H), 7.51 (t, J=7.9 Hz, 1H), 7.66 (dt, J=4.6 Hz, 2.5 Hz, 1H), 7.76 (dt, J=4.6 Hz, 2.6 Hz, 1H), 7.83 (t, J=1.3 Hz, 1H), 8.06 (s, 1H), 8.10 (t, J=2.0 Hz, 1H), 8.71 (d, J=14.1 Hz, 2H); MS (ES): m/z=263 [M+H]+.

Example 94

(E)-5-(3-Methoxyphenylethynyl)-pyridine-3-carbaldehyde O-methyloxime

Prepare essentially as described in EXAMPLE 6 using 5-(3-methoxyphenylethynyl)-pyridine-3-carbaldehyde, (prepared essentially as described in EXAMPLE 91), (290 mg, 1.22 mmol) and methoxylamine hydrochloride (520 mg, 9.78 mmol). The E/Z Isomers were separated during the purification to give the title compound (254 mg, 78%).
$^1$H NMR (400 MHz, DMSO-d$_6$) δ 3.78 (s, 3H) 3.93 (s, 3H), 7.05-7.00 (m, 1H), 7.19-7.13 (m, 2H), 7.35 (t, J=8.1 Hz, 1H), 8.17 (t, J=2.0 Hz, 1H), 8.32 (s, 1H), 8.78 (dd, J=3.1 Hz, 2.2 Hz, 2H); MS (ES): m/z=267 [M+H]+.

Example 95

(Z)-5-(3-Methoxyphenylethynyl)-pyridine-3-carbaldehyde O-methyloxime

Minor component (Z-Isomer) isolated from the reaction mixture of EXAMPLE 94.
$^1$H NMR (400 MHz, DMSO-d$_6$) δ 3.84 (s, 3H), 4.08 (s, 3H), 6.94 (ddd, J=8.3 Hz, 2.6 Hz, 0.9 Hz, 1H), 7.10-7.04 (m, 1H), 7.18-7.12 (m, 1H), 7.33-7.24 (m, 3H), 8.43 (s, 1H); MS (ES): m/z=267 [M+H]+.

Example 96

3-Bromo-5-(4-fluorophenylethynyl)-pyridine hydrochloride

Add 1 M hydrogen chloride in diethyl ether (1.1 eq) to 3-bromo-5-(4-fluorophenylethynyl)-pyridine, from PREPARATION 24, in diethyl ether and stir for 2 h. Filter and dry the collected solid under high vacuum to give the title compound.
$^1$H NMR (400 MHz, CDCl$_3$) δ 7.11-7.05 (m, 2H), 7.55-7.50 (m, 2H), 7.96 (t, J=2.0 Hz, 1H), 8.64 (d, J=14.1 Hz, 2H); MS (ES): m/z=276 [M+H]+.

Example 97

5-(4-Fluorophenylethynyl)-pyridine-3-carbaldehyde O-methyloxime hydrochloride

Prepare essentially as described in EXAMPLE 6 using 5-(4-fluorophenylethynyl)-pyridine-3-carbaldehyde, (prepared essentially as described in EXAMPLE 99), (150 mg, 0.64 mmol), methoxylamine hydrochloride (430 mg, 5.15 mmol) and potassium carbonate to give the title compound (120 mg, 64%).
$^1$H NMR (400 MHz, DMSO-d$_6$) δ 3.93 (s, 3H), 7.33-7.26 (m, 2H), 7.70-7.63 (m, 2H), 8.16 (t, J=2.2 Hz, 1H), 8.32 (s, 1H), 8.77 (dd, J=5.1 Hz, 2.0 Hz, 2H); MS (ES): m/z=255 [M+H]+.

Example 98

5-(4-Fluorophenylethynyl)-pyridine-3-carbaldehyde oxime hydrochloride

Prepare in a similar manner as described in EXAMPLE 6 using 5-(4-fluorophenylethynyl)-pyridine-3-carbaldehyde (150 mg, 0.64 mmol), (prepared essentially as described in EXAMPLE 99), hydroxylamine hydrochloride (360 mg, 5.15 mmol) and potassium carbonate (440 mg, 3.22 mmol) to give the title compound (90 mg, 50%).
$^1$H NMR (400 MHz, DMSO-d$_6$) δ 7.30 (t, J=8.8 Hz, 2H), 7.66 (dd, J=5.3 Hz, 8.8 Hz, 1H), 8.13 (s, 1H), 8.22 (s, 1H), 8.73 (d, J=1.8 Hz, 1H), 8.78 (d, J=1.3 Hz, 1H), 11.70 (s, 1H); MS (ES): m/z=241 [M+H]+.

Example 99

5-(4-Fluorophenylethynyl)-pyridine-3-carbaldehyde

Prepare in a similar manner as described in EXAMPLE 90, using a 2 M solution of isopropylmagnesium chloride in tetrahydrofuran (2.99 mL, 5.98 mmol), 3-bromo-5-(4-fluorophenylethynyl)-pyridine (1.50 g, 5.43 mmol), (prepared essentially as described in EXAMPLE 96), and anhydrous N,N-dimethylformamide (1.99 g, 27.16 mmol) to give the title compound (0.29 g, 24%).
$^1$H NMR (400 MHz, CDCl$_3$) δ 7.12-7.06 (m, 2H), 7.58-7.53 (m, 2H), 8.26 (t, J=2.0 Hz, 1H), 8.95 (d, J=2.2 Hz, 1H), 9.00 (d, J=2.2 Hz, 1H), 10.13 (s, 1H); MS (ES): m/z=226 [M+H]+.

Example 100

3-Bromo-5-(3,4-difluorouhenylethynyl)-pyridine

Prepare in a similar manner as described in PREPARATION 17 using 1 M solution of tetrabutylammonium fluoride in tetrahydrofuran (8.3 mL, 8.33 mmol), 3,4-difluoroiodobenzene, (prepared essentially as described in PREPARATION 22), (2.00 g, 8.33 mmol), 3-bromo-5-[(trimethylsilanyl)-ethynyl]-pyridine (2.12 g, 8.33 mmol), bis(triphenylphosphine)palladium (II) dichloride (120 mg, 0.17 mmol) and copper (I) iodide (63 mg, 0.33 mmol) to give the title compound (1.9 g, 78%).

$^1$H NMR (400 MHz, CDCl$_3$) δ 7.59-7.45 (m, 2H), 7.74 (ddd, J=11.2 Hz, 7.7 Hz, 2.0 Hz, 1H), 8.30 (t, J=2.0 Hz, 1H), 8.74 (t, J=2.2 Hz, 2H); MS (ES): m/z=295 [M+H]$^+$.

Example 101

5-(3,4-Difluorophenylethynyl)-pyridine-3-carbaldehyde

Add a 2.5 M solution of butyllithium in hexanes (3.18 mL, 7.96 mmol) to anhydrous toluene (11 mL) at −78° C. Allow the internal temperature to return to −78° C., then add 3-bromo-5-(3,4-difluorophenylethynyl)-pyridine (1.56 g, 5.30 mmol), (prepared essentially as described in EXAMPLE 100), dissolved in anhydrous toluene (11 mL) at such a rate to maintain the reaction temperature below −60° C. Stir for 5 min, add N,N-dimethylformamide (0.47 g, 6.37 mmol) dropwise at a rate so as to maintain the reaction temperature below −60° C. Stir for 20 min, warm to 0° C. and add an aqueous saturated solution of ammonium chloride and ethyl acetate. Stir for 5 min and separate the layers. Dry (magnesium sulfate), filter and concentrate. Purify the residue by silica gel chromatography, eluting with 30:70 ethyl acetate:hexanes to give the title compound as a white solid (0.780 g, 61%).

$^1$H NMR (400 MHz, CDCl$_3$) δ 7.19 (dt, J=9.2 Hz, 7.8 Hz, 1H), 7.34-7.29 (m, 1H), 7.38 (ddd, J=10.5 Hz, 7.5 Hz, 1.8 Hz, 1H), 8.26 (t, J=2.2 Hz, 1H), 8.95 (d, J=2.2 Hz, 1H), 9.02 (d, J=2.2 Hz, 1H), 10.13 (s, 1H); MS (ES): m/z=244 [M+H]$^+$.

Example 102

5-(3,4-difluorophenylethynyl)-pyridine-3-carbaldehyde O-methyloxime hydrochloride Prepare in a similar manner as described in EXAMPLE 6 using 5-(3,4-difluorophenylethynyl)-pyridine-3-carbaldehyde, (prepared essentially as described in EXAMPLE 101), (0.28 g, 1.15 mmol), methoxylamine hydrochloride (0.77 g, 9.21 mmol) and potassium carbonate (0.80 g, 5.76 mmol) to give the title compound (0.28 g, 80%).

$^1$H NMR (400 MHz, DMSO-d$_6$) δ 3.93 (s, 3H), 7.58-7.45 (m, 2H), 7.76 (ddd, J=11.2 Hz, 7.9 Hz, 2.0 Hz, 1H), 8.17 (t, J=2.0 Hz, 1H), 8.32 (s, 1H), 8.78 (dd, J=8.6 Hz, 2.0 Hz, 2H); MS (ES): m/z=273 [M+H]$^+$.

Example 103

5-(3,4-Difluorophenylethynyl)-pyridine-3-carbaldehyde oxime hydrochloride

Prepare in a similar manner as described in EXAMPLE 6 using 5-(3,4-difluorophenylethynyl)-pyridine-3-carbaldehyde (0.28 g, 1.15 mmol), (prepared essentially as described in EXAMPLE 101), hydroxylamine hydrochloride (0.64 g, 9.21 mmol) and potassium carbonate (0.80 g, 5.76 mmol) to give the title compound (0.120 g, 35%).

$^1$H NMR (400 MHz, DMSO-d$_6$) δ 7.58-7.45 (m, 2H), 7.76 (ddd, J=11.2 Hz, 7.7 Hz, 2.0 Hz, 1H), 8.18 (t, J=2.0 Hz, 1H), 8.22 (s, 1H), 8.76 (d, J=2.2 Hz, 1H), 8.80 (d, J=1.8 Hz, 1H). MS (ES): m/z=259 [M+H]$^+$.

Example 104

3-(4-Fluorophenylethynyl)-5-methoxypyridine

Dissolve 3-bromo-5-methoxypyridine (1.0 g, 5.35 mmol) in diisopropylamine (17 mL) and toluene (10 mL) under nitrogen. Add tetrakis(triphenylphosphine)palladium (0.200 g, 0.16 mmol). Heat at 60° C. and add 1-ethynyl-4-fluorobenzene (642 mg, 5.35 mmol) and copper (I) iodide (20 mg, 0.11 mmol). After 20 h, concentrate, and purify using silica gel chromatography, eluting with 30:70 ethyl acetate:hexanes, to give the title compound (720 mg, 60%).

$^1$H NMR (300 MHz, CDCl$_3$) δ 3.88 (s, 3H), 7.03-7.11 (m, 2H), 7.29-7.30 (m, 1H), 7.52-7.56 (m, 2H), 8.27 (d, J=2.9 Hz, 1H), 8.36 (d, J=1.6 Hz, 1H); MS (APCI): m/z=228 [M+H]$^+$.

Example 105

3-(4-Fluoro-3-methylphenylethynyl)-5-methoxypyridine

Dissolve 3-bromo-5-methoxypyridine (1.0 g, 5.35 mmol) in diisopropylamine (17 mL) and toluene (10 mL) under nitrogen. Add tetrakis(triphenylphosphine)palladium (0.200 g, 0.16 mmol). Heat at 60° C. and add 4-ethynyl-1-fluoro-2-methylbenzene (717 mg, 5.35 mmol) and copper (I) iodide (20 mg, 0.11 mmol). After 20 h add additional 4-ethynyl-1-fluoro-2-methylbenzene (100 mg, 0.75 mmol) and heat at 60° C. for 5 h. Concentrate and purify using silica gel chromatography, eluting with 30:70 to 40:60 ethyl acetate:hexanes, to give the title compound (660 mg, 51%).

$^1$H NMR (300 MHz, CDCl$_3$) δ 2.28 (s, 3H), 3.88 (s, 3H), 6.97-7.03 (m, 1H), 7.28-7.29 (m, 1H), 7.33-7.41 (m, 2H), 8.26 (d, J=2.8 Hz, 1H), 8.35 (d, J=1.6 Hz, 1H); MS (APCI): m/z=242 [M+H]$^+$.

Example 106

3-(4-Fluoro-3-trifluoromethylphenylethynyl)-5-methoxypyridine

Dissolve 1-fluoro-4-iodo-2-trifluoromethylbenzene (813 mg, 2.8 mmol) in triethylamine (6 mL). Add 3-ethynyl-5-methoxypyridine, (prepared as described in PREPARATION 10), (400 mg, 3.0 mmol) followed by bis(triphenylphosphine)palladium (II) dichloride (0.100 g, 0.14 mmol) and copper (I) iodide (53 mg, 0.28 mmol). Heat at 70° C. for 16 h, concentrate, and purify using silica gel chromatography, eluting with 100:0 to 90:10 methylene chloride:ethyl acetate, to give the title compound as a pale yellow solid (820 mg, 99%).

$^1$H NMR (300 MHz, CDCl$_3$) δ 3.89 (s, 3H), 7.19-7.26 (m, 1H), 7.30-7.31 (m, 1H), 7.69-7.74 (m, 1H), 7.79-7.82 (m, 1H), 8.30 (d, J=2.8 Hz, 1H), 8.38 (d, J=1.3 Hz, 1H); MS (APCI): m/z=296 [M+H]$^+$.

Example 107

3-(5-Aminopyridin-3-ylethynyl)-benzonitrile

Add trifluoroacetic acid (1 mL, 13.3 mmol) to a solution of [5-(3-cyanophenylethynyl)-pyridin-3-yl]-carbamic acid tert-butyl ester, prepared as described in EXAMPLE 125), (315 mg, 0.99 mmol) in dichloromethane (5 mL) and stir for 4 h. Add solid potassium carbonate to the reaction mixture until basic (pH=8) and then water to give a biphasic solution. Separate the layers, load the aqueous layer onto an ISOLUTE™ phase separator cartridge and wash the cartridge with dichloromethane (3×15 mL). Concentrate and purify the residue by silica gel chromatography, eluting with 25:75 to 0:100 with dichloromethane:ethyl acetate, to give the title compound (190 mg, 88%).

$^1$H NMR (300 MHz, CDCl$_3$) δ 3.79 (s, 2H), 7.10 (dd, J=2.8, 1.6 Hz, 1H), 7.48 (t, J=7.9 Hz, 1H), 7.63 (dt, J=7.9, 1.4 Hz, 1H), 7.73 (dt, J=7.9, 1.4 Hz, 1H), 7.80 (m, 7.79-7.80, 1H), 8.07 (d, J=2.8 Hz, 1H), 8,17 (d, J=1.4 Hz, 1H); MS (ES): m/z=220 [M+H]$^+$.

Example 108

3-Chloro-5-(3,4-difluorophenylethynyl)-pyridine

Add bis(triphenylphosphine)palladium (II) dichloride (49 mg, 0.07 mmol), copper (I) iodide (28 mg, 0.15 mmol), and 3-chloro-5-ethynylpyridine, (prepared as described in PREPARATION 27), (200 mg, 1.5 mmol) to a solution of 1,2-difluoro-4-iodobenzene (420 mg, 1.7 mmol) in triethylamine (3.1 mL, 22 mmol) and heat at 60° C. for 16 h. Cool to room temperature and concentrate. Purify the residue by silica gel chromatography, eluting with a gradient of 50:50 to 100:0 dichloromethane:hexanes, followed by a second silica gel chromatography, eluting with 95:5 to 85:15 hexanes:ethyl acetate to give the title compound as a white solid (320 mg, 88%).

$^1$H NMR (300 MHz, CDCl$_3$) δ 7.14-7.23 (m, 1H), 7.28-7.40 (m, 2H), 7.76-7.82 (t, J=2.0 Hz, 1H), 8.51-8.55 (d, J=2.3 Hz, 1H), 8.59-8.62 (d, J=1.8 Hz, 1H); MS (APCI): m/z=250 [M+H]$^+$.

Example 109

3-Chloro-5-(4-fluoro-3-methylphenylethynyl)-pyridine

Add 4-ethynyl-1-fluoro-2-methylbenzene (0.56 g, 4.21 mmol), triethylamine (2.2 mL, 15 mmol), copper (I) iodide (36 mg, 0.19 mmol), and bis(triphenylphosphine)palladium (II) dichloride (110 mg, 0.15 mmol) to a solution of trifluoromethanesulfonic acid 5-chloropyridin-3-yl ester, (prepared as described in PREPARATION 25), (1.0 g, 3.8 mmol) in ethyl acetate (5 mL) under nitrogen. Heat the at 70° C. for 16 h and concentrate. Purify by silica gel chromatography, eluting with 100% dichloromethane, followed by a second silica gel chromatography eluting with 50:50 to 60:40 dichloromethane:hexanes, to give the title compound as a light yellow solid (410 mg, 44%).

$^1$H NMR (300 MHz, CDCl$_3$) δ 2.29 (s, 3H), 6.96-7.04 (t, J=9.1 Hz, 1H), 7.30-7.41 (m, 2H), 7.76-7.79 (t, J=2.1 Hz, 1H), 8.49-8.52 (d, J=2.3 Hz, 1H), 8.59-8.61 (d, J=1.8 Hz, 1H); MS (APCI): mm/z=246 [M+H]$^+$.

Example 110

2-Fluoro-5-(5-methoxypyridin-3-ylethynyl)-benzonitrile

Add bis(triphenylphosphine)palladium (II) dichloride (77 mg, 0.1 mmol), copper (I) iodide (44 mg, 0.23 mmol), and 3-ethynyl-5-methoxypyridine (300 mg, 2.3 mmol), (prepared as described in PREPARATION 10), to a solution of 2-fluoro-5-iodobenzonitrile (670 mg, 2.7 mmol) in triethylamine (3.4 mL, 34 mmol) and heat at 60° C. for 2.75 h. Cool to room temperature and concentrate. Purify the residue by silica gel chromatography, eluting with 100:0 to 80:20 dichloromethane/ethyl acetate followed by a second silica gel chromatography, eluting with 75:25 to 60:40 hexanes:ethyl acetate to give the title compound as a white solid (510 mg, 90%).

$^1$H NMR (300 MHz, CDCl$_3$) δ 3.89 (s, 3H), 7.20-7.25 (m, 1H), 7.28-7.32 (m, 1H), 7.72-7.84 (m, 2H), 8.29-8.33 (d, J=2.9 Hz, 1H), 8.34-8.38 (d, J=1.6 Hz, 1H); MS (APCI): m/z=253 [M+H]$^+$.

Example 111

2-Fluoro-5-(5-methoxypyridin-3-ylethynyl)-phenylamine

Add tin (II) chloride dihydrate (1.41 g, 6.26 mmol) to a suspension of 3-(4-fluoro-3-nitrophenylethynyl)-5-methoxypyridine, (prepared as described in EXAMPLE 116), (190 mg, 0.69 mmol) in ethanol (20 mL) and tetrahydrofuran (17 mL) under nitrogen and heat at 70° C. for 2 h. Cool the reaction mixture, add a 50% aqueous solution of potassium hydroxide (100 mL), and extract with diethyl ether (2×100 mL). Wash the combined organic phases with an aqueous saturated solution of sodium chloride (100 mL), dry (sodium sulfate), filter, and concentrate. Purify the residue by silica gel chromatography, eluting with ethyl acetate to give the title compound as a yellow solid. Further purify the title compound by silica gel chromatography, eluting with 100% dichloromethane to 20:80 ethyl acetate:dichloromethane, to give the title compound as a white solid (143 mg, 86%).

$^1$H NMR (300 MHz, CDCl$_3$) δ 3.78 (br s, 2H), 3.87 (s, 3H), 6.80-7.06 (m, 3H), 7.26-7.30 (m, 1H), 8.25 (d, J=2.8 Hz, 1H), 8.34 (d, J=1.6 Hz, 1H); MS (APCI): m/z=243 [M+H]$^+$.

Example 112

3-Chloro-5-(4-fluoro-3-trifluoromethylphenylethynyl)-pyridine

Sequentially add 3-chloro-5-ethynylpyridine, (prepared as described in PREPARATION 27), (300 mg, 2.2 mmol), (bis(triphenylphosphine)palladium (II) dichloride (69 mg, 0.10 mmol), and copper (I) iodide (38 mg, 0.198 mmol) to a solution of 1-fluoro-4-iodo-2-trifluoromethylbenzene (575 mg, 1.98 mmol) in triethylamine (4 mL) under nitrogen. Heat at 70° C. for 2.5 h and concentrate. Purify the residue by silica gel chromatography, eluting from 0:100 to 20:80 using ethyl acetate:hexanes, to give the title compound as a white solid (520 mg, 88%).

$^1$H NMR (300 MHz, CDCl$_3$) δ 7.19-7.23 (m, 1H), 7.67-7.74 (m, 1H), 7.79-7.87 (m, 2H), 8.55 (d, J=2.3 Hz, 1H), 8.63 (d, J=1.7 Hz, 1H); MS (APCI): m/z=300 [M+H]$^+$.

Example 113

3-Chloro-5-(4-fluorophenylethynyl)-pyridine

Add 4-fluorophenylacetylene (1.0 g, 8.35 mmol), triethylamine (4 mL, 30 mmol), copper (I) iodide (76 mg, 0.40 mmol), and bis(triphenylphosphine)palladium (II) dichloride (140 mg, 0.20 mmol) to a solution of trifluoromethanesulfonic acid 5-chloropyridin-3-yl ester, (prepared as described in PREPARATION 25) in ethyl acetate (1.95 g, 7.5 mmol), (7 mL) under nitrogen and heat at 60° C. for 12 h. Concentrate and purify the residue by silica gel chromatography, eluting with dichloromethane to give the title compound as a white solid (1.12 g, 65%).

¹H NMR (300 MHz, CDCl₃) δ 7.04-7.11 (m, 2H), 7.51-7.55 (m, 2H), 7.79-7.80 (m, 1H), 8.51 (d, J=2.3 Hz, 1H), 8.61 (d, J=1.7 Hz, 1H); MS (APCI): m/z=232 [M+H]⁺.

Example 114

3-(3,4-Difluorophenylethynyl)-5-methoxypyridine

Add bis(triphenylphosphine)palladium (II) dichloride (110 mg, 0.15 mmol), copper (I) iodide (57 mg, 0.30 mmol), and 3-ethynyl-5-methoxypyridine, (prepared as described in PREPARATION 10), (400 mg, 3.0 mmol) to a solution of 1,2-difluoro-4-iodobenzene (0.43 mL, 3.6 mmol) in triethylamine (6.3 mL, 45.0 mmol) and heat at 60° C. for 20 h. Cool to room temperature and concentrate. Purify the residue by silica gel chromatography, eluting with 100:0 to 65:35 hexanes:ethyl acetate, followed by a second silica gel chromatography, eluting with 100:0 to 80:20 dichloromethane:ethyl acetate, to give the title compound as a white solid (690 mg, 94%).
¹H NMR (300 MHz, CDCl₃) δ 3.89 (s, 3H), 7.11-7.21 (m, 1H), 7.28-7.40 (m, 3H), 8.27-8.30 (d, J=2.9 Hz, 1H), 8.34-8.37 (d, J=1.6 Hz, 1H); MS (APCI): m/z=246 [M+H]⁺.

Example 115

3-(3-Chloro-4-fluorophenylethynyl)-5-methoxypyridine

Add bis(triphenylphosphine)palladium (II) dichloride (110 mg, 0.15 mmol), copper (I) iodide (57 mg, 0.30 mmol), and 3-ethynyl-5-methoxypyridine, (prepared as described in PREPARATION 10), (400 mg, 3.0 mmol) to a solution of 2-chloro-1-fluoro-4-iodobenzene (0.46 mL, 3.6 mmol) in triethylamine (6.3 mL, 45.0 mmol) and heat at 60° C. for 5 h. Cool to room temperature and concentrate. Purify the residue by silica gel chromatography, eluting with a gradient of 100:0 to 80:20 dichloromethane:ethyl acetate, followed by a second silica gel chromatography, eluting with 67:33 to 60:40 hexanes:ethyl acetate, to give the title compound as a white solid (730 mg, 93%).
¹H NMR (300 MHz, CDCl₃) δ 3.88 (s, 3H), 7.11-7.18 (t, J=8.7 Hz, 1H), 7.28-7.32 (m, 1H), 7.39-7.46 (m, 1H), 7.57-7.63 (m, 1H), 8.27-8.30 (d, J=2.8 Hz, 1H), 8.34-8.37 (d, J=1.5 Hz, 1H); MS (APCI): m/z=262 [M+H]⁺.

Example 116

3-(4-Fluoro-3-nitrophenylethynyl)-5-methoxypyridine

Sequentially add 3-ethynyl-5-methoxypyridine, (prepared as described in PREPARATION 10), (400 mg, 3.0 mmol), bis(triphenylphosphine)palladium (II) dichloride (0.100 g, 0.14 mmol) and copper (I) iodide (53 mg, 0.28 mmol) to a solution of 4-bromo-1-fluoro-2-nitrobenzene (616 mg, 2.8 mmol) in triethyl amine (6 mL) and heat for 2 h at 60° C. Add additional 3-ethynyl-5-methoxypyridine (100 mg, 0.75 mmol) and continue heating for 1 h. Concentrate and purify the residue by silica gel chromatography, eluting with 30:70 to 40:60 ethyl acetate:hexanes, to give the title compound as a pale yellow solid (330 mg, 43%).
¹H NMR (300 MHz, CDCl₃) δ 3.90 (s, 3H), 7.28-7.35 (m, 2H), 7.56-7.81 (m, 1H), 8.24 (dd, J=7.0 Hz, 2.1 Hz, 1H), 8.32 (br s, 1H), 8.39 (br s, 1H); MS (APCI): m/z=273 [M+H]⁺.

Example 117

5-(5-Cyanopyridin-3-ylethynyl)-2-fluorobenzamide

Add N-(3-dimethylaminopropyl)-N-ethylcarbodiamide hydrochloride (128 mg, 0.66 mmol) to a solution of 5-(5-cyanopyridin-3-ylethynyl)-2-fluorobenzoic acid (prepared as described in EXAMPLE 120), (158 mg, 0.59 mmol) and 1-hydroxybenzotriazole hydrate (87 mg, 0.64 mmol) in N,N-dimethylformamide (5 mL) and stir for 5 min to form a gel. Add additional N,N-dimethylformamide (4 mL) to enable stirring of the reaction mixture and stir for 0.5 h. Bubble anhydrous ammonia gas through the reaction mixture for 1-2 min. and then stir for an additional 15 min. Dilute the reaction mixture with ethyl acetate and a saturated aqueous solution of sodium bicarbonate and separate the layers. Extract the aqueous phase once with ethyl acetate. Wash the combined organic phases once with an aqueous saturated solution of sodium chloride, dry (sodium sulfate), filter and concentrate. Purify the residue by silica gel chromatography, eluting with 20:80 ethyl acetate:dichloromethane, to give the title compound as a white solid (66 mg, 42%).
¹H NMR (400 MHz, DMSO-d₆) δ 7.37-7.42 (m, 1H), 7.70-7.87 (m, 4H), 8.56 (t, J=2.2 Hz, 1H), 9.02 (d, J=1.8 Hz, 2H); MS (ES): m/z=266.0 [M+H]⁺.

Example 118

5-(5-Cyanopyridin-3-ylethynyl)-2-fluoro-N-methylbenzamide

Add N-(3-dimethylaminopropyl)-N-ethylcarbdiimide hydrochloride (120 mg, 0.62 mmol) to a mixture of methylamine (19 mg, 310 µL of a 2.0 M stock solution in tetrahydrofuran, 0.62 mmol), 5-(5-cyanopyridin-3-ylethynyl)-2-fluorobenzoic acid), (prepared as described in EXAMPLE 120), (150 mg, 0.56 mmol) and 1-hydroxybenzotriazole hydrate (76 mg, 0.56 mmol) in N,N-dimethylformamide (2 mL), and stir for 2 h. Dilute the reaction mixture with ethyl acetate and an aqueous saturated solution of sodium bicarbonate and separate the layers. Extract the aqueous phase once with ethyl acetate. Wash the combined organic phases once with an aqueous saturated solution of sodium chloride, dry (sodium sulfate), filter and concentrate. Purify the residue by silica gel chromatography, eluting with 20:80 ethyl acetate:dichloromethane, to give the title compound as a white solid (107 mg, 68%).
¹H NMR (400 MHz, CDCl₃) δ 3.05 (dd, J=1.3 Hz, J=4.6 Hz, 3H), 6.73 (br s, 1H), 7.13-7.18 (m, 1H), 7.60-7.65 (m, 1H), 8.05-8.06 (m, 1H), 8.31 (dd, J=2.2 Hz, J=7.5 Hz, 1H), 8.81 (d, J=1.8 Hz, 1H), 8.91 (d, J=2.2 Hz, 1H); MS (ES): m/z=280.0 [M+H]⁺.

Example 119

5-(5-Cyanopyridin-3-ylethynyl)-2-fluoro-N,N-dimethylbenzamide

Add N-(3-dimethylaminopropyl)-N-ethylcarbodiamide hydrochloride (120 mg, 0.62 mmol) to a mixture of dimethylamine hydrochloride (51 mg, 0.62 mmol), N,N-diisopropylethylamine (108 µL, 0.62 mmol), 5-(5-cyanopyridin-3-ylethynyl)-2-fluorobenzoic acid, (prepared as described in EXAMPLE 120), (150 mg, 0.56 mmol) and 1-hydroxybenzotriazole hydrate (76 mg, 0.56 mmol) in N,N-dimethylformamide (2 mL), and stir for 2 h. Dilute the reaction mixture with ethyl acetate and an aqueous saturated solution of sodium bicarbonate and separate the layers. Extract the aqueous phase once with ethyl acetate. Extract the combined organic phases once with an aqueous saturated solution of sodium chloride, dry (sodium sulfate), filter and concentrate. Purify the residue by silica gel chromatography, eluting with 30:70 to 50:50 with ethyl acetate:hexanes, to give the title compound as a white solid (104 mg, 63%).

$^1$H NMR (300 MHz, CDCl$_3$) δ 2.96 (s, 3H), 3.14 (s, 3H), 7.13 (t, J=8.8 Hz, 1H), 7.55-7.61 (m, 2H), 8.03-8.04 (m, 1H), 8.81 (d, J=2.2 Hz, 1H), 8.89 (d, J=2.2 Hz, 1H); MS (ES): m/z=294.0 [M+H]$^+$.

Example 120

5-(5-Cyanopyridin-3-ylethynyl)-2-fluorobenzoic acid

Add lithium hydroxide to a solution of 5-(5-cyanopyridin-3-ylethynyl)-2-fluorobenzoic acid methyl ester, (prepared as described in EXAMPLE 121), (890 mg, 3.18 mmol) in 3:1 tetrahydrofuran:water (50 mL) and stir for 1 h. Dilute the reaction mixture with diethyl ether and water and separate the layers. Adjust the pH of the aqueous layer to approximately pH=2 by dropwise addition of concentrated hydrochloric acid and then extract it three times with diethyl ether and three times with ethyl acetate. Extract the combined organic layers with an aqueous saturated solution of sodium chloride, dry (sodium sulfate), filter and concentrate. Recrystallize the resulting residue using ethyl acetate and methanol, to give the title compound as a white solid (658 mg, 78%).

$^1$H NMR (400 MHz, DMSO-d$_6$) δ 7.41-7.46 (m, 1H), 7.83-7.87 (m, 1H), 8.05-8.08 (m, 1H), 8.58-8.59 (m, 1H), 9.02-9.04 (m, 2H), 13.6 (br s, 1H); MS (ES): m/z=267.0 [M+H]$^+$.

Example 121

5-(5-Cyanopyridin-3-ylethynyl)-2-fluorobenzoic acid methyl ester

Sequentially add tri-tert-butylphosphine (88 mg, 0.437 mmol) in anhydrous 1,4-dioxane (1 mL), diisopropylethylamine (1.5 mL, 8.74 mmol), 5-bromo-2-fluorobenzoic acid methyl ester, (prepared as described in PREPARATION 42), (1.69 g, 7.28 mmol) and a solution of 5-ethynylnicotinonitrile, (prepared as described in PREPARATION 4), (0.93 g, 7.28 mmol) in anhydrous 1,4-dioxane (4 mL), to a stirring mixture of dichloro(benzonitrile)palladium (II) (84 mg, 0.218 mmol) and copper (I) iodide (28 mg, 0.146 mmol) in anhydrous 1,4-dioxane (1 mL) under nitrogen. Stir for 2 h and concentrate. Purify the residue twice by silica gel chromatography, eluting with 10:90 ethyl acetate:hexanes, to give the title compound as a white solid (0.9 g, 44%).

$^1$H NMR (400 MHz, CDCl$_3$) δ 1.48 (s, 3H), 3.87 (s, 3H), 7.07-7.12 (m, 1H), 7.58-7.62 (m, 1H), 7.96-7.98 (m, 1H), 8.06 (dd, J=2.7 Hz, J=6.5 Hz, 1H), 8.74 (br s, 1H), 8.84 (br s, 1H); MS (ES): m/z=280.9 [M+H]$^+$.

Example 122

[5-(3-Trifluoromethylphenylethynyl)-pyridin-3-yl]-carbamic acid ethyl ester

Prepare essentially as described in EXAMPLE 158 using 5-(3-trifluoromethylphenylethynyl)-pyridin-3-ylamine hydrochloride (184 mg, 0.55 mmol), (prepared essentially as described in EXAMPLE 155), to give the title compound (84.9 mg, 46%).

$^1$H NMR (300 MHz, CDCl$_3$) δ 1.34 (t, J=7.3 Hz, 3H), 4.27 (q, J=7.3 Hz, 2H), 6.73 (br s, 1H), 7.50 (t, J=7.3 Hz, 1H), 7.62 (d, J=7.3 Hz, 1H), 7.71 (d, J=7.3 Hz, 1H), 8.19 (br s, 1H), 8.45 (dd, J=11 Hz, 2.2 Hz, 2H); MS (ES): m/z=335 [M+H]$^+$.

Example 123

[5-(3-Cyanophenylethynyl)-pyridin-3-yl]-carbamic acid ethyl ester

Prepare essentially as described in EXAMPLE 158 using 3-(5-aminopyridin-3-ylethynyl)-benzonitrile (169 mg, 0.77 mmol), (prepared as described in EXAMPLE 107), to give the title compound (28.9 mg, 13%).

$^1$H NMR (300 MHz, DMSO-d6) δ 1.26 (t, J=7.3 Hz, 3H), 4.16 (q, J=7.3 Hz, 2H), 7.66 (t, J=8.1 Hz, 1H), 7.92 (m, 2H), 8.10 (m, 1H), 8.13 (m, 1H), 8.41 (br d, J=1.4 Hz, 1H), 8.41 (br d, J=2.2 Hz, 1H), 10.08 (br s, 1H, NH); MS (ES): m/z=292 [M+H]$^+$.

Example 124

3-(5-Trifluoromethylpyridin-3-ylethynyl)-benzonitrile

Prepare essentially as described in EXAMPLE 43 using 3-chloro-5-trifluoromethylpyridine (365 mg, 2.02 mmol), (prepared as described in PREPARATION 7), to give the title compound (12.7 mg, 2%).

$^1$H NMR (300 MHz, CH$_3$OH-d4) δ 7.62 (t, J=8.0 Hz, 1H), 7.79 (dt, J=8.0 Hz, 1.5 Hz, 1H), 7.89 (dt, J=8.0 Hz, 1.5 Hz, 1H), 7.99 (t, J=1.5 Hz, 1H), 8.34 (br s, 1H), 8.88 (br d, J=1.5 Hz, 1H), 8.98 (br d, J=1.5 Hz, 1H); MS (ES): m/z=273 [M+H]$^+$.

Example 125

[5-(3-Cyanophenylethynyl)-pyridin-3-yl]-carbamic acid tert-butyl ester

Prepare essentially as described in EXAMPLE 154 using 3-(5-bromopyridin-3-ylethynyl)-benzonitrile (510 mg, 1.80 mmol), (prepared as described in EXAMPLE 55), to give the title compound (15 mg, 3%).

$^1$H NMR (300 MHz, DMSO-d$_6$) δ 1.49 (s, 9H), 7.66 (t, J=8.1 Hz, 1H), 7.92 (m, 2H), 8.14 (br s, 2H), 8.38 (br d, J=2.2 Hz, 1H), 8.60 (br d, J=2.2 Hz, 1H), 9.83 (br s, 1H, NH); MS (ES): m/z=320 [M+H]$^+$.

Example 126

[5-(3-Trifluoromethylphenylethynyl)-pyridin-3-yl]-carbamic acid methyl ester

Prepare essentially as described in EXAMPLE 158 using 5-(3-trifluoromethylphenylethynyl)-pyridin-3-ylamine hydrochloride, (prepared as described in EXAMPLE 155), (151 mg, 0.45 mmol) and methyl chloroformate (0.03 mL, 0.45 mmol) to give the title compound (70 mg, 49%).

$^1$H NMR (300 MHz, CH$_3$OH-d4) δ 3.79 (s, 3H), 7.62 (t, J=8.0 Hz, 1H), 7.72 (d, J=8.0 Hz, 1H), 7.82 (d, J=8.0 Hz, 1H), 7.86 (br s, 1H), 8.18 (m, 1H), 8.37 (d, J=2.2 Hz, 1H), 8.57 (d, J=2.2 Hz, 1H); MS (ES): m/z=320 [M+H]$^+$.

Example 127

5-(3-Trifluoromethoxyphenylethynyl)-nicotinonitrile

Add triethylamine (1.73 mL, 12.28 mmol), copper (I) iodide (34.0 mg, 0.180 mmol) and bis(triphenylphosphine)

palladium (II) dichloride (107.7 mg, 0.150 mmol) to a solution of 5-bromonicotinonitrile (562.2 mg, 3.07 mmol) and 1-ethynyl -3-trifluoromethoxybenzene, (prepared as described in PREPARATION 28), (571.4 mg, 3.07 mmol) in ethyl acetate (3 mL). Stir in a sealed tube at 50° C. for 18 h, concentrate and purify the residue by silica gel chromatography, eluting with 100:0 to 100:50 hexanes:ethyl acetate, to give the title compound (130 mg, 15%).
$^1$H NMR (300 MHz, CH$_3$OH-d4) δ 7.38 (br d, J=8.1 Hz, 1H), 7.56-7.51 (m, 2H), 7.60 (br d, J=8.1 Hz, 1H), 8.38 (t, J=2.0 Hz, 1H), 8.89 (d, J=2.0 Hz, 1H), 8.96 (d, J=2.0 Hz, 1H); MS (ES): m/z=289 [M+H]$^+$.

Example 128

3-Methylsulfanyl-5-phenylethynylpyridine

Add a 2 M solution of isopropylmagnesium chloride in tetrahydrofuran (0.96 mL, 1.94 mmol) to a solution of 3-bromo-5-phenylethynylpyridine, (prepared as described in EXAMPLE 9), (500 mg, 1.94 mmol) in anhydrous tetrahydrofuran (2 mL) and stir under nitrogen at room temperature for 2 h. Add triethylamine (0.27 mL, 1.94 mmol) and dimethyl sulfide (0.175 mL, 1.94 mmol). Stir for an additional 2 h, dilute with water, extract with dichloromethane, dry (magnesium sulfate), filter and concentrate. Purify the residue by silica gel chromatography, eluting from 100:0 to 100:50 with hexanes:ethyl acetate, to give the title compound (10.1 mg, 2.3%).
$^1$H NMR (300 MHz, CH$_3$OH-d4) δ 2.56 (br s, 3H), 7.40 (m, 3H), 7.56 (m, 2H), 7.83 (br s, 1H), 8.38 (m, 1H), 8.42 (m, 1H); MS (ES): m/z=226 [M+H]$^+$.

Example 129

3-Methanesulfinyl-5-phenylethynylpyridine

Add 3-chlorobenzenecarboperoxoic acid (27.61 mg, 0.16 mmol) to a cooled solution of 3-methylsulfanyl-5-phenylethynyl-pyridine, (prepared as described in EXAMPLE 128), (35.3 mg, 0.16 mmol) in dichloromethane (1 mL) at room temperature. Stir for 2 h and then quench with a 5% aqueous solution of sodium thiosulfite. Dilute with dichloromethane and separate the layers. Sequentially extract the organic layer with a 5% aqueous solution of sodium thiosulfite and an aqueous saturated solution of sodium chloride, dry (magnesium sulfate), filter and concentrate. Purify the residue by silica gel chromatography, eluting from 100:0 to 100:50 with hexanes:ethyl acetate, to give the title compound (10.3 mg, 27%).
$^1$H NMR (300 MHz, CDCl$_3$) δ 2.80 (s, 3H), 7.35 (m, 3H), 7.50 (m, 2H), 8.16 (br s, 1H), 8.70 (m, 1H), 8.82 (m, 1H); MS (ES): m/z=242 [M+H]$^+$.

Example 130

3-Methanesulfonyl-5-phenylethynylpyridine

Add 3-chlorobenzenecarboperoxoic acid (79.2 mg, 0.46 mmol) to a solution of 3-methylsulfanyl-5-phenylethynyl-pyridine, (prepared as described in EXAMPLE 128), (34.4 mg, 0.15 mmol) in dichloromethane (1 mL) at 0° C., warm to room temperature and stir for 2 h. Dilute with a 5% aqueous solution of sodium thiosulfite and dichloromethane. After separating the layers, sequentially wash the organic layer with a 5% aqueous solution of sodium thiosulfite and an aqueous saturated solution of sodium chloride, dry (magnesium sulfate), filter and concentrate. Purify the residue by silica gel chromatography, eluting with 100:0 to 100:50 hexanes:ethyl acetate, to give the title compound (24.8 mg, 64%).
$^1$H NMR (300 MHz, CDCl$_3$) δ 3.10 (s, 3H), 7.37 (m, 3H), 7.51 (m, 2H), 8.29 (br s, 1H), 8.93 (br s, 1H), 9.01 (br s, 1H); MS (ES): m/z=258 [M+H]$^+$.

Example 131

3-(3-Chlorophenylethynyl)-5-methylsulfanylpyridine hydrochloride

Prepare essentially as described in EXAMPLE 128 using 3-bromo-5-(3-chlorophenylethynyl)-pyridine, (prepared as described in EXAMPLE 44), (475 mg, 1.63 mmol) to give the free base of the title compound which is treated with 2 M hydrogen chloride in diethyl ether to give the title compound (91 mg, 19%).
$^1$H NMR (300 MHz, CH$_3$OH-d4) δ 2.76 (s, 3H), 7.52 (m, 1H), 7.56 (m, 1H), 7.64 (br d, J=7.7 Hz, 1H), 7.74 (br s, 1H), 8.49 (br d, J=8.07 Hz, 1H), 8.72 (br s, 1H), 8.79 (br s, 1H); MS (ES): m/z=260 [M+H]$^+$.

Example 132

3-Methylsulfanyl-5-m-tolylethynylpyridine

Prepare essentially as described in EXAMPLE 128 using 3-bromo-5-m -tolylethynylpyridine, (prepared as described in EXAMPLE 45), (550 mg, 2.0 mmol) to give the title compound (300 mg, 63%).
$^1$H NMR (300 MHz, CH$_3$OH-d4) δ 2.36 (s, 3H), 2.56 (s, 3H), 7.23 (br d, J=7.7 Hz, 1H), 7.28 (t, J=7.7 Hz, 1H), 7.35 (br d, J=7.7 Hz, 1H), 7.39 (br s, 1H), 7.81 (t, J=2.0 Hz, 1H), 8.37 (d, J=2.0 Hz, 1H), 8.41 (d, J=2.0 Hz, 1H); MS (ES): m/z=240 [M+H]$^+$.

Example 133

3-(3-Methoxyphenylethynyl)-5-methylsulfanyl-pyridine hydrochloride

Prepare essentially as described in EXAMPLE 128 using 3-bromo-5-(3-methoxyphenylethynyl)-pyridine, (prepared as described in PREPARATION 20), (660 mg, 2.30 mmol) to give the free base of the title compound which is treated with a 2 M solution of hydrogen chloride in diethyl ether to give the title compound (55 mg, 8%).
$^1$H NMR (300 MHz, CH$_3$OH-d4) δ 2.70 (s, 3H), 3.83 (s, 3H), 7.04 (d, J=8.5 Hz, 1H), 7.17 (br s, 1H), 7.19 (d, J=8.0 Hz, 1H), 7.35 (t, J=8.0 Hz, 1H), 8.50 (d, J=6.5 Hz, 1H), 8.66 (br s, 1H), 8.74 (br s, 1H); MS (ES): m/z=256 [M+H]$^+$.

Example 134

3-(5-Methylsulfanylpyridin-3-ylethynyl)-benzonitrile

Add copper (I) iodide (20.0 mg, 0.18 mmol), bis(triphenylphosphine)palladium (II) dichloride (64.2 m g, 0.092 mmol) and triethylamine (1.03 mL, 7.32 mmol), to a solution of 3-bromo-5-methylsulfanylpyridine, (prepared as described in PREPARATION 29), (375 mg, 1.83 mmol) and 3-ethynylbenzonitrile, (prepared as described in PREPARATION 8), (465 mg, 3.66 mmol) in ethyl acetate (3 mL) and stir at 90° C. overnight. Cool to room temperature, concentrate and purify the residue by silica gel chromatography, eluting with hexanes/ethyl acetate, to give the title compound (187 mg, 41%).

$^1$H NMR (300 MHz, CH$_3$OH-d4) δ 2.57 (s, 3H), 7.61 (t, J=8.0 Hz, 1H), 7.77 (dt, J=8.0 Hz, 1.5 Hz, 1H), 7.86 (m, 1H), 7.88 (br s, 1H), 7.95 (br s, 1H), 8.42 (d, J=2.2 Hz, 1H), 8.46 (d, J=2.2 Hz, 1H); MS (ES): m/z=251 [M+H]$^+$.

Example 135

3-(3-Bromo-4-fluorophenylethynyl)-5-chloropyridine

Add bis(triphenylphosphine)palladium (II) dichloride (77 mg, 0.11 mmol), copper (I) iodide (42 mg, 0.22 mmol), and 3-chloro-5-ethynylpyridine, (prepared as described in PREPARATION 27), (300 mg, 2.2 mmol) to a solution of 2-bromo-1-fluoro-4-iodobenzene, (prepared as described in PREPARATION 43), (0.78 g, 2.6 mmol) in triethylamine (3.3 mL, 33 mmol). Stir at room temperature for 24 h then concentrate. Purify by silica gel chromatography, eluting with 75:25 dichloromethane:hexanes to 100:0 dichloromethane:hexanes to 95:5 dichloromethane:ethyl acetate, followed by a second silica gel chromatography, eluting with 95:5 to 90:10 hexanes:ethyl acetate, to give the title compound as a white solid (560 mg, 82%).

$^1$H NMR (300 MHz, CDCl$_3$) δ 7.09-7.17 (t, J=8.4 Hz, 1H), 7.42-7.51 (m, 1H), 7.73-7.82 (m, 2H), 8.52-8.56 (d, J=2.3 Hz, 1H), 8.59-8.63 (d, J=1.7 Hz, 1H); MS (APCI): m/z=310 [M+H]$^+$.

Example 136

5-(5-Chloropyridin-3-ylethynyl)-2-fluorobenzamide

Add bis(triphenylphosphine)palladium (II) dichloride (51 mg, 0.07 mmol), copper (I) iodide (28 mg, 0.15 mmol), and 3-chloro-5-ethynylpyridine, (prepared as described in PREPARATION 27), (250 mg, 1.82 mmol) to a solution of 2-fluoro-5-iodobenzamide, (prepared as described in PREPARATION 44), (0.482 g, 1.82 mmol) in triethylamine (7 mL, 53 mmol) and heat at 70° C. After 10 minutes, add toluene (10 mL) to the solidified reaction mixture, heat at 70° C. for 1 h, cool to room temperature and stir overnight. Concentrate and purify the residue by silica gel chromatography, eluting with 50:50 to 100:0 ethyl acetate:hexanes, to give the title compound as a white solid (260 mg, 32%).

$^1$H NMR (300 MHz, CDCl$_3$) δ 5.82 (br s, 1H), 6.64 (br s, 1H), 7.15-7.21 (m, 1H), 7.60-7.69 (m, 1H), 7.79-7.81 (m, 1H), 8.32-8.35 (m, 1H), 8.53 (d, J=2.3 Hz, 1H), 8.62 (d, J=1.7 Hz, 1H); MS (APCI): m/z=275 [M+H]$^+$.

Example 137

5-(5-Chloropyridin-3-ylethynyl)-2-fluoro-N-methylbenzamide

Add bis(triphenylphosphine)palladium (II) dichloride (45 mg, 0.06 mmol), copper (I) iodide (26 mg, 0.14 mmol), and 3-chloro-5-ethynylpyridine, (prepared as described in PREPARATION 27), (200 mg, 1.45 mmol) to a solution of 2-fluoro-5-iodo-N-methylbenzamide, (prepared as described in PREPARATION 39), (0.39 g, 1.39 mmol) in triethylamine (6 mL, 43 mmol) and heat at 70° C. After 10 min, add toluene (10 mL) to the solidified reaction mixture and heat at 70° C. for 1 h. Concentrate and purify using silica gel chromatography, eluting with 40:60 ethyl acetate:hexanes, to give the title compound as a white solid (300 mg, 72%).

$^1$H NMR (300 MHz, CDCl$_3$) δ 3.05-3.07 (m, 3H), 6.74 (br s, 1H), 7.11-7.18 (m, 1H), 7.59-7.64 (m, 1H), 7.80-7.81 (m, 1H), 8.29-8.32 (m, 1H), 8.53 (d, J=2.3 Hz, 1H), 8.63 (d, J=1.7 Hz, 1H); MS (APCI): m/z=289 [M+H]$^+$.

Example 138

N-[5-(5-Cyanopyridin-3-ylethynyl)-2-fluorobenzyl] acetamide

Add zinc (II) bromide (313 mg, 1.20 mmol), triethylamine (0.67 mL, 4.80 mmol), 5-bromonicotinonitrile (183 mg, 1.00 mmol), tetrakis(triphenylphosphine)palladium (0) (58 mg, 0.050 mmol), and a 1.0 M solution of tetrabutylammonium fluoride (2.0 mL) in tetrahydrofuran to a solution of N-(2-fluoro-5-trimethylsilanylethynylbenzyl)-acetamide, (prepared as described in PREPARATION 31), (289 mg, 1.10 mmol) in anhydrous tetrahydrofuran (2.5 mL) under nitrogen. Heat to 60° C. for 5 h, cool to room temperature, and filter through diatomaceous earth. Concentrate and purify the residue by silica gel chromatography, eluting with 100:0 to 50:50 hexanes:ethyl acetate, to give the title compound as a white crystalline solid (122 mg, 42%).

$^1$H NMR (400 MHz, DMSO-d$_6$) δ 1.85 (s, 3H), 4.25 (d, J=5.7 Hz, 2H), 7.26 (dd, J=10.1, 8.4 Hz, 1H), 7.55-7.48 (m, 2H), 8.36 (t, J=5.7 Hz, 1H), 8.53 (t, J=2.2 Hz, 1H), 8.98 (s, 1H), 8.99 (s, 1H); MS (ES): m/z=294.2 [M+H]$^+$.

Example 139

5-(3-Aminomethyl-4-fluorophenylethynyl)-nicotinonitrile

Dissolve [5-(5-cyanopyridin-3-ylethynyl)-2-fluorobenzyl]carbamic acid tert-butyl ester, (prepared as described in EXAMPLE 144), (390 mg, 1.11 mmol) in dichloromethane (7.5 mL) and treat with trifluoroacetic acid (2.57 mL, 33.3 mmol). After stirring for 1.5 h, dilute with dichloromethane and wash with an aqueous saturated solution of sodium bicarbonate and an aqueous saturated solution of sodium chloride. Dry (sodium sulfate), filter, and concentrate. Purify the residue by silica gel chromatography, eluting with a gradient from 90:10 to 75:25 (98:2 dichloromethane:7 N ammonia in methanol):(9:2 acetonitrile:7 N ammonia in methanol), to give the title compound as a white crystalline solid (270 mg, 97%).

$^1$H NMR (400 MHz, DMSO-d$_6$) δ 1.83 (s, 2H), 3.73 (s, 2H), 7.20 (dd, J=10.1, 8.4 Hz, 1H), 7.49-7.45 (m, 1H), 7.73 (dd, J=7.0, 2.2 Hz, 1H), 8.51 (t, J=2.0 Hz, 1H), 8.97 (d, J=1.8 Hz, 1H), 8.98 (d, J=1.8 Hz, 1H); MS (ES): m/z=252.2 [M+H]$^+$.

Example 140

5-(3-Dimethylaminomethyl-4-fluorophenylethynyl)-nicotinonitrile

Treat 5-(3-chloromethyl-4-fluorophenylethynyl)-nicotinonitrile, (prepared as described in PREPARATION 32), (100 mg, 0.37 mmol) with a 2.0 M solution of dimethylamine in tetrahydrofuran (3 mL) and heat at 70° C. in a sealed tube for 2 h. Cool to room temperature, dilute with ethyl acetate, and wash with an aqueous saturated solution of sodium bicarbonate and an aqueous saturated solution of sodium chloride. Dry (sodium sulfate), filter, and concentrate. Purify by silica gel chromatography, eluting with a gradient from 50:50 hexanes:dichloromethane to 90:10 (50:50 hexanes:dichloromethane):methanol, to give a yellow oil. Dissolve the oil in diethyl ether and extract twice with 1 N hydrochloric acid. Combine the aqueous layers and make basic with a 1 N sodium hydroxide. Extract the resultant purple aqueous layer three times with ethyl acetate. Combine the organic extracts, wash with an aqueous saturated solution of sodium chloride, dry (sodium sulfate), filter, and concentrate to an oil. Concentration of the oil from diethyl ether provides the title compound as a crystalline solid (60 mg, 58%).

$^1$H NMR (400 MHz, DMSO-d$_6$) δ 2.13 (s, 6H), 3.42 (s, 2H), 7.25 (dd, J=9.9, 8.6 Hz, 1H), 7.53 (ddd, J=8.5, 4.9, 2.3 Hz, 1H), 7.62 (dd, J=7.0, 2.2 Hz, 1H), 8.52 (t, J=2.2 Hz, 1H), 8.99-8.98 (m, 2H); MS (ES): m/z=280.2 [M+H]$^+$; Anal Calcd for C$_{17}$H$_{14}$FN$_3$: C, 73.10; H, 5.05; N, 15.04. Found: C, 73.23; H, 5.17; N, 14.89.

Example 141

5-(3-Cyanomethyl-4-fluorophenylethynyl)-nicotinonitrile

Dissolve 5-(3-chloromethyl-4-fluorophenylethynyl)-nicotinonitrile, (prepared as described in PREPARATION 32), (120 mg, 0.44 mmol) in N,N-dimethylformamide (2.2 mL) and treat with sodium cyanide (86 mg, 1.8 mmol). After stirring for 30 min at room temperature, dilute with ethyl acetate and wash with an aqueous saturated solution of sodium bicarbonate and an aqueous saturated solution of sodium chloride. Dry (sodium sulfate), filter, and concentrate. Purify by silica gel chromatography, eluting with 70:30 hexanes:ethyl acetate, to give the title compound as a white crystalline solid (90 mg, 78%).

$^1$H NMR (400 MHz, DMSO-d$_6$) δ 4.08 (s, 2H), 7.38 (dd, J=9.9, 8.6 Hz, 1H), 7.65-7.61 (m, 1H), 7.68 (dd, J=7.3, 2.0 Hz, 1H), 8.54 (t, J=2.0 Hz, 1H), 8.99 (s, 1H), 9.00 (s, 1H); MS (ES): m/z=262.0 [M+H]$^+$.

Example 142

5-(4-Fluoro-3-hydroxymethylphenylethynyl)-nicotinonitrile

Dissolve zinc (II) bromide (374 mg, 14.3 mmol) in tetrahydrofuran (30 mL) and treat with triethylamine (7.96 mL, 57.1 mmol). After 5 min add 2-fluoro -5-iodobenzyl alcohol, (prepared as described in PREPARATION 33), (3.00 g, 11.9 mmol), 5-ethynylnicotinonitrile, (prepared as described in PREPARATION 4), (1.83 g, 14.3 mmol) and tetrakis(triphenylphosphine)palladium (0) (688 mg, 0.595 mmol) to the reddish solution. Heat to 60° C. for 2 h, cool to room temperature, and filter through diatomaceous earth. Purify by silica gel chromatography, eluting with 75:25 to 60:40 hexanes:ethyl acetate, to give the title compound as a yellow crystalline solid (1.85 g, 62%).

$^1$H NMR (400 MHz, DMSO-d$_6$) δ 4.53 (d, J=5.7 Hz, 2H), 5.37 (t, J=5.7 Hz, 1H), 7.23 (dd, J=9.9, 8.6 Hz, 1H), 7.52 (ddd, J=8.4, 4.8 Hz, 2.2 Hz, 1H), 7.67 (dd, J=7.3, 2.4 Hz, 1H), 8.53 (t, J=2.0 Hz, 1H), 8.98 (t, J=1.8 Hz, 2H); MS (ES): m/z=253.0 [M+H]$^+$; Anal Calcd for C$_{15}$H$_9$FN$_2$O 0.1H$_2$O: C, 70.92; H, 3.61; N, 10.83. Found: C, 70.78; H, 3.65; N, 11.03.

Example 143

N-[5-(5-Cyanopyridin-3-ylethynyl)-2-fluorobenzyl]-methanesulfonamide

Dissolve zinc (II) bromide (94 mg, 0.36 mmol) in tetrahydrofuran (0.75 mL) and treat with triethylamine (0.20 mL, 1.4 mmol). After 4 min add 5-bromonicotinonitrile (55 mg, 0.30 mmol), N-(2-fluoro-5-trimethylsilanylethynylbenzyl) -methanesulfonamide, (prepared as described in PREPARATION 34), (100 mg, 0.33 mmol) and tetrakis(triphenylphosphine) palladium (0) (17 mg, 0.015 mmol) to the reddish solution. Heat to 60° C. and add a 1 M solution of tetrabutylammonium fluoride (0.36 mL) in tetrahydrofuran. After 1 h add additional 1 M tetrabutylammonium fluoride (0.3 mL) in tetrahydrofuran and stir an additional 30 min. Cool to room temperature and filter through diatomaceous earth washing with ethyl acetate. Purify by silica gel chromatography, eluting with a gradient from 60:40 to 40:60 (7:30 hexanes:dichloromethane):ethyl acetate, to give the title compound as a white crystalline solid (50 mg, 50%).

$^1$H NMR (400 MHz, DMSO-d$_6$) δ 2.91 (s, 3H), 4.20 (d, J=6.2 Hz, 2H), 7.29 (dd, J=9.9, 8.6 Hz, 1H), 7.62-7.54 (m, 2H), 7.66 (dd, J=7.0, 2.2 Hz, 1H), 8.54 (t, J=2.0 Hz, 1H), 9.00-8.99 (m, 2H); MS (ES): m/z=330.0 [M+H]$^+$; Anal Calcd for C$_{16}$H$_{12}$FN$_3$O$_2$S.0.3H$_2$O: C, 57.41; H, 3.79; N, 12.55. Found: C, 57.71; H, 3.73; N, 12.18.

Example 144

[5-(5-Cyanopyridin-3-ylethynyl)-2-fluororbenzyl] carbamic acid tert-butyl ester

Prepare according to the general procedure outlined in EXAMPLE 138 using (2-fluoro-5-trimethylsilanylethynyl-benzyl)-carbamic acid tert-butyl ester, (prepared as described in PREPARATION 36), (0.550 g, 1.71 mmol). Purify by silica gel chromatography, eluting with 70:30 to 50:50 hexanes:ethyl acetate. Further purify by silica gel chromatography, eluting with 85:15 to 75:25 (70:30 hexanes:dichloromethane):ethyl acetate, to give the title compound as a pale-yellow oil, which crystallizes upon standing (310 mg, 56%).

$^1$H NMR (400 MHz, DMSO-d$_6$) δ 1.35 (s, 9H), 4.15 (d, J=5.7 Hz, 2H), 7.25 (dd, J=9.9, 8.6 Hz, 1H), 7.42 (t, J=5.9 Hz, 1H), 7.54-7.48 (m, 2H), 8.53 (t, J=2.0 Hz, 1H), 8.98 (t, J=2.0 Hz, 2H); MS (ES): m/z=296.0 [M-tert-Bu+2H]$^+$.

Example 145

5-(3-{[(2-Cyanoethyl)methylamino]methyl}-4-fluorophenylethynyl)-nicotinonitrile

Dissolve 5-(4-fluoro-3-formylphenylethynyl)nicotinonitrile, (prepared as described in PREPARATION 38) (100 mg, 0.40 mmol) in dichloroethane (2 mL) and treat with N-methyl-β-alaninenitrile (0.041 mL, 0.44 mmol) and sodium triacetoxyborohydride (110 mg, 0.52 mmol). After stirring for 5.5 h, quench with water (2 mL), dilute with dichloromethane and extract three times with 0.5 N hydrochloric acid, but thin layer chromatography shows some product still remaining in the organic phase. Add 1 N sodium hydroxide to the aqueous layer until it is basic then extract twice with ethyl acetate. Combine the dichloromethane layer with the ethyl acetate extracts and wash with an aqueous saturated solution of sodium chloride, dry (sodium sulfate), filter, and concentrate. Purify by silica gel chromatography, eluting with 90:10 to 80:20 dichloromethane:ethyl acetate, to give the title compound as a white crystalline solid (55 mg, 43%).

$^1$H NMR (400 MHz, DMSO-d$_6$) δ 2.15 (s, 3H), 2.70-2.60 (m, 4H), 3.58 (s, 2H), 7.26 (dd, J=9.9, 8.6 Hz, 1H), 7.54 (ddd, J=8.5, 5.2, 2.3 Hz, 1H), 7.68 (dd, J=7.0, 2.2 Hz, 1H), 8.51 (t, J=2.2 Hz, 1H), 8.97 (d, J=1.8 Hz, 1H), 8.98 (d, J=1.8 Hz, 1H);

MS (ES): mm/z=319.2 [M+H]⁺; Anal Calcd for $C_{19}H_{15}FN_4$: C, 71.68; H, 4.75; N, 17.60. Found: C, 71.08; H, 4.95; N, 16.73.

Example 146

5-{4-Fluoro-3-[(isopropylmethylamino)-methyl]-phenylethynyl) -nicotinonitrile Prepare according to the general procedure outlined in EXAMPLE 145 using N-methylisopropylamine (0.046 mL, 0.44 mmol). Purify by silica gel chromatography, eluting with 100:0 to 90:10 dichloromethane:methanol and then 80:20 dichloromethane:methanol, to give the title compound. Further purify by silica gel chromatography, eluting with 100:0 to 50:50 (75:25 dichloromethane:acetonitrile):(80:20 dichloromethane:methanol) to give the title compound as a white crystalline solid (66 mg, 54%).

¹H NMR (400 MHz, DMSO-d₆) δ 1.01 (d, J=6.2 Hz, 6H), 2.07 (s, 3H), 2.84 (sept, J=6.6 Hz, 1H), 3.51 (s, 2H), 7.25 (dd, J=9.9, 8.6 Hz, 1H), 7.54-7.50 (m, 1H), 7.65 (dd, J=7.0, 2.2 Hz, 1H), 8.56 (t, J=2.0 Hz, 1H), 9.02-9.00 (m, 2H); MS (ES): m/z=308.3 [M+H]⁺.

Example 147

5-[4-Fluoro-3-(isopropylaminomethyl)-phenylethynyl]-nicotinonitrile

Prepare according to the general procedure outlined in EXAMPLE 145 using isopropylamine (0.037 mL, 0.44 mmol) except no product remains in the dichloromethane layer after washing with 0.5 N hydrochloric acid. Thus the dichloromethane layer is not combined with the ethyl acetate extracts. Purify by silica gel chromatography, eluting with 100:0 to 50:50 (75:25 dichloromethane:acetonitrile):(80:20 dichloromethane:methanol), to give the title compound as a white crystalline solid (47 mg, 40%).

¹H NMR (400 MHz, DMSO-d₆) δ 0.99 (d, J=6.6 Hz, 6H), 2.70 (sept, J=6.4 Hz, 1H), 3.72 (s, 2H), 7.24 (dd, J=9.9, 8.6 Hz, 1H), 7.53-7.49 (m, 1H), 7.74 (dd, J=7.0, 2.2 Hz, 1H), 8.54 (t, J=2.0 Hz, 1H), 9.00 (t, J=1.8 Hz, 2H); MS (ES): m/z=294.2 [M+H]⁺; Anal Calcd for $C_{18}H_{16}FN_3.0.3H_2O$: C, 72.37; H, 5.60; N, 14.07. Found: C, 72.19; H, 5.42; N, 13.77.

Example 148

5-[4-Fluoro-3-(propylaminomethyl)-phenylethynyl]-nicotinonitrile

Prepare according to the general procedure outlined in EXAMPLE 145 using n-propylamine (0.035 mL, 0.44 mmol) except is no product remains in the dichloromethane layer after washing with 0.5 N hydrochloric acid. Thus the dichloromethane layer is not combined with the ethyl acetate extracts. Purify by silica gel chromatography, eluting with a gradient from 100:0 80:20 dichloromethane:methanol, to give the title compound as a white crystalline solid (66 mg, 56%).

¹H NMR (400 MHz, DMSO-d₆) δ 0.85 (t, J=7.3 Hz, 3H), 1.42 (sextet, J=7.2 Hz, 2H), 2.44 (t, J=7.0 Hz, 2H), 2.14 (s, 1H), 3.71 (s, 2H), 7.24 (dd, J=9.9, 8.6 Hz, 1H), 7.53-7.49 (m, 1H), 7.71 (dd, J=7.0, 2.2 Hz, 1H), 8.54 (t, J=2.0 Hz, 1H), 9.00 (t, J=2.2 Hz, 2H); MS (ES): m/z=294.2 [M+H]⁺; Anal Calcd for $C_{18}H_{16}FN_3$: C, 73.70; H, 5.50; N, 14.32. Found: C, 73.71; H, 5.65; N, 14.00.

Example 149

5-[4-Fluoro-3-(ethylaminomethyl)-phenylethynyl]-nicotinonitrile

Prepare according to the general procedure outlined in EXAMPLE 145 using a 2 M solution of ethylamine in tetrahydrofuran (0.22 mL, 0.44 mmol) except no product remains in the dichloromethane layer after washing with 0.5 N hydrochloric acid. Thus the dichloromethane layer is not combined with the ethyl acetate extracts. Purify by silica gel chromatography, eluting with a gradient from 100:0 to 80:20 dichloromethane:methanol, to give the title compound as a white crystalline solid (54 mg, 48%).

¹H NMR (400 MHz, DMSO-d₆) δ 1.02 (t, J=7.3 Hz, 3H), 2.15 (s, 1H), 2.51 (q, J=7.0 Hz, 2H), 3.71 (s, 2H), 7.24 (dd, J=9.9, 8.6 Hz, 1H), 7.53-7.49 (m, 1H), 7.71 (dd, J=7.3, 2.0 Hz, 1H), 8.54 (t, J=2.0 Hz, 1H), 9.00 (t, J=1.8 Hz, 2H); MS (ES): m/z=280.2 [M+H]⁺; Anal Calcd for $C_{17}H_{14}FN_3.0.1H_2O$: C, 72.63; H, 5.09; N, 14.95. Found: C, 72.64; H, 5.35; N, 14.58.

Example 150

5-[4-Fluoro-3-(methylaminomethyl)-phenylethynyl]-nicotinonitrile

Prepare according to the general procedure outlined in EXAMPLE 145 using a 2 M solution of methylamine in tetrahydrofuran (0.22 mL, 0.44 mmol) except no product remains in the dichloromethane layer after washing with 0.5 N hydrochloric acid. Thus the dichloromethane layer is not combined with the ethyl acetate extracts. Purify by silica gel chromatography, eluting with a gradient from 100:0 to 80:20 dichloromethane:methanol, to give the title compound as a white crystalline solid (22 mg, 21%).

¹H NMR (400 MHz, DMSO-d₆) δ 2.26 (s, 3H), 3.67 (s, 2H), 7.25 (dd, J=10.1, 8.4 Hz, 1H), 7.54-7.50 (m, 1H), 7.69 (dd, J=7.0, 2.2 Hz, 1H), 8.54 (t, J=2.0 Hz, 1H), 9.00 (t, J=2.0 Hz, 2H); MS (ES): nm/z=266.0 [M+H]⁺; Anal Calcd for $C_{16}H_{12}FN_3$: C, 72.44; H, 4.56; N, 15.84. Found: C, 72.36; H, 5.03; N, 14.92.

Example 151

3-Oxo-3-(5-phenylethynyl-pyridin-3-yl)-propionic acid methyl ester

Prepare essentially as described in EXAMPLE 32 using 3-(5-bromopyridin-3-yl)-3-oxopropionic acid methyl ester (0.387 g, 1.5 mmol) to give the title compound (124 mg, 30%).

¹H NMR (300 MHz, CDCl₃) δ 3.82 (s, 3H), 5.74 (s, 1H), 7.37 (m, 3H), 7.55 (m, 2H), 8.16 (s, 1H), 8.18 (br s, 1H), 8.91 (br s, 1H); MS (ES): m/z=280.1 [M+H]⁺.

Example 152

(5-Phenylethynyl-pyridin-3-yl)-methanol

Add sodium cyanoborohydride (0.31 g, 4.98 mmol) to a solution of 5-phenylethynyl-pyridine-3-carbaldehyde, (prepared as described in EXAMPLE 5), (0.86 g, 4.15 mmol) and stir at room temperature for 2 h. Dilute with ethyl acetate, wash with an aqueous saturated solution of bicarbonate, dry (magnesium sulfate), filter and concentrate. Purify by silica gel chromatography, eluting with 0:100 to 50:50 ethyl acetate:hexanes, to give the title compound as a colorless oil which solidifies on standing (0.465 g, 53%).

$^1$H NMR (400 MHz, DMSO-d$_6$) δ 2.96 (s, 1H), 4.74 (s, 2H), 7.37-7.32 (m, 2H), 7.55-7.49 (m, 3H), 7.86 (s, 1H), 8.51 (s, 1H), 8.65 (s, 1H); MS (ES): m/z=210 [M+H]$^+$.

Example 153

[5-(5-Cyanopyridin-3-ylethynyl)-2-fluorobenzyl]-carbamic acid ethyl ester

Prepare according to the general procedure outlined in EXAMPLE 138 using (2-fluoro-5-trimethylsilanylethynyl-benzyl)-carbamic acid ethyl ester, (prepared as described in PREPARATION 49), (0.322 g, 1.10 mmol). Purify by silica gel chromatography, eluting with 70:30 to 50:50 hexanes:ethyl acetate. Further purify by reverse phase chromatography, eluting with a gradient from 95:5 to 10:90 (0.1% aqueous trifluoroacetic acid):(0.1% trifluoroacetic acid in acetonitrile). Concentrate the fractions and partition between ethyl acetate and a saturated aqueous solution of sodium bicarbonate. Wash the organic with saturated aqueous sodium chloride, dry (sodium sulfate), filter, and concentrate to give the title compound as a white crystalline solid (128 mg, 40%).

$^1$H NMR (400 MHz, DMSO-d$_6$) δ 1.13 (t, J=7.3 Hz, 3H), 3.97 (q, J=7.0 Hz, 2H), 4.20 (d, J=6.2 Hz, 2H), 7.26 (dd, J=9.7, 8.4 Hz, 1H), 7.49-7.55 (m, 2H), 7.67 (t, J=5.9 Hz, 1H), 8.53 (t, J=2.0 Hz, 1H), 8.99 (d, J=2.2 Hz, 2H); MS (ES): m/z=324.0 [M+H]$^+$; Anal Calcd for C$_{18}$H$_{14}$FN$_3$O$_2$: C, 66.87; H, 4.36; N, 13.00. Found: C, 66.62; H, 4.31; N, 12.81.

Example 154

(5-Phenylethynyl-pyridin-3-yl)-carbamic acid tert-butyl ester

Stir a mixture of 3-bromo-5-phenylethynyl-pyridine, (prepared as described in EXAMPLE 9), (2.5 g, 10 mmol), copper (I) iodide (0.190 g, 1 mmol), potassium carbonate (2.76 g, 20 mmol), carbamic acid tert-butyl ester (1.17 g, 10 mmol), N,N'-dimethylethylenediamine (0.220 mL, 2 mmol) in 1,4-dioxane (10 mL) at 110° C. in a sealed tube for 36 h. Cool to room temperature and concentrate. Purify by silica gel chromatography, eluting with 100:0 dichloromethane:methanol to 90:10 dichloromethane:methanol, and then crystallizing from ethyl acetate to give the title compound (430 mg, 15%).

$^1$H NMR (300 MHz, CH$_3$OH-d4) δ 1.54 (s, 9H), 7.42 (m, 3H), 7.55 (m, 2H), 8.10 (s, 1H), 8.31 (br s, 1H), 8.54 (br s, 1H); $^{13}$C NMR (75 MHz, CH$_3$OH-d$_4$) δ 28.7, 81.9, 86.2, 93.1, 122.9, 128.1, 128.8, 129.2, 132.1, 139.0, 146.5, 153.0; MS (ES): m/z 295.1 [M+H]$^+$.

Example 155

5-Phenylethynyl-pyridin-3-ylamine dihydrochloride

Prepare essentially as described in EXAMPLE 2 from 5-phenylethynyl-pyridin-3-yl)-carbamic acid tert-butyl ester, (prepared as described in EXAMPLE 154), (0.380 g, 1.3 mmol) in 1,4-dioxane (1 mL) and hydrogen chloride (3 mL, 12 mmol) to give the title compound (280 mg, 81%).

$^1$H NMR (300 MHz, CH$_3$OH-d4) δ 7.47 (m, 3H), 7.58 (m, 2H), 7.75 (s, 1H), 8.00 (s, 1H), 8.12 (s, 1H); $^{13}$C NMR (75 MHz, CH$_3$OH-d4) δ 83.9, 96.4, 122.9, 125.8, 126.5, 130.2, 131.2, 131.3, 131.4, 133.4, 150.1; MS (ES): m/z=195.1 [M+H]$^+$.

Example 156

N-(5-Phenylethynyl-pyridin-3-yl)-methanesulfonamide

Add methanesulfonyl chloride (0.035 mL, 0.45 mmol) to a solution of 5-phenylethynyl-pyridin-3-ylamine dihydrochloride, (prepared as described in EXAMPLE 155), (0.120 g, 0.45 mmol) and pyridine (0.075 mL, 0.90 mmol) in dichloromethane (2.5 mL) at 0° C. Warm to room temperature and stir overnight. Add pyridine (0.020 mL, 0.24 mmol) and methanesulfonyl chloride (0.010 mL, 0.11 mmol), stir for 20 h and add water. Separate the layers and concentrate the organic phase. Purify by silica gel chromatography, eluting with 1.1 hexanes:ethyl acetate, to give the title compound (0.091 g, 75%).

$^1$H NMR (300 MHz, CDCl$_3$) δ 3.07 (s, 3H), 7.38 (m, 3H), 7.53 (m, 2H), 7.87 (t, J=2.1 Hz, 1H), 8.37 (d, J=1.8 Hz, 1H), 8.51 (br s, 1H); $^{13}$C NMR (75 MHz, CDCl$_3$) δ 40.4, 85.3, 94.2, 121.8, 122.4, 128.9, 129.5, 129.8, 132.1, 134.7, 140.3, 148.0; MS (ES): m/z=273.1 [M+H]$^+$.

Example 157

N-(5-Phenylethynyl-pyridin-3-yl)-acetamide

Prepare essentially as described in EXAMPLE 156 with acetyl chloride (0.032 mL, 0.45 mmol and then 0.010 mL, 0.11 mmol) to give the title compound (85 mg, 80%).

$^1$H NMR (300 MHz, CDCl$_3$) δ 2.16 (s, 3H), 7.34 (m, 3H), 7.49 (m, 2H), 8.36 (br s, 1H), 8.40 (br s, 1H), 8.42 (br s, 1H); $^{13}$C NMR (75 MHz, CDCl$_3$) δ 24.0, 85.5, 93.1, 121.0, 122.4, 128.5, 129.0, 129.6, 131.8, 135.4, 139.1, 146.3, 170.0; MS (ES): m/z=237.1 [M+H]$^+$.

Example 158

(5-Phenylethynyl-pyridin-3-yl)-carbamic acid ethyl ester

Prepare using the general procedure outlined in EXAMPLE 156 using ethyl chloroformate (0.043 mL, 0.45 mmol and then 0.011 mL, 0.11 mmol) to give the title compound (91 mg, 76%).

$^1$H NMR (300 MHz, CDCl$_3$) δ 1.34 (t, J=7.1 Hz, 3H), 4.27 (q, J=7.1 Hz, 2H), 7.39 (m, 3H), 7.52 (m, 2H), 7.62 (br s, 1H), 8.22 (br s, 1H), 8.46 (br s, 2H); $^{13}$C NMR (75 MHz, CDCl$_3$) δ 14.9, 62.2, 86.1, 93.2, 121.1, 122.8, 128.3, 128.8, 129.2, 132.1, 135.3, 139.1, 146.7, 154.0; MS (ES): m/z=267.1 [M+H]$^+$.

Example 159

N-[5-(5-Cyanopyridin-3-ylethynyl)-2-fluorophenyl]-isobutyramide

Add a solution of isobutynyl chloride (0.09 g, 1.08 mmol) dissolved in tetrahydrofuran to a solution of 5-(3-amino-4-fluorophenylethynyl)-nicotinonitrile, (prepared as described in EXAMPLE 160), (0.2 g, 0.8 mmol) in anhydrous tetrahydrofuran and stir overnight at room temperature. Pour into ethyl acetate, wash with water and an aqueous saturated solution of sodium chloride, dry (potassium carbonate), filter and concentrate. Purify the residue by silica gel chromatography, eluting with 100:0 to 95:5 dichloromethane:ethyl acetate, to give the title compound as a white solid (210 mg, 84%).

¹H NMR (400 MHz, DMSO-d₆) δ 1.10 (d, J=7.0 Hz, 6H), 2.80-2.73 (m, 1H), 7.39-7.33 (m, 2H), 8.21-8.16 (m, 1H), 8.57 (t, J=2.0 Hz, 1H), 9.03-9.01 (m, 2H), 9.78 (s, 1H); HRMS calcd for $C_{18}H_{15}FN_3O$ 308.1199. Found 308.1207.

Example 160

5-(3-Amino-4-fluorophenylethynyl)-nicotinonitrile

Prepare essentially as described in EXAMPLE 138 using 3-bromonicotinonitrile (3.4 g, 18.3 mmol) and 2-fluoro-5-trimethylsilanylethynyl-phenylamine, (prepared as described in PREPARATION 41), (3.8 g, 18.3 mmol) to give the title compound as a white solid (2.8 g, 65%).

¹H NMR (400 MHz, DMSO-d₆) δ 5.41 (s, 2H), 6.75 (ddd, J=8.1 Hz, J=4.6 Hz, J=2.0 Hz, 1H), 6.96 (dd, J=8.6 Hz, J=2.0 Hz, 1H), 7.06 (dd, J=11.6 Hz, J=8.1 Hz, 1H), 8.52 (t, J=2.0 Hz, 1H), 8.99 (dd, J=6.6 Hz, J=2.2 Hz, 2H); HRMS calcd for $C_{14}H_9FN_3$ 238.0702. Found 238.0775.

Example 161

5-(4-Fluoro-3-nitrophenylethynyl)-nicotinonitrile

Prepare essentially as described in EXAMPLE 142 using 4-bromo-1-fluoro-2-nitrobenzene (1.0 g, 4.5 mmol) and 5-ethynylnicotinonitrile, (prepared as described in PREPARATION 4), (0.7 g, 5.5 mmol) to give the title compound as a yellow solid (0.11 g, 9%).

¹H NMR (400 MHz, DMSO-d₆) δ 7.71 (dd, J=11.2 Hz, J=8.6 Hz, 1H), 8.03 (ddd, J=8.6 Hz, J=4.2 Hz, J=2.2 Hz, 1H), 8.40 (dd, J=7.0 Hz, J=2.2 Hz, 1H), 8.61 (t, J=2.0 Hz, 1H), 9.06 (t, J=2.0 Hz, 2H); LC-MS (ES): m/z=268 [M+1]⁺.

Example 162

3-(3-Bromo-4-fluorophenylethynyl)-5-methoxypyridine

Add bis(triphenylphosphine)palladium (II) dichloride (93 mg, 0.13 mmol), copper (I) iodide (50 mg, 0.26 mmol), and 3-ethynyl-5-methoxypyridine, (prepared as described in PREPARATION 10), (350 mg, 2.6 mmol) to a solution of 2-bromo-1-fluoro-4-iodobenzene, (prepared as described in PREPARATION 43), (1.03 g, 3.4 mmol) in triethylamine (4.0 mL, 39.5 mmol). Stir at room temperature for 20 h then concentrate. Purify by silica gel chromatography, eluting with 100:0 to 80:20 dichloromethane:ethyl acetate, followed by a second silica gel chromatography, eluting with 75:25 to 60:40 hexanes:ethyl acetate, to give the title compound as a white solid (750 mg, 93%).

¹H NMR (300 MHz, CDCl₃) δ 3.88 (s, 3H), 7.08-7.17 (t, J=8.4 Hz, 1H), 7.27-7.34 (m, 1H), 7.43-7.50 (m, 1H), 7.74-7.80 (m, 1H), 8.27-8.30 (d, J=2.9 Hz, 1H), 8.33-8.37 (d, J=1.6 Hz, 1H); MS (APCI): m/z=306 [M+H]⁺.

Example 163

N-Hydroxy-5-phenylethynyl-nicotinamidine hydrochloride

Add hydroxylamine hydrochloride (0.55 g, 7.8 mmol) to a suspension of 5-phenylethynylnicotinonitrile (0.20 g, 0.98 mmol) and potassium carbonate (0.68 g, 4.9 mmol) and heat at reflux for 2 h. Cool the reaction mixture to room temperature, filter away any solids and concentrate. Purify by silica gel chromatography, eluting with 40:60 ethyl acetate:hexanes, to obtain the free base of the title compound as a white solid. Dissolve the free base in diethyl ether, add a 1 M solution of hydrogen chloride in diethyl ether (1.1 eq) and collect the resulting precipitated solids by filtration to give the title compound (0.1 g, 37%).

¹H NMR (400 MHz, CH₃OH-d4) δ 7.61-7.56 (m, 5H), 8.30 (t, J=2.2 Hz, 1H), 8.83 (d, J=2.2 Hz, 1H), 9.02 (d, J=1.5 Hz, 1H); MS (ES): m/z=238 [M+H]⁺.

Example 164

Acetic acid 5-phenylethynyl-pyridin-3-yl-methyl ester hydrochloride

Add acetic anhydride (2 mL) to a solution of (5-phenylethynyl-pyridin-3-yl)-methanol, (prepared as described in EXAMPLE 152), (0.1 g, 0.5 mmol) in pyridine. Stir at room temperature overnight and concentrate. Dissolve in ethyl acetate, wash with water, dry (magnesium sulfate), filter and concentrate. Purify by silica gel chromatography, eluting with 0:100 to 40:60 ethyl acetate:hexanes, to give the free base of the title compound as a white solid. Convert the free base to the hydrochloride salt as described in EXAMPLE 163 to give the title compound (0.12 g, 87%).

¹H NMR (400 MHz, DMSO-d₆) δ 2.06 (s, 3H), 5.13 (s, 2H), 7.45-7.41 (m, 3H), 7.59-7.56 (m, 2H), 8.09 (t, J=1.8 Hz, 1H), 8.64 (s, 1H), 8.77 (d, J=0.9 Hz, 1H); MS (ES): m/z=252 [M+H]⁺.

Example 165

3-Methoxymethyl-5-phenylethynyl-pyridine hydrochloride

Add iodomethane (0.06 g, 0.44 mmol) and a solution of (5-phenylethynyl-pyridin-3-yl)-methanol, (prepared as described in EXAMPLE 152), (0.12 g, 0.55 mmol) in N,N-dimethylformamide (1.0 mL) to a suspension of sodium hydride (0.022 g, 0.55 mmol) in N,N-dimethylformamide (1.0 mL) and stir at room temperature for 2 h. Dilute with ethyl acetate, wash with water and an aqueous saturated solution of sodium chloride, dry (magnesium sulfate), filter and concentrate. Purify the residue by silica gel chromatography, eluting with 10:90 ethyl acetate:hexanes, to give the free base of the title compound as a white solid. Convert the free base to the hydrochloride salt as described in EXAMPLE 163 to give the title compound (0.073 mg, 53%).

¹H NMR (400 MHz, DMSO-d₆) δ 2.71 (s, 3H), 3.89 (s, 2H), 6.70-6.61 (m, 3H), 6.84-6.80 (m, 2H), 7.85 (s, 1H), 7.97 (s, 1H), 8.19 (s, 1H); MS (ES): m/z=224 [M+H]⁺.

Example 166

1-(5-Phenylethynyl-pyridin-3-yl)-ethanone

Add a 3.0 M solution of methylmagnesium bromide (1.25 mL, 3.8 mmol) in diethyl ether dropwise to a cooled solution of N-methoxy-N-methyl-5-phenylethynyl-nicotinamide, (prepared as described in PREPARATION 2), (1.00 g, 3.7 mmol) in tetrahydrofuran (8.0 mL) at 0° C. Warm to room temperature, stir overnight and dilute with ethyl acetate. Wash with an aqueous saturated solution of ammonium chloride, dry (magnesium chloride), filter and concentrate. Purify the residue by silica gel chromatography, eluting with 10:90 to 30:70 tetrahydrofuran:hexanes, to give the title compound as a white solid (0.70 g, 84%).

¹H NMR (400 MHz, CDCl₃) δ 2.66 (s, 3H), 7.41-7.37 (m, 3H), 7.59-7.53 (m, 2H), 8.34 (t, J=2.2 Hz, 1H), 8.91 (d, J=1.8 Hz, 1H), 9.08 (d, J=1.8 Hz, 1H); MS (ES): m/z=222 [M+H]⁺.

Example 167

C-(5-Phenylethynyl-pyridin-3-yl)-methylamine trifluoroacetate

Add zinc dust (0.39 g, 6.04 mmol) in small portions to a solution of 5-phenylethynyl-pyridine-3-carbaldehyde oxime hydrochloride, (prepared as described in EXAMPLE 6), (0.16 g, 0.60 mmol) in trifluoroacetic acid (1.4 mL) while keeping the internal reaction temperature between about 15-20° C. using a chilled water bath. After 15 min, add a 1:1 mixture of 2 N sodium hydroxide and chloroform, while stirring vigorously and cooling in an ice bath. Filter away the solids and wash the filtrate with water, an aqueous saturated solution of sodium chloride, dry (magnesium sulfate), filter and concentrate. Purify the residue by reverse phase HPLC, eluting with 5:95 to 100:0 acetonitrile:water with 0.02% trifluoroacetic acid, to give the title compound as pale yellow solid (0.015 g, 11.9%).
¹H NMR (400 MHz, DMSO-d₆) δ 4.11 (d, J=4.4 Hz, 2H), 7.47-7.42 (m, 3H), 7.59-7.53 (m, 2H), 8.08 (t, J=2.0 Hz, 1H), 8.34 (s, 2H), 8.64 (s, 1H), 8.74 (s, 1H); MS (ES): m/z 209 [M+H]⁺.

Example 168

5-(3-Fluorophenylethynyl)-nicotinic acid ethyl ester

Add a 1 M solution of tetrabutylammonium fluoride (0.88 g, 3.38 mmol) in tetrahydrofuran to a mixture of 3-iodofluorobenzene (0.50 g, 2.25 mmol), 5-trimethylsilanylethynyl-nicotinic acid ethyl ester, (prepared as described in PREPARATION 16), (0.84 g, 3.38 mmol), bis(triphenylphosphine) palladium (II) dichloride (0.03 g, 0.05 mmol) and copper (I) iodide (0.02 g, 0.09 mmol) at −78° C. Warm to room temperature, stir overnight and then dilute with ethyl acetate. Wash with an aqueous saturated solution of ammonium chloride, dry (magnesium sulfate), filter and concentrate. Purify the residue by silica gel chromatography, eluting with 2.5:45:52.5 ethyl acetate:chloroform:hexanes, to give the title compound as a pale yellow solid (0.46 mg, 80%).
¹H NMR (400 MHz, CDCl₃) δ 1.43 (t, J=7.3 Hz, 3H), 4.44 (q, J=7.2 Hz, 2H), 7.13-7.06 (m, 1H), 7.28-7.23 (m, 1H), 7.38-7.31 (m, 2H), 8.41 (t, J=2.0 Hz, 1H), 8.90 (s, 1H), 9.16 (s, 1H); MS (ES): m/z=270 [M+H]⁺.

Example 169

5-(3-Fluorophenylethynyl)-N,N-dimethyl-nicotinamide hydrochloride

Isolate the title compound from the crude reaction mixture in PREPARATION 18 during silica gel chromatography purification (0.086 g, 18.1%).
¹H NMR (400 MHz, DMSO-d₆) δ 2.92 (s, 3H), 2.99 (s, 3H), 7.35-7.28 (m, 1H), 7.53-7.41 (m, 3H), 8.07 (t, J=2.0 Hz, 1H), 8.65 (s, 1H), 8.83 (s, 1H); MS (ES): m/z=269 [M+H]⁺.

Example 170

3-Bromo-5-(4-fluorophenylethynyl)-pyridine

Heat a suspension of 3,5-dibromopyridine (4.00 g, 16.88 mmol), bis(triphenylphosphine)palladium (II) dichloride (0.59 g, 0.84 mmol) and copper (I) iodide (0.32 g, 1.69 mmol) in triethylamine (4.7 mL, 33.8 mmol) to 80° C. Add a solution of 1-ethynyl-4-fluorobenzene (2.03 g, 16.88 mmol) in acetonitrile (34 mL), stir for 2 h, cool to room temperature and dilute with ethyl acetate. Wash with an aqueous saturated solution of sodium bicarbonate, dry (magnesium sulfate), filter and concentrate. Purify the residue by silica gel chromatography, eluting with a 1% solution of ethyl acetate in 1:1 chloroform:hexanes, and then recrystallize from methanol to give the title compound (2.4 g, 51.5%).
¹H NMR (400 MHz, CDCl₃) δ 7.11-7.05 (m, 2H), 7.55-7.50 (m, 2H), 7.96 (t, J=2.0 Hz, 1H), 8.64 (d, J=14.1 Hz, 2H); MS (ES): m/z=277 [M+H]⁺.

Example 171

1-(5-Phenylethynyl-pyridin-3-yl)-ethanone oxime hydrochloride

Prepared in the same manner as described in EXAMPLE 6, using 1-(5-phenylethynyl-pyridin-3-yl)-ethanone, (prepared as described in EXAMPLE 166), (0.22 g, 0.97 mmol), hydroxylamine hydrochloride (0.54 g, 7.78 mmol) and potassium carbonate (0.67 g, 4.86 mmol) to give the free base of the title compound. Convert the free base to the hydrochloride salt as described in EXAMPLE 163 to give the title compound (0.112 g, 42%).
¹H NMR (400 MHz, DMSO-d₆) δ 2.19 (s, 3H), 7.48-7.42 (m, 2H), 7.63-7.57 (m, 2H), 8.23 (t, J=2.0 Hz, 1H), 8.78 (s, 1H), 8.87 (s, 1H), 11.68 (s, 1H); MS (ES): m/z=269 [M+H]⁺.

Example 172

(5-Phenylethynyl-pyridin-3-ylmethyl)-carbamic acid ethyl ester hydrochloride

Add ethylchloroformate (0.18 g, 1.63 mmol) to a solution of C-(5-phenylethynyl-pyridin-3-yl)-methylamine, (prepared as described in EXAMPLE 167), (0.20 g, 0.82 mmol) and triethylamine (0.33 g, 3.27 mmol) in dichloromethane (1.6 mL). Stir overnight, and dilute with dichloromethane. Wash with an aqueous saturated solution of sodium bicarbonate, dry (magnesium sulfate), filter and concentrate. Purify by silica gel chromatography, eluting with 50:50 ethyl acetate:hexanes, to give the free base of the title compound. Dissolve the free base in diethyl ether and add a 1 M solution of hydrogen chloride (1.1 eq.) in diethyl ether. Stir for 2 h and collect the precipitated solid by filtration to give the title compound (0.18 g, 70%).
¹H NMR (400 MHz, DMSO-d₆) δ 1.15 (t, J=7.3 Hz, 3H), 4.00 (q, J=7.0 Hz, 2H), 4.25 (d, J=6.2 Hz, 2H), 5.76 (br s, 1H), 7.47-7.43 (m, 3H), 7.62-7.56 (m, 1H), 7.77 (t, J=6.0 Hz, 1H), 8.00 (t, J=1.8 Hz, 1H), 8.55 (d, J=1.8 Hz, 1H), 8.74 (d, J=1.8 Hz, 1H); MS (ES): m/z=281 [M+H]⁺.

Example 173

5-Phenylethynyl-nicotinic acid methyl ester

Add trimethylsilyl diazomethane (2.25 g, 19.7 mmol) to a cooled suspension of 5-phenylethynyl-nicotinic acid (2.0 g, 8.9 mmol) in 4:1 diethyl ether: methanol (30 mL) at 0° C. Warm to room temperature, stir for 2 h and concentrate. Purify the residue by silica gel chromatography, eluting with 0:100 to 50:50 ethyl acetate:hexanes, to give the title compound as a white solid (1.8 g, 85%).

¹H NMR (400 MHz, CDCl₃) δ 3.98 (s, 3H), 7.41-7.36 (m, 3H), 7.58-7.53 (m, 2H), 8.41 (t, J=2.2 Hz, 1H), 8.90 (d, J=1.8 Hz, 1H), 9.14 (d, J=2.2 Hz, 1H); MS (ES): m/z=238 [M+H]⁺.

Example 174

2-Fluoro-5-(5-methoxypyridin-3-ylethynyl)-benzamide

Add bis(triphenylphosphine)palladium (II) dichloride (70 mg, 0.10 mmol), copper (I) iodide (38 mg, 0.20 mmol), and 3-ethynyl-5-methoxypyridine, (prepared as described in PREPARATION 10), (350 mg, 2.6 mmol) to a solution of 2-fluoro-5-iodobenzamide, (prepared as described in PREPARATION 44), (0.54 g, 2.0 mmol) in triethylamine (3.1 mL, 30.3 mmol) and heat at 60° C. for 18 h. Cool to room temperature and concentrate. Purify by silica gel chromatography, eluting with 100:0 to 0:100 dichloromethane:ethyl acetate, to give the title compound as a white solid (480 mg, 68%).
¹H NMR (300 MHz, DMSO-d₆) δ 3.87 (s, 3H) 7.36-7.43 (m, 1H), 7.56-7.64 (m, 1H), 7.69-7.79 (m, 2H), 7.82-7.91 (m, 2H), 8.31-8.37 (m, 2H); MS (APCI): m/z=271 [M+H]⁺.

Example 175

5-Phenylethynyl-nicotinamide hydrochloride

Add 5-iodonicotinamide (0.25 g, 1.01 mmol) and bis(allylpalladium chloride) (0.009 g, 0.03 mmol) to a sealed flask and flush with argon. Add a 10% solution of tri-tert-butylphosphine (0.02 g, 0.1 mmol) in hexanes, phenylacetylene (0.15 g, 1.5 mmol) and a solution of 1,4-diazabicyclo[2.2.2]octane (Dabco) (0.23 g, 2.02 mmol) in N,N-dimethylformamide (0.5 mL) and stir at room temperature for 18 h. Dilute with ethyl acetate, wash with water, dry (magnesium sulfate) and filter. Add dichloromethane to the filtrate to produce a precipitate, which is isolated by filtration to give the free base of the title compound (0.11 g, 42%). Convert the free base to the hydrochloride salt as described in EXAMPLE 163 to give the title compound (0.112 g, 42%).
¹H NMR (400 MHz, CH₃OH-d4) δ 7.51-7.42 (m, 3H), 7.66-7.62 (m, 2H), 9.03 (t, J=1.5 Hz, 1H), 9.19 (d, J=8.3 Hz, 2H); MS (ES): m/z=223 [M+H]⁺.

Example 176

5-Phenylethynyl-nicotinic acid methyl ester hydrochloride

Add 1 M hydrogen chloride in diethyl ether (0.61 mL, 1.1 eq) to a solution of 5-phenylethynyl-nicotinic acid methyl ester, (prepared as described in EXAMPLE 173), (0.15 g, 0.56 mmol) in diethyl ether and stir at room temperature for 2 h. Isolate the precipitated solid by filtration to give the title compound (0.16 g, 93%).
¹H NMR (400 MHz, DMSO-d₆) δ 3.98 (s, 3H), 7.41-7.36 (m, 4H), 7.58-7.53 (m, 2H), 8.41 (t, J=2.2 Hz, 1H), 8.90 (d, J=1.8 Hz, 1H), 9.14 (d, J=2.2 Hz, 1H); MS (ES): m/z=238 [M+H]⁺.

Example 177

N,N-Dimethyl-5-phenylethynyl-nicotinamide hydrochloride

Add N-(3-dimethylaminopropyl)-N-ethylcarbodiimide hydrochloride (0.34 g, 1.8 mmol) to a solution of diisopropylethylamine (0.47 mg, 2.7 mmol), dimethylamine hydrochloride (0.11g, 1.34 mmol) and 5-phenylethynyl-nicotinic acid (0.2 g, 0.9 mmol) in tetrahydrofuran and stir at room temperature for 18 h. Dilute the reaction mixture with ethyl acetate and extract with an aqueous saturated solution of sodium carbonate. Extract the aqueous layer with ethyl acetate. Combine organic layers, dry (magnesium sulfate), filter and concentrate. Purify by silica gel chromatography, eluting with 40:60 to 80:20 ethyl acetate:hexanes, to give the free base of the title compound as a colorless oil. Convert the free base to the hydrochloride salt as described in EXAMPLE 163 to give the title compound (0.18 g, 69%).
¹H NMR (400 MHz, DMSO-d₆) δ 3.07 (s, 3H), 3.15 (s, 3H), 7.51-7.41 (m, 3H), 7.65-7.61 (m, 2H), 8.62 (t, J=1.8 Hz, 1H), 8.87 (s, 1H), 9.05 (s, 1H); MS (ES): m/z=251 [M+H]⁺.

Example 178

5-Phenylethynyl-thionicotinamide

Add Lawesson's Reagent, [2,4-bis(4-methoxyphenyl)-1,3-dithia-2,4-diphosphate -2,4-disulfide], (0.42 g, 1.03 mmol) to a suspension of 5-phenylethynyl-nicotinamide (0.12 g, 0.52 mmol) in toluene (3 mL) and stir for 48 h. Concentrate the reaction mixture and purify the residue by silica gel chromatography, eluting with 10:90 to 60:40 with ethyl acetate:hexanes, to give the title compound as a pale yellow solid (0.05 g, 40%).
¹H NMR (400 MHz, CDCl₃) δ 7.48-7.43 (m, 3H), 7.64-7.58 (m, 2H), 8.31 (t, J=2.2 Hz, 1H), 8.83 (d, J=2.2 Hz, 1H), 8.98 (d, J=2.2 Hz, 1H), 9.79 (s, 1H), 10.18 (s, 1H); MS (ES): m/z=239 [M+H]⁺.

Example 179

Dimethyl-(5-phenylethynyl-pyridin-3-ylmethyl)-amine hydrochloride

Add methanesulfonyl chloride (0.16 g, 1.44 mmol) to a solution of (5-phenylethynyl-pyridin-3-yl)-methanol, (prepared as described in EXAMPLE 152), (0.2 g, 0.96 mmol) and triethylamine (0.27 mL, 1.91 mmol) in dichloromethane (2 mL) at −78° C. and stir for 90 min. Dilute with dichloromethane, wash with an aqueous saturated solution of sodium bicarbonate, dry (magnesium sulfate), filter and concentrate. Dissolve the residue in acetonitrile (2 mL) and add dimethylamine hydrochloride (0.38 g, 4.7 mmol) and triethylamine (0.58 mL, 1.4 mmol) and stir for 3 h. Concentrate the reaction mixture and purify the residue by reverse phase HPLC, eluting with 0:100 to 100:0 acetonitrile:water with 0.1% trifluoroacetic acid, to give the trifluoroacetic acid salt of the title compound. Dissolve the trifluoroacetic acid salt in diethyl ether and add 1 M hydrogen chloride (1.1 eq.) in diethyl ether. Stir for 2 h and collect the precipitated solid by filtration to give the title compound (0.015 g).
¹H NMR (400 MHz, CH₃OH-d4) δ 2.95 (s, 6H), 4.51 (s, 2H), 7.47-7.41 (m, 3H), 7.62-7.57 (m, 2H), 8.46 (s, 1H), 8.84 (s, 1H), 8.99 (s, 1H); MS (ES): m/z=237 [M+H]⁺.

Example 180

5-Phenylethynyl-nicotinic acid N'-acetyl-hydrazide hydrochloride

Add oxalyl chloride (0.39 g, 4.48 mmol) dropwise to a cooled suspension of 5-phenylethynyl-nicotinic acid (0.50 g, 2.24 mmol) in dichloromethane (5.0 mL) at 0° C. Warm to room temperature, stir for 2 h and concentrate. Triturate the residue with toluene (3×20 mL) to give a solid. Dissolve the solid in dichloromethane (5 mL), add acetyl hydrazide (0.20 g, 2.69 mmol) and stir at room temperature for 18 h. Pour the reaction mixture into an ice cold aqueous saturated solution of sodium bicarbonate and collect the precipitated solid by filtration. Partition the collected solid between a 10% solution of isopropanol:chloroform and water and then separate the layers. Dry (magnesium sulfate), filter and concentrate to obtain the free base of the title compound. Dissolve the free base in methanol and add 1 M hydrogen chloride in diethyl ether. Stir for 2 h and collect the precipitated solid by filtration to give the title compound (0.32 g, 51%).

$^1$H NMR (400 MHz, CH$_3$OH-d4) δ 2.08 (s, 3H), 7.48-7.41 (m, 3H), 7.65-7.60 (m, 2H), 8.76 (t, J=1.8 Hz, 1H), 9.09 (dd, J=11.0 Hz, J=1.8 Hz, 2H); MS (ES): m/z=280 [M+H]$^+$.

Example 181

3-Chloro-5-(3-chloro-4-fluorophenylethynyl)-pyridine

Add bis(triphenylphosphine)palladium (II) dichloride (64 mg, 0.091 mmol), copper (I) iodide (35 mg, 0.18 mmol), and 3-chloro-5-ethynylpyridine, (prepared as described in PREPARATION 27), (250 mg, 1.8 mmol) to a solution of 2-chloro-1-fluoro-4-iodobenzene (560 mg, 2.2 mmol) in triethylamine (3.8 mL, 27 mmol) and heat at 60° C. for 5 h. Cool to room temperature and concentrate. Purify by silica gel chromatography, eluting with 50:50 to 100:0 dichloromethane:hexanes, followed by a second silica gel chromatography, eluting with 100:0 to 90:10 hexanes:ethyl acetate, to give the title compound as a white solid (340 mg, 70%).

$^1$H NMR (300 MHz, CDCl$_3$) δ 7.11-7.19 (t, J=8.6 Hz, 1H), 7.38-7.46 (m, 1H), 7.58-7.64 (m, 1H), 7.77-7.81 (t, J=2.0 Hz, 1H), 8.52-8.55 (d, J=2.3 Hz, 1H), 8.60-8.63 (d, J=1.7 Hz, 1H); MS (APCI): m/z=266 [M+H]$^+$.

Example 182

5-(5-Chloropyridin-3-ylethynyl)-2-fluorobenzonitrile

Add bis(triphenylphosphine)palladium (II) dichloride (77 mg, 0.11 mmol), copper (I) iodide (42 mg, 0.22 mmol), and 3-chloro-5-ethynylpyridine, (prepared as described in PREPARATION 27), (300 mg, 2.2 mmol) to a solution of 2-fluoro-5-iodobenzonitrile (650 mg, 2.6 mmol) in triethylamine (4.6 mL, 33 mmol) and heat at 60° C. for 6 h. Cool to room temperature and concentrate. Purify by silica gel chromatography, eluting with 50:50 dichloromethane:hexanes to 90:10 dichloromethane:ethyl acetate, followed by a second silica gel chromatography eluting with 95:5 to 75:25 hexanes:ethyl acetate, to give the title compound as an off-white solid (510 mg, 91%).

$^1$H NMR (300 MHz, CH$_3$OH-d4) δ 7.40-7.48 (t, J=8.9 Hz, 1H), 7.88-7.97 (m, 1H), 8.00-8.09 (m, 2H), 8.55-8.58 (d, J=2.3 Hz, 1H), 8.63-8.66 (d, J=1.7 Hz, 1H); MS (APCI): m/z=257 [M+H]$^+$.

Example 183

2-Fluoro-5-(5-methoxypyridin-3-ylethynyl)-benzoic acid

Add bis(triphenylphosphine)palladium (II) dichloride (70 mg, 0.10 mmol), copper (I) iodide (38 mg, 0.20 mmol), and 3-ethynyl-5-methoxypyridine, (prepared as described in PREPARATION 10), (400 mg, 3.0 mmol) to a solution of 2-fluoro-5-iodobenzoic acid (0.53 g, 2.0 mmol) in triethylamine (4.2 mL, 30.0 mmol) and stir at room temperature for 1 h. Heat at 50° C. for 18 h. Cool to room temperature and concentrate. Purify by silica gel chromatography, eluting with 100:0 to 60:40 ethyl acetate:methanol. Triturate the resulting solid with 3:1 hexanes:methanol to give the title compound as an off-white solid (295 mg, 54%).

$^1$H NMR (300 MHz, DMSO-d$_6$) δ 3.86 (s, 3H), 7.09-7.17 (m, 1H), 7.46-7.53 (m, 1H), 7.55-7.59 (m, 1H), 7.81-7.87 (m, 1H), 8.24-8.35 (m, 2H); MS (APCI): m/z=272 [M+H]$^+$.

Example 184

2-Fluoro-5-(5-methoxypyridin-3-ylethynyl)-N-methylbenzamide

Add bis(triphenylphosphine)palladium (II) dichloride (64 mg, 0.091 mmol), copper (I) iodide (35 mg, 0.19 mmol), and 3-ethynyl-5-methoxypyridine, (prepared as described in PREPARATION 10), (250 mg, 1.9 mmol) to a solution of 2-fluoro-5-iodo-N-methylbenzamide, (prepared as described in PREPARATION 39), (0.63 g, 2.3 mmol) in triethylamine (3.8 mL, 27.3 mmol) and heat at 60° C. for 16 h. Cool to room temperature and concentrate. Purify by silica gel chromatography, eluting with 100:0 to 10:90 dichloromethane:ethyl acetate, followed by a second silica gel chromatography eluting with 50:50 to 75:25 ethyl acetate:hexanes, to give the title compound as a white solid (390 mg, 73%).

$^1$H NMR (300 MHz, CDCl$_3$) δ 3.03-3.07 (m, 3H), 3.89 (s, 3H), 6.49-6.67 (br s, 1H), 7.07-7.16 (m, 1H), 7.28-7.32 (m, 1H), 7.57-7.66 (m, 1H), 8.26-8.33 (m, 2H), 8.35-8.37 (d, J=1.6 Hz, 1H); MS (APCI): m/z=285 [M+H]$^+$.

Example 185

2-Fluoro-5-(5-methoxypyridin-3-ylethynyl)-N,N-dimethylbenzamide hydrochloride

Add bis(triphenylphosphine)palladium (II) dichloride (72 mg, 0.103 mmol), copper (I) iodide (39 mg, 0.205 mmol), and 3-ethynyl-5-methoxypyridine, (prepared as described in PREPARATION 10), (300 mg, 2.3 mmol) to a solution of 2-fluoro-5-iodo-N,N-dimethylbenzamide, (prepared as described in PREPARATION 45), (0.600 g, 2.1 mmol) in triethylamine (4.3 mL, 31 mmol) and heat at 70° C. for 2 h. Concentrate and purify by silica gel chromatography, eluting with 50:50 to 100:0 ethyl acetate:hexanes, to give the free base of the title compound as a colorless oil. Dissolve the free base in diethyl ether (50 mL) and add 2 M hydrogen chloride in diethyl ether (4.4 mL, 8.9 mmol). Stir for 10 min, concentrate, triturate with diethyl ether and dry in vacuo to give the title compound as a white solid.

$^1$H NMR (300 MHz, CH$_3$OH-d4) δ 2.97 (s, 3H), 3.13 (s, 3H), 4.07 (s, 3H), 7.30-7.36 (m, 1H), 7.68-7.79 (m, 2H), 8.30 (s, 1H), 8.58-8.65 (m, 2H); MS (APCI): m/z 298 [M+H]$^+$.

Example 186

N-[2-Fluoro-5-(5-methoxypyridin-3-ylethynyl)-phenyl]-acetamide

Dissolve 2-fluoro-5-(5-methoxypyridin-3-ylethynyl)-phenylamine, (prepared as described in EXAMPLE 111), (200 mg, 0.83 mmol) in pyridine (3 mL) and add acetic anhydride (84 mg, 0.83 mmol). Stir under nitrogen at room temperature for 48 h and concentrate. Purify by silica gel chromatography, eluting with 100% ethyl acetate to give the title compound as a light yellow solid (180 mg, 76%).

$^1$H NMR (300 MHz, CDCl$_3$) δ 2.25 (s, 3H), 3.88 (s, 3H), 7.05-7.12 (s, 1H), 7.20-7.25 (m, 1H), 7.30-7.35 (m, 2H), 8.26 (d, J=2.8 Hz, 1H), 8.36 (d, J=1.6 Hz, 1H), 8.56-8.59 (m, 1H); MS (APCI): m/z=285 [M+H]$^+$.

Example 187

(E)-(5-Styrylpyridin-3-yl)-methanol

Add a solution of commercially available 5-phenylethynyl-nicotinic acid ethyl ester (0.4 g, 1.59 mmol) in dry tetrahydrofuran (20 mL) to a solution of lithium aluminum hydride (20 mL, 0.08 M in tetrahydrofuran) at room temperature under nitrogen and stir for 3 h. Add a solution of lithium aluminum hydride (2 mL, 1 M in tetrahydrofuran) and stir for 1 h. Slowly add methanol (2 mL) and concentrate. Dilute with ethyl acetate, wash with water and a saturated aqueous solution of sodium chloride and dry. Purify the residue by silica gel chromatography, eluting with 5:1 hexanes:ethyl acetate to 10:90 hexanes:ethyl acetate, to give the E-isomer (7 mg, 2%).

$^1$H NMR (300 MHz, CDCl$_3$) δ 3.12 (br s, 1H), 4.57 (s, 2H), 6.51 (d, J=12.5 Hz, 1H), 6.75 (d, J=12.1 Hz, 1H), 7.20 (m, 5H), 7.53 (s, 1H), 8.31 (s, 1H), 8.32 (s, 1H); MS (ES): m/z=212.2 [M+H]$^+$.

Example 188

(Z)-(5-Styrylpyridin-3-yl)-methanol

The Z-isomer may be prepared essentially as described in EXAMPLE 187 with the isolation of this isomer following similar silica gel chromatography conditions (42 mg, 13%).

$^1$H NMR (300 MHz, CDCl$_3$) δ 3.17 (br s, 1H), 4.75 (s, 2H), 7.03 (d, J=16.5 Hz, 1H), 7.16 (d, J=16.5 Hz, 1H), 7.26 (t, J=7.6 Hz, 2H), 7.36 (t, J=7.5 Hz, 1H), 7.49 (d, J=6.9 Hz, 2H), 7.88 (s, 1H), 8.40 (s, 1H), 8.55 (s, 1H); MS (ES): m/z=212.2 [M+H]$^+$.

Example 189

3-Chloro-5-(4-fluoro-3-nitrophenylethynyl)-pyridine

Add bis(triphenylphosphine)palladium (II) dichloride (150 mg, 0.22 mmol), copper (I) iodide (83 mg, 0.44 mmol), and 3-chloro-5-ethynylpyridine, (prepared as described in PREPARATION 27), (600 mg, 4.4 mmol) to a solution of 1-fluoro-4-iodo-2-nitrobenzene, (prepared as described in PREPARATION 46), (1.22 g, 4.6 mmol) in triethylamine (6.6 mL, 65.3 mmol). Stir at 60° C. for 18 h then concentrate. Purify by silica gel chromatography, eluting with a gradient of 100:0 to 90:10 dichloromethane:ethyl acetate, followed by a second silica gel chromatography, eluting with 95:5 to 60:40 hexanes:ethyl acetate, to give the title compound as a light yellow solid (650 mg, 54%).

$^1$H NMR (300 MHz, CDCl$_3$) δ 7.29-7.38 (m, 1H), 7.74-7.81 (m, 1H), 7.82-7.85 (t, J=2.1 Hz, 1H), 8.21-8.28 (dd, J=2.2 Hz, 7.0 Hz, 1H), 8.55-8.58 (d, J=2.3 Hz, 1H), 8.63-8.66 (d, J=1.7 Hz, 1H); MS (APCI): m/z=277 [M+H]$^+$.

Example 190

5-(5-Chloropyridin-3-ylethynyl)-2-fluorophenylamine

Add tin chloride dihydrate (7.13 mg, 31.6 mmol) to a solution of 3-chloro -5-(4-fluoro-3-nitrophenylethynyl)-pyridine, (prepared as described in EXAMPLE 189) (0.97 g, 3.51 mmol) in 2:1 ethanol:tetrahydrofuran (150 mL). Heat the mixture at 70° C. for 2.5 h. Cool to room temperature and concentrate. Dilute with a 50% solution of aqueous potassium hydroxide (300 g) and extract with diethyl ether (5×150 mL). Wash the combined extracts with water (1×50 mL) and saturated aqueous sodium chloride (1×50 mL). Dry (sodium sulfate), filter and concentrate. Purify by silica gel chromatography, eluting with 75:25 hexanes:ethyl acetate, to give the title compound as a light yellow solid (670 mg, 78%).

$^1$H NMR (300 MHz, CDCl$_3$) δ 3.80 (s, 2H), 6.85-7.02 (m, 3H), 7.75-7.79 (t, J=2.0 Hz, 1H), 8.48-8.51 (d, J=2.3 Hz, 1H), 8.58-8.61 (d, J=1.7 Hz, 1H); MS (APCI): m/z=247 [M+H]$^+$.

Example 191

N-[2-Fluoro-5-(5-methoxypyridin-3-ylethynyl)-phenyl]-methanesulfonamide

Dissolve 2-fluoro-5-(5-methoxypyridin-3-ylethynyl)-phenylamine, (prepared as described in EXAMPLE 111), (330 mg, 1.36 mmol) in dichloromethane (10 mL) under nitrogen and cool to 0° C. Add pyridine (0.240 ml, 2.99 mmol) followed by methanesulfonyl chloride (0.106 mL, 1.36 mmol) dropwise via syringe. Stir 14 h while allowing to warm to room temperature. Concentrate and purify by silica gel chromatography, eluting with 80:20 ethyl acetate:hexanes to 100% ethyl acetate, to give the title compound as a white solid (250 mg, 57%).

$^1$H NMR (300 MHz, CDCl$_3$) δ 3.09 (s, 3H), 3.89 (s, 3H), 6.59 (br s, 1H), 7.13-7.19 (m, 1H), 7.30-7.37 (m, 2H), 7.77-7.81 (m, 1H), 8.29 (d, J=2.9 Hz, 1H), 8.37 (d, J=1.6 Hz, 1H); MS (APCI): m/z=321 [M+H]$^+$.

Example 192

5-(5-Chloropyridin-3-ylethynyl)-2-fluoro-N,N-dimethylbenzamide hydrochloride

Add bis(triphenylphosphine)palladium (II) dichloride (46 mg, 0.07 mmol), copper (I) iodide (25 mg, 0.13 mmol), and 3-chloro-5-ethynylpyridine, (prepared as described in PREPARATION 27), (200 mg, 1.45 µmmol) to a solution of 2-fluoro-5-iodo-N,N-dimethylbenzamide, (prepared as described in PREPARATION 45), (0.600 g, 2.1 mmol) in triethylamine (4.3 mL, 31 mmol) and place in an oil bath at 70° C. Add toluene (10 mL) and heat for 2 h. Concentrate and purify by silica gel chromatography, eluting with 50:50 ethyl acetate:hexanes, to give the free base of the title compound as a colorless oil. Dissolve the free base in diethyl ether (50 mL) and add 2 M hydrogen chloride in diethyl ether (2.6 mL, 5.2 mmol). Stir for 10 min, concentrate, triturate with diethyl ether and dry to give the title compound as a light yellow solid (350 mg, >99%).

$^1$H NMR (300 MHz, CH$_3$OH-d4) δ 2.97 (s, 3H), 3.13 (s, 3H), 7.27-7.33 (m, 1H), 7.58-7.64 (m, 1H), 7.70-7.75 (m, 1H), 8.22-8.24 (m, 1H), 8.66-8.67 (m, 1H), 8.73-8.74 (m, 1H); MS (APCI): m/z=303 [M+H]$^+$.

Example 193

N-[5-(5-Chloropyridin-3-ylethynyl)-2-fluorophenyl]-acetamide

Add acetic anhydride (113 mg, 1.11 mmol) to a solution of 5-(5-chloropyridin-3-ylethynyl)-2-fluorophenylamine, (prepared as described in EXAMPLE 190) (0.275 g, 1.11 mmol)

in pyridine (4 mL). Stir the mixture at room temperature under nitrogen for 18 h then concentrate. Purify by silica gel chromatography, eluting with a gradient of 75:25 to 50:50 with hexanes:ethyl acetate, followed by a second silica gel chromatography, eluting with 75:25 to 60:40 hexanes:ethyl acetate, to give the title compound as a white solid (240 mg, 75%).

$^1$H NMR (300 MHz, CDCl$_3$) δ 2.25 (s, 3H), 7.05-7.14 (m, 1H), 7.20-7.26 (m, 1H), 7.34 (br s, 1H), 7.78-7.81 (m, 1H), 8.45-8.53 (d, J=2.3 Hz, 1H), 8.55-8.65 (m, 2H); MS (APCI): m/z=289 [M+H]$^+$.

Example 194

N-[5-(5-Chloropyridin-3-ylethynyl)-2-fluorophenyl]-methanesulfonamide

Add pyridine (193 mg, 2.44 mmol) followed by methanesulfonyl chloride (127 mg, 1.11 mmol) to a solution of 5-(5-chloropyridin-3-ylethynyl)-2-fluorophenylamine, (prepared as described in EXAMPLE 190), (275 mg, 1.11 mmol) in dichloromethane (10 mL) at 0° C. under nitrogen. Warm to room temperature and stir 20 h. Add additional methanesulfonyl chloride (32 mg, 0.28 mmol). Stir at room temperature for 2 h. Concentrate and purify by silica gel chromatography, eluting with 3:1 ethyl acetate:hexanes, to give the title compound as a white solid (330 mg, 92%).

$^1$H NMR (300 MHz, CDCl$_3$) δ 3.10 (s, 3H), 6.60 (br s, 1H), 7.14-7.20 (m, 1H), 7.32-7.37 (m, 1H), 7.77-7.82 (m, 2H), 8.54 (d, J=2.3 Hz, 1H), 8.63 (d, J=1.7 Hz, 1H); MS (APCI): m/z=325 [M+H]$^+$.

Example 195

3-(4-Fluoro-3-methoxyphenylethynyl)-5-methoxypyridine

Dissolve 1-fluoro-4-iodo-2-methoxybenzene, (prepared as described in PREPARATION 47), (1.0 g, 4.0 mmol) in triethylamine (15 mL, 108 mmol) and add 3-ethynyl-5-methoxypyridine, (prepared as described in PREPARATION 10), (500 mg, 3.8 mmol) followed by bis(triphenylphosphine)palladium (II) dichloride (100 mg, 0.14 mmol) and copper (I) iodide (60 mg, 0.32 mmol). Stir for 18 h at room temperature, concentrate and purify by silica gel chromatography, eluting with 3:1 hexanes:ethyl acetate. Further purify on silica gel, eluting with 9:1 dichloromethane:ethyl acetate, to give the title compound as a white solid (650 mg, 65%).

$^1$H NMR (300 MHz, CDCl$_3$) δ 3.88 (s, 3H), 3.92 (s, 3H), 6.98-7.15 (m, 3H), 7.29-7.31 (m, 1H), 8.27 (d, J=2.8 Hz, 1H), 8.37 (d, J=1.5 Hz, 1H); MS (APCI): m/z=258 [M+H]$^+$.

Example 196

3-Chloro-5-(4-fluoro-3-methoxyphenylethynyl)-pyridine

Dissolve 1-fluoro-4-iodo-2-methoxybenzene, (prepared as described in PREPARATION 47), (480 mg, 1.9 mmol) in triethylamine (7 mL, 53 mmol) and add 3-chloro-5-ethynylpyridine, (prepared as described in PREPARATION 27), (250 mg, 1.8 mmol) followed by bis(triphenylphosphine)palladium (II) dichloride (51 mg, 0.07 mmol) and copper (I) iodide (28 mg, 0.15 mmol). Stir for 18 h at room temperature, concentrate, and purify by silica gel chromatography, eluting with 3:1 hexanes:ethyl acetate. Further purify on silica gel, eluting with 100% dichloromethane, to give the title compound as a white solid (450 mg, 94%).

$^1$H NMR (300 MHz, CDCl$_3$) δ 3.93 (s, 3H), 7.04-7.14 (m, 3H), 7.79-7.81 (m, 1H), 8.51 (d, J=2.3 Hz, 1H), 8.62 (d, J=1.7 Hz, 1H); MS (APCI): m/z=262 [M+H]$^+$.

Example 197

5-(3-Hydroxymethylphenylethynyl)-nicotinonitrile

Add a 1 M solution of tetrabutylammonium fluoride in THF (3.33 mL, 3.33 mmol) to a solution of 5-trimethylsilanylethynyl-nicotinonitrile, (prepared as described in PREPARATION 3), (0.801 g, 4.00 mmol), in tetrahydrofuran (8.3 mL) and triethylamine (3.34 mL). After 5 min add zinc (II) bromide (1.56 g, 5.99 mmol), 3-iodobenzyl alcohol (0.42 mL, 3.33 mmol), and tetrakis(triphenylphosphine)palladium (0) (269 mg, 0.233 mmol). Heat to 55° C. for 2 h, cool to room temperature, and filter through diatomaceous earth. Purify by silica gel chromatography, eluting with 80:20 to 60:40 (1:1 hexanes:dichloromethane):ethyl acetate, to give the title compound as a yellow crystalline solid (380 mg, 49%).

$^1$H NMR (400 MHz, DMSO-d$_6$) δ 4.49 (d, J=5.7 Hz, 2H), 5.27 (t, J=5.7 Hz, 1H), 7.37-7.45 (m, 3H), 7.52-7.53 (m, 1H), 8.53 (t, 1H, J=2.0 Hz), 8.98-8.99 (m, 2H); MS (ES): m/z=235.0 [M+H]$^+$.

Example 198

5-(3-Cyanomethylphenylethynyl)-nicotinonitrile

Prepare according to the general procedure outlined in EXAMPLE 141 using 5-(3-chloromethylphenylethynyl)-nicotinonitrile, (prepared as described in PREPARATION 50), (200 mg, 0.79 mmol). Purify by silica gel chromatography, eluting with a gradient from 80:20 to 60:40 hexanes:ethyl acetate. Further purify by reverse phase chromatography, eluting with a gradient from 95:5 to 10:90 (0.1% aqueous trifluoroacetic acid):(0.1% trifluoroacetic acid in acetonitrile). Concentrate the fractions and partition between ethyl acetate and a saturated aqueous solution of sodium bicarbonate. Wash the organic with saturated aqueous sodium chloride, dry (sodium sulfate), filter, and concentrate to give the title compound as a white crystalline solid (48 mg, 25%).

$^1$H NMR (400 MHz, DMSO-d$_6$) δ 4.07 (s, 2H), 7.56-7.42 (m, 4H), 8.55 (t, 1H, J=2.0 Hz), 9.00 (app t, 2H, J=2.4 Hz); MS (ES): m/z=244.0 [M+H]$^+$.

Example 199

5-(3-Propylaminomethylphenylethynyl)-nicotinonitrile

Prepare according to the general procedure outlined in EXAMPLE 140 using 5-(3-chloromethylphenylethynyl)-nicotinonitrile, (prepared as described in PREPARATION 50), (100 mg, 0.40 mmol). Purify by silica gel chromatography, eluting with 95:5 to 70:30 (98:2 dichloromethane:7 N ammonia in methanol): (98:2 ethyl acetate:7 N ammonia in methanol), to give the title compound as a colorless oil, which crystallizes after concentration from diethyl ether (58 mg, 53%).

$^1$H NMR (400 MHz, DMSO-d$_6$) δ 0.82 (t, J=7.5 Hz, 3H), 1.39 (sext, J=7.2 Hz, 2H), 2.08 (br s, 1H), 2.39 (t, J=7.0 Hz, 2H), 3.66 (s, 2H), 7.34-7.43 (m, 3H), 7.54 (br s, 1H), 8.52 (t, J=2.0 Hz, 1H), 8.98 (d, J=1.8 Hz, 2H); MS (ES): m/z=276.2.0 [M+H]$^+$.

Example 200

5-(3-Cyano-4-fluorophenylethynyl)-nicotinonitrile

Add a 28% aqueous solution of ammonium hydroxide (10 mL) and iodine (279 mg, 1.10 mmol) to a solution of 5-(4-fluoro-3-formylphenylethynyl)-nicotinonitrile, (prepared as described in PREPARATION 38), (250 mg, 1.00 mmol) in tetrahydrofuran (5 mL). After 3.25 h quench with a 5% aqueous solution of sodium bisulfite (5 mL) and extract twice with ethyl acetate. Wash the organic layers with saturated aqueous sodium chloride, dry (sodium sulfate), filter, and concentrate. Dissolve the crude solid in dichloromethane and add PS-TsNNH$_2$ (3g, ~1.2 mmol, Argonaut). Stir the mixture for 20 min and filter through diatomaceous earth. Purify by silica gel chromatography, eluting with 90:10 to 80:20 (70:30 hexanes:dichloromethane):ethyl acetate, to give the title compound as a white crystalline solid (140 mg, 57%).

$^1$H NMR (400 MHz, DMSO-d$_6$) δ 7.62 (t, J=9.2 Hz, 1H), 7.98 (ddd, J=8.8, 5.3, 2.2 Hz, 1H), 8.22 (dd, J=6.2, 2.2 Hz, 1H), 8.54 (t, J=2.0 Hz, 1H), 9.00 (d, J=1.8 Hz, 1H), 9.02 (d, J=2.2 Hz, 1H); MS (ES): m/z=248.0 [M+H]$^+$; Anal Calcd for C$_{15}$H$_6$FN$_3$: C, 72.87; H, 2.45; N, 17.00. Found: C, 72.64; H, 2.73; N, 16.77.

Example 201

(E) 5-[2-(4-Chlorophenyl)-vinyl]-nicotinonitrile

Prepare essentially as described in EXAMPLE 15 using palladium(II) acetate (0.002 g, 0.01 mmol), tri-o-tolylphosphine (0.06 g, 0.02 mmol), copper (I) iodide (0.001 g, 0.005 mmol), 1-chloro-4-iodobenzene (0.24 g, 1 mmol) and 5-vinylnicotinonitrile, (prepared essentially as described in PREPARATION 51), (0.195 g, 1.5 mmol) at 100° C. for 7 h to give the title compound (0.170 g, 70%).

$^1$H NMR (300 MHz, CDCl$_3$) δ 7.02 (d, J=16.5 Hz, 1H), 7.17 (d, J=16.4 Hz, 1H), 7.36 (dt, J=8.8 and 2.2 Hz, 2H), 7.46 (dt, J=8.4 and 2.1 Hz, 1H), 8.06 (t, J=2.0 Hz, 1H), 8.74 (d, J=1.9 Hz, 1H), 8.88 (d, J=2.2 Hz, 1H); MS (ES): m/z=241.0, 243.0 [M+H]$^+$.

Example 202

(E) 5-[2-(3-Trifluoromethylphenyl)-vinyl]-nicotinonitrile

Prepare essentially as described in EXAMPLE 15 using palladium(II) acetate (0.002 g, 0.01 mmol), tri-o-tolylphosphine (0.06 g, 0.02 mmol), copper (I) iodide (0.001 g, 0.005 mmol), 1-iodo-3-trifluoromethylbenzene (0.140 mL, 1 mmol) and 5-vinylnicotinonitrile, (prepared essentially as described in PREPARATION 51), (0.195 g, 1.5 mmol) at 100° C. for 7 h to give the title compound (0.149 g, 54%).

$^1$H NMR (300 MHz, CDCl$_3$) δ 7.12 (d, J=16.5 Hz, 1H), 7.25 (d, J=16.4 Hz, 1H), 7.50-7-60 (m, 2H), 7.70 (d, J=7.3 Hz, 1H), 7.78 (s, 1H), 8.09 (t, J=2.0 Hz, 1H), 8.76 (d, J=2.2 Hz, 1H), 8.92 (d, J=2.2 Hz, 1H); MS (ES): m/z=275.1 [M+H]$^+$.

Example 203

5-(3-Trifluoromethylphenylethynyl)-pyridin-3-ylamine dihydrochloride

Prepare according to the procedure outlined in EXAMPLE 2 with [5-(3-trifluoromethylphenylethynyl)-pyridin-3-yl]-carbamic acid tert-butyl ester, (prepared essentially as described in EXAMPLE 154), (0.540 g, 1.49 mmol) with the corresponding 3-bromo-5-(3-trifluoromethylphenylethynyl)-pyridine, (prepared as described in EXAMPLE 55), to give the title compound (300 mg, 60%).

$^1$H NMR (300 MHz, CH$_3$OH-d4) δ 7.66 (m, 1H), 7.69 (m, 1H), 7.76 (d, J=8.1 Hz, 1H), 7.85 (d, J=8.1 Hz, 1H), 7.90 (br s, 1H), 8.01 (br s, 1H), 8.14 (br s, 1H); MS (ES): m/z=263 [M+H]$^+$.

Example 204

N-[5-(5-Cyanopyridin-3-ylethynyl)-2-fluorophenyl]-acetamide

Dissolve 5-(3-amino-4-fluorophenylethynyl)-nicotinonitrile, (prepared as described in EXAMPLE 160), (0.2 g, 0.8 mmol) in anhydrous pyridine. A solution of acetyl chloride (0.07 g, 0.88 mmol) in tetrahydrofuran is added to the reaction and stirred overnight at room temperature. Concentrate and dissolve the crude reaction in ethyl acetate and water. Wash the organic layer with water, an aqueous saturated solution of sodium chloride, dry (potassium carbonate), filter, concentrate and purify (silica gel chromatography, eluting with 95:5 to 80:20 dichloromethane:ethyl acetate), to give the title compound as a white solid (180 mg, 81%).

$^1$H NMR (400 MHz, DMSO-d$_6$) δ 2.11 (s, 3H), 7.36-7.35 (m, 1H), 7.37 (d, J=1.3 Hz, 1H), 8.23 (d, J=7.0 Hz, 1H), 8.57 (t, J=2.0 Hz, 1H), 9.03-9.01 (m, 2H), 9.89 (s, 1H); MS (ES): m/z=280 [M+H]$^+$.

Example 205

N-[5-(5-Cyanopyridin-3-ylethynyl)-2-fluorophenyl]-methanesulfonamide

Dissolve 5-(3-amino-4-fluorophenylethynyl)-nicotinonitrile, (prepared as described in EXAMPLE 160), (0.2 g, 0.8 mmol) in anhydrous pyridine. Add a solution of methanesulfonyl chloride (0.1 g, 0.88 mmol) in tetrahydrofuran to the reaction and stir overnight at room temperature. Concentrate and dissolve the crude reaction in ethyl acetate and water. Wash the organic layer with water, an aqueous saturated solution of sodium chloride, dry (potassium carbonate), filter, concentrate and purify (silica gel chromatography, eluting with 95:5 to 80:20 dichloromethane:ethyl acetate), to give the title compound as a tan solid (50 mg, 20%).

$^1$H NMR (400 MHz, DMSO-d$_6$) δ 2.58 (s, 3H), 6.66 (ddd, 1H, J=8.0, 4.3, 2.1 Hz), 6.90 (dd, 1H, J=11.9, 7.9 Hz), 7.45 (dd, 1H, J=8.8, 2.2 Hz), 8.53 (t, 1H, J=2.0 Hz), 8.96 (d, 2H, J=2.2 Hz), 8.96 (d, 1H, J=2.2 Hz); MS (ES): m/z=314 [M−H]$^-$.

Example 206

N-[5-(5-Cyanopyridin-3-ylethynyl)-2-fluorophenyl]-N-methanesulfonyl-methanesulfonamide Dissolve 5-(3-amino-4-fluorophenylethynyl)-nicotinonitrile, (prepared as described in EXAMPLE 160), (0.2 g, 0.8 mmol) in anhydrous pyridine. Add a solution of methanesulfonyl chloride (0.2 g, 1.9 mmol) in tetrahydrofuran to the reaction and heat at 50° C. for 16 h. Concentrate and dissolve the crude reaction in ethyl acetate and water. Wash the organic layer with water, an aqueous saturated solution of sodium chloride, dry (potassium carbonate), filter, concentrate and purify (silica gel chromatography, eluting with 100:0 to 80:20 dichloromethane:ethyl acetate), to give the title compound as a white solid (114 mg, 36%).

$^1$H NMR (400 MHz, DMSO-d$_6$) δ 3.57 (s, 6H), 7.57 (dd, 1H, J=9.4, 8.6 Hz), 7.82 (ddd, 1H, J=8.4, 4.8, 2.2 Hz), 8.01

(dd, 1H, J=7.0, 2.2 Hz), 8.58 (t, 1H, J=2.2 Hz), 9.05-9.04 (m, 2H); MS (ES): m/z=394 [M+H]+.

Example 207

[5-(5-Cyanopyridin-3-ylethynyl)-2-fluorophenyl]-carbamic acid methyl ester

Dissolve 5-(3-amino-4-fluorophenylethynyl)-nicotinonitrile, (prepared as described in EXAMPLE 160), (0.4 g, 1.7 mmol) in anhydrous pyridine. Add a solution of methylcarbamyl chloride (0.17 g, 1.8 mmol) in anhydrous tetrahydrofuran carefully to the reaction and stir overnight at room temperature. Concentrate and dissolve the crude reaction in ethyl acetate and water. Wash the organic layer with water, an aqueous saturated solution of sodium chloride, dry (potassium carbonate), filter, concentrate and purify (silica gel chromatography, eluting with 0:100 to 10:90 ethyl acetate:dichloromethane, and then further purify on C-18 silica, eluting with 10:90 to 50:50 using an aqueous 0.1% solution of trifluoroacetic acid and a 0.1% solution of trifluoroacetic acid in acetonitrile). Concentrate, partition the residue between ethyl acetate and an aqueous saturated solution of sodium bicarbonate and separate the layers. Wash the organic layer with an aqueous saturated solution of sodium chloride, dry (potassium carbonate), filter and concentrate to give the title compound as a white solid (25 mg, 5%).

$^1$H NMR (400 MHz, DMSO-$d_6$) δ 3.69 (s, 3H), 7.39-7.31 (m, 2H), 7.95 (d, 1H, J=6.6 Hz), 8.57 (t, 1H, J=2.2 Hz), 9.02 (t, 2H, J=2.2 Hz), 9.58 (s, 1H); MS (ES): m/z=296 [M+H]+.

We Claim:
1. A compound of formula 1:

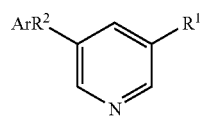

(1)

wherein
Ar is 2-chlorophenyl, 3-chlorophenyl, 2-fluorophenyl, 3-fluorophenyl, 4-fluorophenyl, 3,4-dimethylphenyl, 3,5-dimethylphenyl, 2,4-dimethylphenyl, 2,5-dimethylphenyl, 2-cyanophenyl, 3-cyanophenyl, 2-methoxyphenyl, 3-methoxyphenyl, 4-methoxyphenyl, 4-chlorophenyl, 2-methylphenyl, 3-methylphenyl, 4-methylphenyl, 3,4-difluorophenyl, 3,5-difluorophenyl, 3,4,5-trifluorophenyl, 3-bromophenyl, 3-nitrophenyl, 3-trifluoromethylphenyl, 3-aminophenyl, 3-chloro-4-fluorophenyl, 3-hydroxyphenyl, 3-acetylphenyl, 5-chloro-2-methoxyphenyl, 3-chloro-4-methoxyphenyl, 3-hydroxy-4-fluorophenyl, 3-methoxy-4-fluorophenyl, 3-ethoxy-4-fluorophenyl, 3-isopropoxy-4-fluorophenyl, 3-isopropylphenyl, 3-ethylphenyl, 3-methyl-4-fluorophenyl, 3-trifluoromethyl-4-fluorophenyl, 3-cyano-4-fluorophenyl, 3-amino-4-fluorophenyl, 3-trifluoromethyl-4-fluorophenyl, 3-chloro-4-fluorophenyl, 3-nitro-4-fluorophenyl, 3-aminocarbonyl-4-fluorophenyl, 3-N-methylaminocarbonyl-4-fluorophenyl, 3-N,N-dimethylaminocarbonyl-4-fluorophenyl, 3-carboxyl-4-fluorophenyl, 3-methoxycarbonyl-4-fluorophenyl, 3-acetylaminomethyl-4-fluorophenyl, 3-methysulfonylaminomethyl-4-fluorophenyl, 3-pivaloylaminomethyl-4-fluorophenyl, 3-trifluoromethoxyphenyl, 3-aminomethyl-4-fluorophenyl, 3-dimethylaminomethyl-4-fluorophenyl, 3-cyanomethyl-4-fluorophenyl, 4-fluoro-3-hydroxymethylphenyl, 3-{[(2-cyanoethyl)-methylamino]-methyl}-4-fluorophenyl, 4-fluoro-3-[(isopropylmethylamino)-methyl]phenyl, 4-fluoro-3-isopropylaminomethylphenyl, 4-fluoro-3-propylaminomethylphenyl, 3-ethylaminomethyl-4-fluorophenyl, 4-fluoro-3-methyl aminomethylphenyl, or 3-isobutyrylamino-4-fluorophenyl;
$R^1$ is CN, iodo, chloro, methyl or $COR^3$;
$R^2$ is 1,2-ethynediyl; and
$R^3$ is hydrogen or $C_1$-$C_4$ alkyl;
or a pharmaceutically acceptable salt thereof; or an N-oxide thereof.
2. The compound of claim 1 wherein $R^1$ is CN.
3. The compound of claim 1 wherein $R^3$ is methyl.
4. The compound claim 1 wherein $R^3$ is hydrogen.
5. A compound of claim 1 which is:
5-(4-Fluorophenylethynyl)-nicotinonitrile, 5-(3-Cyanophenylethynyl)-nicotinonitrile or 5-(3,4-difluorophenylethynyl)-nicotinonitrile.
6. A process for preparing a compound of formula 1 (or a pharmaceutically acceptable salt thereof) as provided in claim 1 which comprises:
(a) for a compound of formula 1 in which $R^2$ is 1,2-ethenediyl, reacting with a compound of formula II

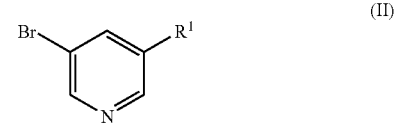

(II)

with a compound of formula Ar—CHCH$_2$ in a Heck coupling;
(b) for a compound of formula 1 in which $R^2$ is alkynyl, reacting with a compound of formula III

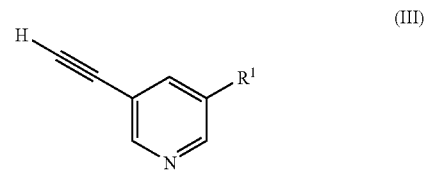

(III)

in a Sonogashira coupling with a compound of formula Ar—I or Ar—Br in a suitable solvent;
whereafter, for any of the above procedures, when a pharmaceutically acceptable salt of a compound of formula 1 is required, it is obtained by reacting the basic form of such a compound of formula 1 with an acid affording a physiologically acceptable counterion, or, for a compound of formula 1 which bears an acidic moiety, reacting the acidic form of such a compound of formula 1 with a base which affords a pharmaceutically acceptable cation, or by any other conventional procedure; and wherein, unless more specifically described, the value of $R^1$, Ar and $R^2$ are as defined in claim 1.
7. The compound of claim 1 which is 5-(3-Chlorophenylethynyl)-nicotinonitrile or a pharmaceutically acceptable salt thereof.

* * * * *